United States Patent [19]
Resnick et al.

[11] Patent Number: 5,489,524
[45] Date of Patent: Feb. 6, 1996

[54] CHIMERIC PROTEIN THAT HAS A HUMAN RHO MOTIF AND DEOXYRIBONUCLEASE ACTIVITY

[75] Inventors: Michael A. Resnick, Chapel Hill; Edward L. Perkins, Carrborro, both of N.C.; Terry Chow, Fleurimont, Canada

[73] Assignee: The United States of America as represented by the Department of Health and Human Services, Washington, D.C.

[21] Appl. No.: 914,284

[22] Filed: Jul. 14, 1992

Related U.S. Application Data

[63] Continuation-in-part of Ser. No. 674,801, Mar. 26, 1991, abandoned.

[51] Int. Cl.$^6$ ..................................................... C12N 9/22
[52] U.S. Cl. ........................................... 435/199; 435/193
[58] Field of Search ........................... 435/199; 536/23.2

[56] References Cited

PUBLICATIONS

Barondess, J. T., et al., (1990) Nature 346, 871–874.
Sanger, F., et al, (1982) J. Mol. Biol. 162, 729–773.
Chow, T. & Resnick, M., "Purification and characterization of an endoexonuclease from *Saccharomyces cerevisiae* that is influenced by the RAD52 gene," *Journal of Biological Chemistry*, vol. 262, No. 36, 25 Dec. 1987, Baltimore, Maryland, pp. 17659–17667.
Moran, L. et al., "Nucleotide sequence of the phage lambda gt11 SacI–KpnI lacZ region," *Gene*, vol. 93, 1990, Amsterdam, Netherlands, pp. 163–164.
Resnick, M. et al., *Database WPI*, Section Ch, Week, 9149, Derwent Publications Ltd., London, GB, Class B04, AN 91–361692 and US–Published–Patent–Application 7674801. (1991).
Chien, C. T. et al., "The two–hybrid system: a method to identify and clone genes proteins that interact with a protein of interest," *Proc. Nat. Acad. of Sciences, U.S.A.*, vol. 88, No. 1991, Washington, US, pp. 9578–9582.
Chow, T. et al., *Database WPI*, Section Ch, Week 9318, Derwent Publications Ltd., London, GB, Class B04, AN 93–152048, and US–Published–Patent–Application 7914284. (1992).
Couture C. & T. Chow et al., "Purification and characterization of mammalian endo–exonuclease," *Nucleic Acids Research*, vol. 20, No. 16, 25 Aug. 1992, Arlington, Va., pp. 4355–4361.
Rosenberg, S. and Hastings, P., "The split–end model for homologous recombination at double–strand breaks and at Chi," *Biochimie* 73:385–397 (1987).
Fraser, et al., "*Neurospora* Endo–Exonuclease Is Immunochemically Related to the *recC* Gene Product of *Escherichia coli*," *J. Bacteriology* 172:507–510 (1990).
Kunz, B. and Haynes, R., "Phenomenology and Genetic Control of Mitotic Recombination in Yeast," *Ann. Rev. Genet.* 15:57–89 (1981).
Koa, H. et al., "Endo–exonuclease of *Aspergillus nidulans*," *Biochem. Cell Biol.* 68:387–392 (1989).

Dake, et al., "Purification and Properties of the Major Nuclease from Mitochondria of *Saccharomyces cerevisiae*," *J. Biol. Chem.* 263:7691–7702 (1988).
Chardin, P. et al., "Coding Sequence of human *rho* cDNAs clone 6 and clone 9," *Nucleic Acids Research* 16:2717 (1988).
Chow, T. and Resnick M., "An endo–exonuclease activity of yeast that requires a functional RAD52 gene," *Mol. Gen. Genet* 211:41–48 (1988).
Yeramian, P. et al., "Nucleotide sequence of human rho cDNA clone 12" *Nucleic Acids Research* 15:1869 (1987).
Madaule, P. et al., "characterization of two members of the rho gene family from the yeast *Saccharomyces cerevisiae*" *Proc. Natl. Acad. Sci. USA* 84:779–783 (1987).
Ramotar, D. et al., "Nuclear Endo–exonuclease of *Neurospora crassa*" *J. Biol. Chem.* 262:425–431 (1987).
Tomkinson, A. and Linn, S., "Purification and properties of a single strand–specific endonuclease from mouse cell mitochondria" *Nucleic Acids Research* 14:9579–9593 (1986).
Snyder, M. et al., "Rapid mapping of antigenic coding regions and constructing insertion mutations in yeast genes by mini–Tn10 transplason mutagenesis" *Proc. Natl. Acad. Sci. USA* 83:730–734 (1986).
Fraser, M. et al., "An immunochemical study of *Neurospora* nucleases" *Biochem. Cell Biol.* 64:106–116.
Madaulel, P. and Axel, R., "A novel ras–Related Gene Family," *Cell*. 41:31–40 (1985).
Devereux, J. et al., "A comprehensive st of sequence analysis program for the V A X," *Nucleic Acids Research* 12:387–395 (1984).
Resnick, M.. et al., "DNA Polymerases, Deoxyribonucleases, and recombination during meiosis in *Saccharaomes cerevisiae*" *Mol. Cell Biol.* 4:2811–2817 (1984).
Chaudhury A. and Smith G., "A new class of *Escherichia coli* recBC mutants: Implications for the role of RecBC enzyme in homologous recombination," *Proc. Natl. Acad. Sci. USA* 81:7850–7854 (1984).
Rothestein, R., "One–step gene disruption in yeast" *Methods in Enzymology* 101:202–221 (1983).
Chow, T. and Fraser, M., "Purification and properties of single strand DNA–binding endo–exonuclease of *Neurospora crassa*" *J. Biol. Chem.* 258:12010–12018 (1983).
Elder, T. et al., "RNA from the yeast transposable element tyl has both ends in the direct repeats a structure similar to retrovirus RNA" *Proc. Natl. Acad. Sci. USA* 80:2432–2436 (1983).

(List continued on next page.)

*Primary Examiner*—Charles L. Patterson, Jr.
*Attorney, Agent, or Firm*—Knobbe, Martens, Olson & Bear

[57] ABSTRACT

The present invention relates, in general, to endo-exonucleases. In particular, the present invention relates to DNA segments encoding for a polypeptide having an amino acid sequence corresponding to mammalian endo-exonuclease, a polypeptide having an amino acid sequence corresponding to mammalian endo-exonuclease, antibodies to mammalian endo-exonuclease, a recombinant DNA molecule, mutant cells substantially lacking endo-exonuclease activity, a cell containing mammalian endo-exonuclease, and methods of producing and using the polypeptide, DNA segment and mutants.

12 Claims, 23 Drawing Sheets

PUBLICATIONS

Young, A. and Davis, R., "Efficient isolation of genes by using antibody probes" *Proc. Natl. Acad. Sci. USA* 80:1194–1198 (1983).

Malone, R. and Esposito, R., "RAD52 gene is required for homothallic interconversion of mating types and spontaneous mitotic recombination in yeast," *Proc. Natl. Acad. Sci. USA.* 77:503–507 (1980).

Towbin, H. et al., "Electrophoretic transfer of proteins from polyacrylamide gels to mitrocellulose sheets: Procedure and some applications," *Proc. Natl. Acad. Sci. USA* 76:4350–4354 (1979).

Chow, T. and Fraser, M., "The major intracellular alkali deoxyribonuclease activities expressed in wild–type and Rec–like mutants of *Neurospora crassa*" *Can. J. Biochem.* 57: 889–901 (1979).

Sanger, F. and Coulson, A., "The use of thin acrylamide for DNA sequencing" *MRS Lab. Mol. Biol.* 87:107–110 (1978).

McMaster G. and Charmichael, G., "Analysis of single– and double–stranded nucleic acids on polyacrylamide and agarose gels by using glyoxal and acridine orange" *Proc. Natl. Acad. Sci. USA* 74:4835–4838 (1977).

Berk, A. an Phillip, A., "Sizing and mapping of early adenovirus mRNAs by gel electrophoresis of S1 endonuclease–digested hybrids" *Cell.* 12:721–731 (1977).

Resnick,M. and Martin, P., "The repair of double–strand breaks in the Nuclear DNA of *Saccharomyces cerevisiae* and its genetic control" *Molec. gen. Genet.* 143:119–129 (1976).

Kohler, G. and Milstein C., "Continuous cultures of fused cells secreting antibody of predefined specifity" *Nature* 256:495–497 (1975).

Zhu, H. et al., "Determination of the carboxyl termini of the alpha and beta subunits of yeast K1 killer toxin" *J. Biol. Chem.* 262:10728–10732 (1987).

Ho, K. and Mortimer, R., "Induction of dominant lethality by x–rays in a radiosensitive strain of yeast," *Mutation Research* 20:45–51 (1973).

Hollowman, W. and Holliday, R., "Studies on a nuclease from ustilago maydis" *J. Biol. Chem.* 23:8107–8113 (1973).

Fraser, M. et al., "Nucleases and their control in wild–type and nuh mutants for neurospora" *Dept. Biochem. Biol. McGill University* Chapter 5:63–74 (1979).

Young, R. and Davis, R., "Yeast RNA polymerase II genes; Isolation with antibody probes," *Science* 222:778–782 (1983).

Chow, T. et al., "Repair and recombination defective mei–41 mutants of drosophila lack a Dnase which is related to nucleases from fungi" *J. Cell. Biochem.* 10B:211 (1986).

Esposito, et al.; Current Genetics 1986 10:425–433; "The REC46 gene of *Saccharomyces cerevisiae* controls mitotic chromosomal stability, recombination and sporulation: cell–type and life cycle stage–specific expression of the rec46–1 mutation".

Kouprina, et al.; Yeast vol. 4:257–269 (1988); "Genetic Control of Chromosome Stability in the Yeast *Saccharomyces cerevisiae*".

Fitzgerald–Hayes, Molly; Yeast; vol. 3: 187–200 (1987) "Yeast Centromeres".

Chow and Resnick; Cellular Response to DNA Damage, pp. 447–455; 1983 "The Identification of A Deoxyribonuclease Controlled by the RAD52 Gene of *Saccharomyces cerevisiae*".

Hibino, et al.; Biochimica et Biophysica Acta, 1088 (1991) 305–307; BBA Report; "A Nuclease from Rat–Liver Nuclei with Endo– and Exonucleolytic Activity".

Chien, et al.; Proc. Natl. Acad. Sci. USA; vol. 88; pp. 9578–9582; Nov. 1991; Biochemistry; "The Two–Hybrid System: A Method to Identify and Clone Genes For Proteins that Interact with a Protein of Interest".

Sander, et al.; 1991 Oxford University Press: Nucleic Acids Research, vol. 19, No. 16, pp. 4523–4529; "Cloning and Characterization of Rrp1, The Gene Encoding Drosophila Strand Transferase: Carboxy–terminal Homology to DNA Repair Endo/exonucleases".

Fraser, et al.; Journal of Bacteriology, Jan. 1990; pp. 507–510; vol. 172, No. 1; "Neurospora Endo–Exonuclease Is Immunochemically Related to the recC Gene Product of *Escherichia coli*".

Suggs, et al.; Proc. Natl. Acad. Sci. USA; vol. 78; No. 11; pp. 6613–6617; Nov. 1981; Biochemistry; "Use of Synthetic Oligonucleotides as Hybridization Probes: Isolation of Cloned cDNA Sequences for Human MB2–Microglobulin".

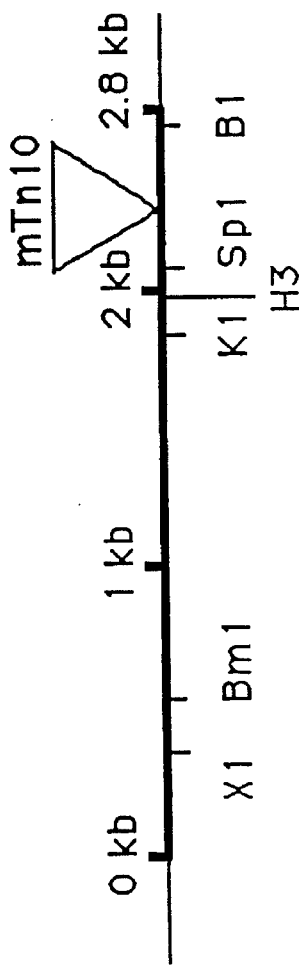
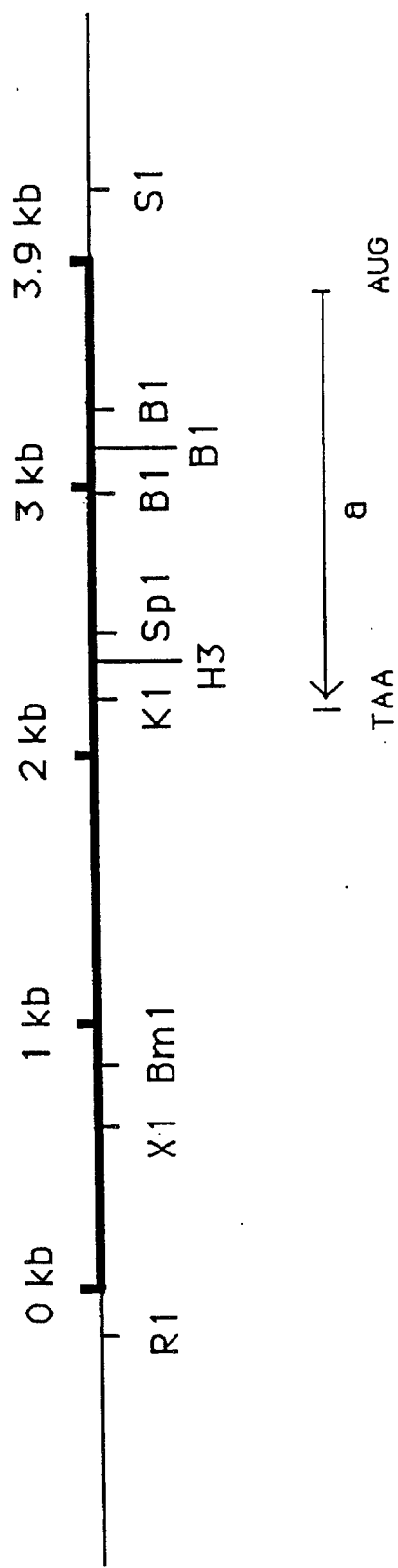
FIG. 1A
FIG. 1B

FIG. 2A

```
-119  TG ATT AAG TAG TTA TAG CCT TAC GTT AAG ACG ACA AAA GAC CAT GAT AAG CAT CCC TCA AAA
 -58  GTT ACA GCA AAC TTA AGT CAA ATA GGT CAC AAA AAT CTC CAA TAG TAA CGC TTT TTC ATG
                                                                                    M      3

4  AAT ACA CTA TTT AAG CGA AAA GGT GGC AAT TGT GAA AGT TTA GAT GAA AAG CAT AAC ATA GTT TCG     63
        N   T   L   F   K   R   K   G   G   N   C   E   S   L   D   E   K   N   I   V   S

64  CAG GGA TCG CCC TCA AGT AGC ATA CAA ATA GGT CCT CTT CCT GAA TCA ACT TTA CCT GGC GAA AAG AAT    123
        Q   G   S   P   S   S   S   I   Q   I   G   P   L   P   E   S   T   L   P   G   E   K   N

124  CTC CAG ATT GCC TAC TCA TTC GCT AGA AGC CTT CAC TAC AGT CCT TCT ATT CCT AGT TAT GAG CAG ATG    183
        L   Q   I   A   Y   S   F   A   R   S   L   H   Y   S   P   S   I   P   S   Y   E   Q   M

184  AAA CGT ACA AAA CTG CCA GAT TAT TAC CTA AAG ATT GTT GTT GGA GAT GGC A     243
        K   R   T   K   L   P   D   Y   Y   L   K   I   V   V   G   D   G   A

244  GTA GGG AAG ACG TGC CTG CTG ATA TCT TAT GTC CAA GGA ACA TTT CCG ACT GAT TAT ATT     303
        V   G   K   T   C   L   L   I   S   Y   V   Q   G   T   F   P   T   D   Y   I

304  CCT ACT ATT TTC GAA AAT TAT GTC ACA AAC ATA GAA GAA CCC AAC GGT CAA ATT ATA GAA     363
        P   T   I   F   E   N   Y   V   T   N   I   E   E   P   N   G   Q   I   I   E

364  TTG GCA TTA TGG GAC ACT GCC CAA GAG TAT TCT GTT AGA CTT AAG CCG CTT TCA TAT     423
        L   A   L   W   D   T   A   Q   E   Y   S   V   R   L   K   P   L   S   Y

424  AGG AAT GCA GAT GTG CTG ATG GTG TGC TTT GTT TCT GGT AGT ACA TCG CTT AAA AAT     483
        R   N   A   D   V   L   M   V   C   F   V   S   G   S   T   S   L   K   N

484  GTG GAA GAT CTC TGG TTC CCA GAG GTT AAG CAT TTT TGT CCT TCC ACT CCA ATC ATG CTA     543
        V   E   D   L   W   F   P   E   V   K   H   F   C   P   S   T   P   I   M   L

544  GTC GGC CTT AAA TCA GAT CTA TAT GAA GCT TTG GAA CAT TTG CAC ATA TTC AAG CTG GTG GAA CAA GTT     603
        V   G   L   K   S   D   L   Y   E   A   L   E   H   L   H   I   F   K   L   V   E   Q   V

604  CAG CAG AAT CCT TGG CCA AGC GTC GTC TGG GGG CAT TTG GGG ATA CAC GCC ATA TGC TCA GCA CGA     663
        Q   Q   N   P   W   P   S   V   V   W   G   H   L   G   I   H   A   I   C   S   A   R

664  TTG AAA GAA AAT ATC GAT GAA GTA TTT GAA ACT GCC ATA CAC TTA CTT TCC GAT TCA     723
        L   K   E   N   I   D   E   V   F   E   T   A   I   H   L   L   S   D   S

724  TTA TAT GCT CCC AGA GAG CCT ACA CAT CAT ACA ATC AAA AAT CCC TTT AAA AGA AAT ACC ACC     783
        L   Y   A   P   R   E   P   T   H   H   T   I   K   N   P   F   K   R   N   T   T
```

FIG. 2B

```
784  AGT CAG TAT CGA TTC TAC TGG AGA TAC CAG CGT CTC TAT TTC CGG AAC GAA AAG ATT
      S   Q   Y   R   F   Y   W   R   Y   Q   R   L   Y   F   R   N   E   K   I
844  AAG AAA CAA GTG TAT TAT AAT GTA AGA ATA ATG AAA ATA AAG TTC ATT CTG TTT CCC ATT      843
      K   K   Q   V   Y   Y   N   V   R   I   M   K   I   K   F   I   L   F   P   I      903
904  CTG TAC GCA CTT ACA ACA TTT AAG TGG GAA CAA TGG CAA GAA ATA CAC ACA TAC GAA CAG      963
      L   Y   A   L   T   T   F   K   W   E   Q   W   Q   E   I   H   T   Y   E   Q
964  TTT GAA TTT TCT TTT TTT TTC GAA AAT TCA GAC AAT ATC AAG TGC ATG TTT AAA GCT TAT     1023
      F   E   F   S   F   F   F   E   N   S   D   N   I   K   C   M   F   K   A   Y
1024 CTC ATC TCA TCG ATA TTT AAA CGC TGG AGT TTT ATC ACA GCT ACA CGT TGG AAG ACC GTA     1083
      L   I   S   S   I   F   K   R   W   S   F   I   T   A   T   R   W   K   T   V
1084 CAG AAG TCT ATA TTT AAA GCT AGG ACT TCA CCT AAA AAG TGC AGA AAC TTT GTC AAG CAT CAT  1143
      Q   K   S   I   F   K   A   R   T   S   P   K   K   C   R   N   F   V   K   H   H
1144 TAT AAA CTA ATC AGC ATG ACC ATG TCA GGA AGT GCC TAT CAG GAA ATG GTA CCA CCA ACA AAA AAG  1203
      Y   K   L   I   S   M   T   M   S   G   S   A   Y   Q   E   M   V   P   P   T   K
1204 ACC GTT GAC AAC AAA AGG CTT TCG TCA CCT TTG AAG TCT GGT AAC ACT TCT CGG ATC AAG    1263
      T   V   D   N   K   R   L   S   S   P   L   K   S   G   N   T   S   R   I   K
1264 AAG CCA AAG TTG AGA AAG TAC AAA GCC TTA GAT AAG GAT TCC ACA CCT CCG ATG CAG GTT GTC  1323
      K   P   K   L   R   K   Y   K   A   L   D   K   D   S   T   P   P   M   Q   V   V
1324 CTA GAA TTT GAA GTG AAC GAT CTA ATT CTA AAT GTT CAA TCT AAA ATC GTC TTA CAA     1383
      L   E   F   E   V   N   D   L   I   L   N   V   Q   S   K   I   V   L   Q
1384 AAC GAT GTT ACT TCA ATT AAA ATG TCA AGG TCT TAG AAA CAG AGA AGC CCT ATG TGG    1443
      N   D   V   T   S   I   K   M   S   R   S   -   K   Q   R   S   P   M   W
1444 TAT CAC CGA GAG TAA                                                                1503
      Y   H   R   E   -
1504 CTT TGA TCG ATA ATC CTG TTG ATA ATC CTG TTG ATA AAA CAG AAG AGA TTT GCC            1563
1564 TGC CCG GTG ATG TAG TAG TCT CAA TGA AGT AGT CTT TTA AGA ATG TAC CGT AGA GTG        1623
1624 ATT TAT ACG TAG ACG TAG AAA AAT CTC AAT CCT ACA TAG CTT ACG GAG ATG TTA AAT        1683
1684 ATT TCG GGA AAT CTT CAG GAA GTC ATG AGT TCT TCC CTT TAC CAT TAC ACC TAG AAT        1743
1744 TGA AAA GAA AAA CAA TTA ACA TTA TGA ATG CCA CAT TAC AGT TGT TAG GGT TTG AAA        1823
1824 AAC TTT TAC CCC CAT TTG ACA CCG CAA TTA GCT TTG GCT TAG GCT ACA GGA CCA            1883
1884 AAA TTA CGC CTC ATT TCG AAA AAA TCA TGC CAA ACC GAG AAA AGA TAT CAG TAA GGC CTC    1923
1924 CTT TAG ATT TGG TCA AAA GGG TAG TGA ATG GCT TGA AAC TTT GGA TCT CAA CAA AGG CGG    1983
1984 ACA GAA TTC GAT ATT AGA TAT ATT CGA TGT GCT GTT TAA AGT TCT AAA AAC AGG CGC AGG    2043
2044 ATT GAC TAA TGA AAG AAG GCA TAC TGA CTA CAA CAA TTC CAA CGC GAC           2103
2104 TAT TTT ACT GAG AGA GAA TAC CAC TAT TTT AGA CCC TTC CAA ACC AAC TTT AGA ACA GTT   2163
```

FIG. 3

```
YNUCR   51  SLSTIPSYEQ MKRTNKLPDY HLKIVVVGDG AVGKTCLLIS YVQGTFPTDY
                           ::          :  :::::::::  :    ::  ::
HUMRHO   1             MAAI RKKLVVVGDG ACGKTCLLIV FSKDEFPEVY

YNUCR  101  IPTIFENYVT NIEGPNGQII ELALWDTAGQ EEYSRLRPLS YTNADVLMVC
            ::::::::::  ::   :  .  ::::::::::  :: :::::: :::: ::: :
HUMRHO  35  VPTVFENYVA DIE-VDGKQV ELALWDTAGQ EDYDRLRPLS YPDTDVILMC

YNUCR  151  YSVGSKTSLK NVEDLWFPEV KHFCPSTPIM LVGLKSDLYE ADNLSDLVEQ
             ::  ::      ::  : ::  :::::  ::   :::  :: .          :
HUMRHO  85  FSVDSPDSLE NIPEKWVPEV KHFCPNVPII LVANKKDLRS DEHVRTELAR

YNUCR  201  VQQNPWPSVW GHLHIFKCSA RLKENIDEVF ETAIHTLLSD SLYAPREPTH
              :: :  :     :::  :
HUMRHO 135  MKQEPVRTDD GRAMAVRIQA YDYLECSAKT KEGVREVFET ATRAALQKRY

YNUCR  251  TIKNPFKRNT TSQYRFFYWR YQRLYFRNEK IKKKQVYYNV RIMMKIILLP

HUMRHO 185  GSQNGCINCC KVLX
```

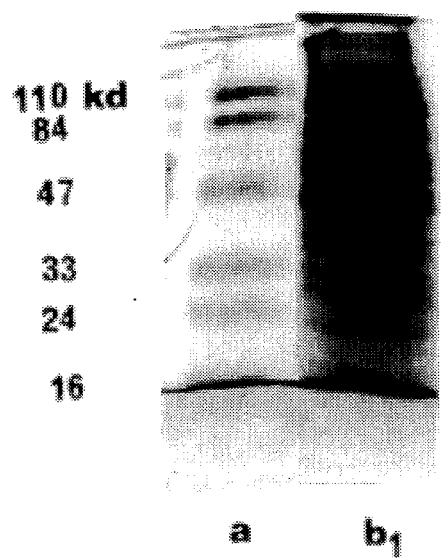 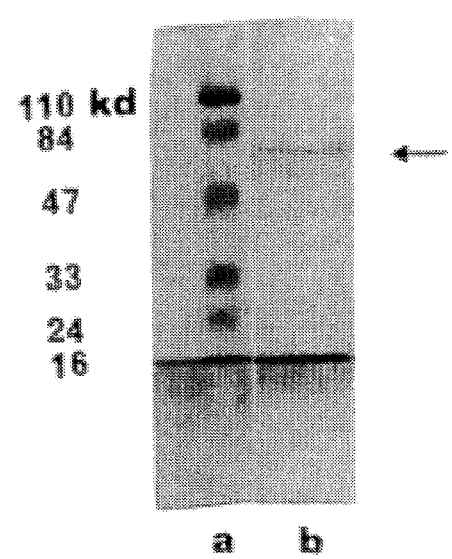

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
  ( A ) LENGTH: 238 base pairs
  ( B ) TYPE: nucleic acid
  ( C ) STRANDEDNESS: double
  ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| CCCGTTTTAT | TATAAACAG | TGAGAGGTGA | ACGATGCGTA | ATGTGTGTAT | TGCCGTTGCT | 60 |
| GTCTTTGCCG | CACTTGGCTG | ACAGTCACTC | CGGCCCGTGC | GGAAGGTGGA | CATGGTACGT | 120 |
| TTACGGTGGG | CTATTTTCAA | GTGAAACCGG | GTACATTGCC | GTCGTTGTCG | GGCGGGGATA | 180 |
| CCGGTGTGAG | TCATCTGAAA | GGGATTAACG | TGAAGTACCG | TTATGAGCTG | ACGGACAG | 238 |

( 2 ) INFORMATION FOR SEQ ID NO:2:

( i ) SEQUENCE CHARACTERISTICS:
  ( A ) LENGTH: 28 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:2:

Met Ser Thr Phe Arg Thr Gly Arg Ser Asp Cys Gln Pro Ser Ala Ala
 1               5                  10                  15

Lys Thr Ala Thr Ala Ile His Thr Leu Arg Ile Val
             20              25

( 2 ) INFORMATION FOR SEQ ID NO:3:

( i ) SEQUENCE CHARACTERISTICS:
  ( A ) LENGTH: 223 base pairs ( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

| | | | | | | |
|---|---|---|---|---|---|---|
| TATTATTTTT | GACACCAGAC | CAACTGGTAA | TGGTAGCGAC | CGGCGCTCAG | CTCCAATTCC | 60 |
| GCCGATACTG | ACGGGCTCCA | GGAGTCGTCG | CCACCACAAT | AATAATAACC | GGGCAGGCCA | 120 |
| TGTCTGCGCT | ATTTCGCGTA | AGGAAATCCA | TTGTACTGCC | GGACCACCGA | CTGTGAGCCA | 180 |
| CTCCGGCCAT | GGCGTACCAC | TGACCTGCTT | ACTGATTTGT | AAA | | 223 |

( 2 ) INFORMATION FOR SEQ ID NO:4:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:4:

Ile His Cys Thr Ala Gly Pro Pro Thr Val Ser His Ser Gly His Gly
1               5                   10                  15

Val Pro Leu Thr Cys Leu Leu Ile Cys Lys
            20                  25

( 2 ) INFORMATION FOR SEQ ID NO:5:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:5:

Val Pro Leu Thr Cys Leu Leu Ile
1               5

( 2 ) INFORMATION FOR SEQ ID NO:6:

( i ) SEQUENCE CHARACTERISTICS:
( A ) LENGTH: 2282 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 120..1574

( x i ) SEQUENCE DESCRIPTION: SEQ ID NO:6:

```
TGATTAAGTA GTTATAGCCT TACGTTAAGA CGACAAAAGA CCATGATAAG CATCCCTCAA        60

AAGTTACAGC AAACTTAAGT CAAATAGGTC ACAAAAATCT CCAATAGTAA CGCTTTTTC        119

ATG  AAT  ACA  CTA  TTA  TTT  AAG  CGA  AAA  GGT  GGC  AAT  TGT  GGG  AAC  GAA       167
Met  Asn  Thr  Leu  Leu  Phe  Lys  Arg  Lys  Gly  Gly  Asn  Cys  Gly  Asn  Glu
  1             5                          10                         15

AGT  AAC  ATA  GTT  TCG  CAG  GGA  TCG  CCC  TCA  AGT  AGC  AAT  CTT  CCT  GAA       215
Ser  Asn  Ile  Val  Ser  Gln  Gly  Ser  Pro  Ser  Ser  Ser  Asn  Leu  Pro  Glu
                    20                      25                     30

TCA  CCT  GGC  ACT  TTA  GAT  GAA  AAG  AAT  CTC  CAG  ATT  GCC  TAC  TCA  TTC       263
Ser  Pro  Gly  Thr  Leu  Asp  Glu  Lys  Asn  Leu  Gln  Ile  Ala  Tyr  Ser  Phe
               35                      40                 45

GCT  AGA  AGC  CTT  TCT  ACC  ATT  CCT  AGT  TAT  GAG  CAG  ATG  AAA  CGT  ACA       311
Ala  Arg  Ser  Leu  Ser  Thr  Ile  Pro  Ser  Tyr  Glu  Gln  Met  Lys  Arg  Thr
          50                       55                      60

AAC  AAA  CTG  CCA  GAT  TAT  CAC  CTA  AAG  ATT  GTT  GTT  GTG  GGA  GAT  GGC       359
Asn  Lys  Leu  Pro  Asp  Tyr  His  Leu  Lys  Ile  Val  Val  Val  Gly  Asp  Gly
 65                            70                      75                    80

GCT  GTA  GGG  AAG  ACG  TGC  CTG  CTG  ATA  TCT  TAT  GTC  CAA  GGA  ACA  TTT       407
Ala  Val  Gly  Lys  Thr  Cys  Leu  Leu  Ile  Ser  Tyr  Val  Gln  Gly  Thr  Phe
                         85                      90                     95

CCG  ACT  GAT  TAT  ATT  CCT  ACT  ATT  TTC  GAA  AAT  TAT  GTC  ACA  AAC  ATA       455
Pro  Thr  Asp  Tyr  Ile  Pro  Thr  Ile  Phe  Glu  Asn  Tyr  Val  Thr  Asn  Ile
               100                     105                    110

GAA  GGA  CCC  AAC  GGT  CAA  ATT  ATA  GAA  TTG  GCA  TTA  TGG  GAC  ACT  GCC       503
Glu  Gly  Pro  Asn  Gly  Gln  Ile  Ile  Glu  Leu  Ala  Leu  Trp  Asp  Thr  Ala
          115                      120                     125

GGC  CAA  GAA  GAG  TAT  AGT  AGA  CTT  AGA  CCG  CTT  TCA  TAT  AGG  AAT  GCA       551
Gly  Gln  Glu  Glu  Tyr  Ser  Arg  Leu  Arg  Pro  Leu  Ser  Tyr  Arg  Asn  Ala
     130                      135                    140

GAT  GTG  CTG  ATG  GTG  TGC  TAT  TCT  GTT  GGT  AGT  AAG  ACA  TCG  CTT  AAA       599
Asp  Val  Leu  Met  Val  Cys  Tyr  Ser  Val  Gly  Ser  Lys  Thr  Ser  Leu  Lys
145                      150                     155                    160

AAT  GTG  GAA  GAT  CTC  TGG  TTC  CCA  GAG  GTT  AAG  CAT  TTT  TGT  CCT  TCC       647
Asn  Val  Glu  Asp  Leu  Trp  Phe  Pro  Glu  Val  Lys  His  Phe  Cys  Pro  Ser
                    165                     170                    175

ACT  CCA  ATC  ATG  CTA  GTC  GGC  CTT  AAA  TCA  GAT  CTA  TAT  GAA  GCT  GAT       695
Thr  Pro  Ile  Met  Leu  Val  Gly  Leu  Lys  Ser  Asp  Leu  Tyr  Glu  Ala  Asp
               180                     185                    190

AAC  CTT  TCA  GAT  CTG  GTG  GAA  CAA  GTT  CAG  CAG  AAT  CCT  TGG  CCA  AGC       743
Asn  Leu  Ser  Asp  Leu  Val  Glu  Gln  Val  Gln  Gln  Asn  Pro  Trp  Pro  Ser
          195                     200                     205

GTC  TGG  GGG  CAT  TTG  CAC  ATA  TTC  AAG  TGC  TCA  GCA  CGA  TTG  AAA  GAA       791
Val  Trp  Gly  His  Leu  His  Ile  Phe  Lys  Cys  Ser  Ala  Arg  Leu  Lys  Glu
     210                     215                     220

AAT  ATC  GAT  GAA  GTA  TTT  GAA  ACT  GCC  ATA  CAC  ACG  TTA  CTT  TCC  GAT       839
Asn  Ile  Asp  Glu  Val  Phe  Glu  Thr  Ala  Ile  His  Thr  Leu  Leu  Ser  Asp
225                      230                     235                    240

TCA  TTA  TAT  GCT  CCC  AGA  GAG  CCT  ACA  CAT  ACA  ATC  AAA  AAT  CCC  TTT       887
Ser  Leu  Tyr  Ala  Pro  Arg  Glu  Pro  Thr  His  Thr  Ile  Lys  Asn  Pro  Phe
               245                     250                    255

AAA  AGA  AAT  ACC  ACC  AGT  CAG  TAT  CGA  TTC  TTC  TAC  TGG  AGA  TAC  CAG       935
Lys  Arg  Asn  Thr  Thr  Ser  Gln  Tyr  Arg  Phe  Phe  Tyr  Trp  Arg  Tyr  Gln
               260                     265                    270
```

```
CGT CTC TAT TTC CGG AAC GAA AAG ATT AAG AAA AAA CAA GTG TAT TAT         983
Arg Leu Tyr Phe Arg Asn Glu Lys Ile Lys Lys Lys Gln Val Tyr Tyr
        275                 280                 285

AAT GTA AGA ATA ATG ATG AAG ATT ATT CTG TTG CCC ATT CTG TAC GCA        1031
Asn Val Arg Ile Met Met Lys Ile Ile Leu Leu Pro Ile Leu Tyr Ala
        290                 295                 300

CTT ACA ACA TTT GAA AAG TGG CAA GAA AAA ATA CAC ACA TTT TAC GAA        1079
Leu Thr Thr Phe Glu Lys Trp Gln Glu Lys Ile His Thr Phe Tyr Glu
305                 310                 315                 320

CAG TTT GAA TTT TCT TTT TTT TTC TTC GAA AAT TCA GAC AAT AAG GTT        1127
Gln Phe Glu Phe Ser Phe Phe Phe Phe Glu Asn Ser Asp Asn Lys Val
                    325                 330                 335

AAA TAT AAA GCT TAT CTC ATC TCA TCG ATA AAA CGC TGG AGT ATT ATC        1175
Lys Tyr Lys Ala Tyr Leu Ile Ser Ser Ile Lys Arg Trp Ser Ile Ile
                340                 345                 350

ACA TGC ATG CGT TGC TTT TGG ACC GTA CAG AAG TCT ATA TTT AAA GCT        1223
Thr Cys Met Arg Cys Phe Trp Thr Val Gln Lys Ser Ile Phe Lys Ala
            355                 360                 365

AGG TTT TTC GCT TGC AGA AAC TTT GTC AAG AAG CAT AAT TAT AAA CTA        1271
Arg Phe Phe Ala Cys Arg Asn Phe Val Lys Lys His Asn Tyr Lys Leu
        370                 375                 380

ATC AGC ACC ATG ACT GGA AGT ACT GAA ATG GTA CCA CCA ACA ATG AAA        1319
Ile Ser Thr Met Thr Gly Ser Thr Glu Met Val Pro Pro Thr Met Lys
385                 390                 395                 400

CAT ACC GTT GAC AAC AAA AGG CTT TCG TCA CCT TTG ACA GAT TCT GGT        1367
His Thr Val Asp Asn Lys Arg Leu Ser Ser Pro Leu Thr Asp Ser Gly
                405                 410                 415

AAC CGC CGG ACT AAG AAG CCA AAG TTG AGA AAG TAC AAG GCC AAA AAG        1415
Asn Arg Arg Thr Lys Lys Pro Lys Leu Arg Lys Tyr Lys Ala Lys Lys
                420                 425                 430

GTT GAA ACA ACT TCT CCG ATG GGT GTC CTA GAA TTT GAA GTG AAC GAT        1463
Val Glu Thr Thr Ser Pro Met Gly Val Leu Glu Phe Glu Val Asn Asp
        435                 440                 445

TTG TTA AAA TCT CAA AAT TTG TCC AGG GAG CAG GTT CTG AAC GAT GTT        1511
Leu Leu Lys Ser Gln Asn Leu Ser Arg Glu Gln Val Leu Asn Asp Val
450                 455                 460

ACT TCA ATT CTA AAT GAT AAG TCC TCA ACA GAT GGA CCT ATC GTC TTA        1559
Thr Ser Ile Leu Asn Asp Lys Ser Ser Thr Asp Gly Pro Ile Val Leu
465                 470                 475                 480

CAA TAT CAC CGA GAG TAAAAAATGT CAAGGTCTTA GAAATTACTT CCAATGGCAA        1614
Gln Tyr His Arg Glu
                485

CGGGTTGGCT TTGATCGATA ATCCTGTTGA ACAGAAAAG AAGCAAGTTG TTATCATACC       1674

GTTTGGCCTG CCCGGTGATG TAGTTAATAT CAAAGTCTTT AAGACCCACC CTTACTATGT      1734

CGAGAGTGAT TTATTAGACG TAGTGGAAAA ATCTCCAATG AGAAGAGATG ATTTAATTAG      1794

GGATAAATAT TTCGGGAAAT CTTCAGGAAG TCAATTAGAG TTCTTAACTT ACGATGACCA      1854

ACTAGAATTG AAAAGAAAAA CAATTATGAA TGCCTACAAG TTCTTCGCAT TAAGGTTAGT      1914

TGCTGAAAAA CTTTTACCCC CATTTGACAC CACCGTAGCT TCCCCTTTAC AATTTGGCTA      1974

CAGGACCAAA ATTACGCCTC ATTTCGATAT GCCAAAAAGA AAACAAAAGG AACTATCAGT      2034

AAGGCCTCCT TTAGATTTGG TCAAAAGGGT AGACCTCAAT GGAGAAAAGA TACTTTGGAT      2094

ATCGGCGGAC ATGGTTCGAT ATTAGATATC GATGAATGTG TGCTTGCAAC TGAAGTTCTC      2154

AACAAAGGAT TGACTAATGA AGAAGAAAG TTTGAGCAAG AGTTAAAAA CTACAAAAAA        2214

GGCGCGACTA TTTTACTGAG AGAGAATACC ACTATTTTAG ACCCTTCCAA ACCAACTTTA      2274

GAACAGTT                                                               2282
```

( 2 ) INFORMATION FOR SEQ ID NO:7:

( i ) SEQUENCE CHARACTERISTICS:
        ( A ) LENGTH: 485 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Asn Thr Leu Leu Phe Lys Arg Lys Gly Gly Asn Cys Gly Asn Glu
 1               5                  10                  15

Ser Asn Ile Val Ser Gln Gly Ser Pro Ser Ser Ser Asn Leu Pro Glu
             20                  25                  30

Ser Pro Gly Thr Leu Asp Glu Lys Asn Leu Gln Ile Ala Tyr Ser Phe
             35                  40                  45

Ala Arg Ser Leu Ser Thr Ile Pro Ser Tyr Glu Gln Met Lys Arg Thr
         50                  55                  60

Asn Lys Leu Pro Asp Tyr His Leu Lys Ile Val Val Val Gly Asp Gly
 65                  70                  75                  80

Ala Val Gly Lys Thr Cys Leu Leu Ile Ser Tyr Val Gln Gly Thr Phe
                 85                  90                  95

Pro Thr Asp Tyr Ile Pro Thr Ile Phe Glu Asn Tyr Val Thr Asn Ile
             100                 105                 110

Glu Gly Pro Asn Gly Gln Ile Ile Glu Leu Ala Leu Trp Asp Thr Ala
             115                 120                 125

Gly Gln Glu Glu Tyr Ser Arg Leu Arg Pro Leu Ser Tyr Arg Asn Ala
         130                 135                 140

Asp Val Leu Met Val Cys Tyr Ser Val Gly Ser Lys Thr Ser Leu Lys
145                 150                 155                 160

Asn Val Glu Asp Leu Trp Phe Pro Glu Val Lys His Phe Cys Pro Ser
                 165                 170                 175

Thr Pro Ile Met Leu Val Gly Leu Lys Ser Asp Leu Tyr Glu Ala Asp
             180                 185                 190

Asn Leu Ser Asp Leu Val Glu Gln Val Gln Gln Asn Pro Trp Pro Ser
         195                 200                 205

Val Trp Gly His Leu His Ile Phe Lys Cys Ser Ala Arg Leu Lys Glu
210                 215                 220

Asn Ile Asp Glu Val Phe Glu Thr Ala Ile His Thr Leu Leu Ser Asp
225                 230                 235                 240

Ser Leu Tyr Ala Pro Arg Glu Pro Thr His Thr Ile Lys Asn Pro Phe
                 245                 250                 255

Lys Arg Asn Thr Thr Ser Gln Tyr Arg Phe Phe Tyr Trp Arg Tyr Gln
             260                 265                 270

Arg Leu Tyr Phe Arg Asn Glu Lys Ile Lys Lys Lys Gln Val Tyr Tyr
         275                 280                 285

Asn Val Arg Ile Met Met Lys Ile Ile Leu Leu Pro Ile Leu Tyr Ala
290                 295                 300

Leu Thr Thr Phe Glu Lys Trp Gln Glu Lys Ile His Thr Phe Tyr Glu
305                 310                 315                 320

Gln Phe Glu Phe Ser Phe Phe Phe Phe Glu Asn Ser Asp Asn Lys Val
                 325                 330                 335

Lys Tyr Lys Ala Tyr Leu Ile Ser Ser Ile Lys Arg Trp Ser Ile Ile
             340                 345                 350

Thr Cys Met Arg Cys Phe Trp Thr Val Gln Lys Ser Ile Phe Lys Ala
         355                 360                 365
```

```
Arg  Phe  Phe  Ala  Cys  Arg  Asn  Phe  Val  Lys  Lys  His  Asn  Tyr  Lys  Leu
     370                 375                 380

Ile  Ser  Thr  Met  Thr  Gly  Ser  Thr  Glu  Met  Val  Pro  Pro  Thr  Met  Lys
385                      390                 395                           400

His  Thr  Val  Asp  Asn  Lys  Arg  Leu  Ser  Ser  Pro  Leu  Thr  Asp  Ser  Gly
                    405                      410                 415

Asn  Arg  Arg  Thr  Lys  Lys  Pro  Lys  Leu  Arg  Lys  Tyr  Lys  Ala  Lys  Lys
               420                      425                      430

Val  Glu  Thr  Thr  Ser  Pro  Met  Gly  Val  Leu  Glu  Phe  Glu  Val  Asn  Asp
          435                 440                      445

Leu  Leu  Lys  Ser  Gln  Asn  Leu  Ser  Arg  Glu  Gln  Val  Leu  Asn  Asp  Val
     450                 455                      460

Thr  Ser  Ile  Leu  Asn  Asp  Lys  Ser  Ser  Thr  Asp  Gly  Pro  Ile  Val  Leu
465                      470                 475                           480

Gln  Tyr  His  Arg  Glu
                    485
```

(2) INFORMATION FOR SEQ ID NO:8:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:8:

```
Met  Ala  Ala  Ile  Arg  Lys  Lys  Leu  Val  Val  Gly  Asp  Gly  Ala  Cys
1                   5                   10                      15

Gly  Lys  Thr  Cys  Leu  Leu  Ile  Val  Phe  Ser  Lys  Asp  Glu  Phe  Pro  Glu
               20                  25                      30

Val  Tyr  Val  Pro  Thr  Val  Phe  Glu  Asn  Tyr  Val  Ala  Asp  Ile  Glu  Val
          35                  40                      45

Asp  Gly  Lys  Gln  Val  Glu  Leu  Ala  Leu  Trp  Asp  Thr  Ala  Gly  Gln  Glu
     50                       55                  60

Asp  Tyr  Asp  Arg  Leu  Arg  Pro  Leu  Ser  Tyr  Pro  Asp  Thr  Asp  Val  Ile
65                       70                  75                            80

Leu  Met  Cys  Phe  Ser  Val  Asp  Ser  Pro  Asp  Ser  Leu  Glu  Asn  Ile  Pro
               85                       90                       95

Glu  Lys  Trp  Val  Pro  Glu  Val  Lys  His  Phe  Cys  Pro  Asn  Val  Pro  Ile
               100                      105                      110

Ile  Leu  Val  Ala  Asn  Lys  Lys  Asp  Leu  Arg  Ser  Asp  Glu  His  Val  Arg
               115                      120                      125

Thr  Glu  Leu  Ala  Arg  Met  Lys  Gln  Glu  Pro  Val  Arg  Thr  Asp  Asp  Gly
          130                      135                      140

Arg  Ala  Met  Ala  Val  Arg  Ile  Gln  Ala  Tyr  Asp  Tyr  Leu  Glu  Cys  Ser
145                      150                      155                      160

Ala  Lys  Thr  Lys  Glu  Gly  Val  Arg  Glu  Val  Phe  Glu  Thr  Ala  Thr  Arg
               165                      170                      175

Ala  Ala  Leu  Gln  Lys  Arg  Tyr  Gly  Ser  Gln  Asn  Gly  Cys  Ile  Asn  Cys
               180                      185                      190
```

Cys Lys Val Leu Xaa
195

( 2 ) INFORMATION FOR SEQ ID NO:9:

( i ) SEQUENCE CHARACTERISTICS:
        ( A ) LENGTH: 250 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:9:

```
Ser  Leu  Ser  Thr  Ile  Pro  Ser  Tyr  Glu  Gln  Met  Lys  Arg  Thr  Asn  Lys
1                   5                        10                       15

Leu  Pro  Asp  Tyr  His  Leu  Lys  Ile  Val  Val  Val  Gly  Asp  Gly  Ala  Val
               20                        25                       30

Gly  Lys  Thr  Cys  Leu  Leu  Ile  Ser  Tyr  Val  Gln  Gly  Thr  Phe  Pro  Thr
          35                        40                       45

Asp  Tyr  Ile  Pro  Thr  Ile  Phe  Glu  Asn  Tyr  Val  Thr  Asn  Ile  Glu  Gly
     50                        55                       60

Pro  Asn  Gly  Gln  Ile  Ile  Glu  Leu  Ala  Leu  Trp  Asp  Thr  Ala  Gly  Gln
65                       70                       75                       80

Glu  Glu  Tyr  Ser  Arg  Leu  Arg  Pro  Leu  Ser  Tyr  Thr  Asn  Ala  Asp  Val
               85                        90                       95

Leu  Met  Val  Cys  Tyr  Ser  Val  Gly  Ser  Lys  Thr  Ser  Leu  Lys  Asn  Val
               100                       105                      110

Glu  Asp  Leu  Trp  Phe  Pro  Glu  Val  Lys  His  Phe  Cys  Pro  Ser  Thr  Pro
          115                       120                      125

Ile  Met  Leu  Val  Gly  Leu  Lys  Ser  Asp  Leu  Tyr  Glu  Ala  Asp  Asn  Leu
     130                       135                      140

Ser  Asp  Leu  Val  Glu  Gln  Val  Gln  Gln  Asn  Pro  Trp  Pro  Ser  Val  Trp
145                       150                      155                      160

Gly  His  Leu  His  Ile  Phe  Lys  Cys  Ser  Ala  Arg  Leu  Lys  Glu  Asn  Ile
               165                       170                      175

Asp  Glu  Val  Phe  Glu  Thr  Ala  Ile  His  Thr  Leu  Leu  Ser  Asp  Ser  Leu
          180                       185                      190

Tyr  Ala  Pro  Arg  Glu  Pro  Thr  His  Thr  Ile  Lys  Asn  Pro  Phe  Lys  Arg
     195                            200                      205

Asn  Thr  Thr  Ser  Gln  Tyr  Arg  Phe  Phe  Tyr  Trp  Arg  Tyr  Gln  Arg  Leu
     210                       215                      220

Tyr  Phe  Arg  Asn  Glu  Lys  Ile  Lys  Lys  Lys  Gln  Val  Tyr  Tyr  Asn  Val
225                       230                      235                      240

Arg  Ile  Met  Met  Lys  Ile  Ile  Leu  Leu  Pro
               245                      250
```

CHIMERIC PROTEIN THAT HAS A HUMAN RHO MOTIF AND DEOXYRIBONUCLEASE ACTIVITY

RELATED APPLICATION

This application is a continuation-in-part of U.S. application Ser. No. 07/674,801, filed Mar. 26, 1991, now abandoned. The disclosure of this previous application is incorporated herein in its entirety by reference thereto.

FIELD OF THE INVENTION

The present invention relates, in general, to biological molecules corresponding to endo-exonucleases. In particular, the present invention relates to DNA segments, polypeptides, antibodies, host cells and methods of producing and using the foregoing related to endo-exonucleases.

BACKGROUND OF THE INVENTION

Repair processes in the yeast *Saccharomyces cerevisiae* are under extensive genetic control involving over 50 genes; among these are genes that function in recombinational repair, as well as normal meiotic and mitotic recombination. (Kunz, B. A., and R. H. Haynes *Annu. Rev. Genet.* 15:57–89 (1981); Game, J. C. (1983) in: Yeast Genetics, Fundamental and Applied Aspects (eds. Spencer, J. F. T., Spencer, D., and Smith, A.), pgs. 109–137, Springer-Verlag New York, Inc., New York; and Resnick, M. A. in: *Meiosis* (Ed. Moens, P.), pgs. 157–212 (1987), Academic Press, New York). Deoxyribonucleases are expected to play a role in many repair processes since they enable the excision of damaged DNA and provide a means for heteroduplex formation and processing in recombination. Several deoxyribonucleases have been shown, both genetically and biochemically, to function in recombination and repair. For example, the nuclease activity associated with the *Escherichia coli* recBCD proteins is required for much of host recombination and also for the chi-stimulated lambda bacteriophage (Chaudhury, A. M., and G. R. Smith, *Proc. Natl. Acad. Sci.* (USA) 81:7850–7854 (1984)). Holloman and Holliday (*J. Biol. Chem.* 240:8107–8113, (1973)) have described nuclease α from the eukaryote *Ustilago maydis* that is required for recombination and DNA repair. Because of a complex genetic control mechanism, involving two genes, the specific role of this nuclease has not been ascertained.

An endo-exonuclease from *Neurospora crassa* has also been implicated in recombination and repair (Chow, T. Y.-K, and M. F. Fraser, *Can. J. Biochem.* 57:889–901 (1979); Chow, T. Y.-K, and M. F. Fraser, *J. Biol. Chem.* 258:12010–12018 (1983); and Ramotar, D., et al., *J. Biol. Chem.* 262:425–431 (1987)). The phenotypes of mutants deficient or altered in nuclease activity include meiotic sterility and sensitivity to ultraviolet light, X-rays and/or alkylating agents (Fraser, M. J., et al. in: DNA Repair and Mutagenesis in Eukaryotes (Generoso, et al., eds.), pgs. 63–74 (1990), Plenum Publishing Corp., New York). A similar endo-exonuclease has also been isolated from *Aspergillus nidulans* (Koa, H., et al., *Biochem. Cell. Biol.* 68:387–392 (1990)) and from mammalian mitochondria (Tomkinson, et al., *Nucl. Acids Res.* 14:9579–9593 (1986)).

An endo-exonuclease, RhoNUC, from *S. cerevisiae* was isolated, characterized, and suggested to function in both repair and recombination (Chow, T. Y.-K, M. A. Resnick, *J. Biol. Chem.* 262:17659–17667 (1987); and Chow, T. Y.-K, land M. A. Resnick, *Molec. Gen. Genet.* 211:41–48 (1988)). Several properties of RhoNUC resemble those of the *E. coli* recBCD nuclease. The RhoNUC activity in both mitotic and meiotic cells is greatly influenced by a functional RAD52 gene. The RAD52 gene product is required for mitotic and meitic recombination and for the repair of double stranded breaks in DNA. In rad52 mutants, the mitotic level of the endo-exonuclease is less than 10% of the wild type level, and no increase is observed during meiosis (Resnick, M. A., et al., *Molec. Cell. Biol.* 4:2811–2817 (1984)).

In the past decade, recBCD-like eukaryotic deoxyribonucleases have been discovered which act on both single-stranded DNA (endonucleolytic) and double-stranded DNA (exonucleolytic) and were thus termed endo-exonucleases. These peptides were mostly exonucleolytic with a small endonucleolytic activity.

The endo-exonucleases isolated from the various eukaryotic sources studied so far share common antigenic epitopes with the *E. coli* recBCD nuclease. Rabbit polyclonal antibody raised against the *Neurospora crassa* endo-exonuclease cross-reacts with the endo-exonucleases from other species (Fraser, M. J., Chow, T. Y.-K., Cohen, H. and Koa, H., *Biochem. Cell. Biol.*, Vol. 64, pp. 106–116 (1986); and Fraser, M. J., Koa, H. and Chow, T. Y.-K, *J. Bacteriol.*, Vol. 172, pp. 507–510 (1990)).

A new model has been proposed by Rosenberg and Hastings (Rosenberg, S. M. and Hastings, P. J., *Biochimie*, Vol. 73, pp. 385–397 (1991)) in which endo-exonuclease action is an integral part of the recombination process. Unfortunately, no one has yet been able to isolate mammalian endo-exonucleases. To prove this model it would be helpful to analyze endo-exonucleases from various species. The importance of each region of the enzyme can then be estimated depending on the amount of conservation detected in each species' peptide.

SUMMARY OF THE INVENTION

The present invention includes a variety of biological molecules related to endo-exonucleases. For example, the present invention includes DNA segments coding for a polypeptide having an amino acid sequence corresponding to RhoNUC, a polypeptide having an amino acid sequence corresponding to RhoNUC, antibodies to RhoNUC, a recombinant DNA molecule encoding RhoNUC, cells containing RhoNUC, and methods of producing and using the polypeptide and DNA segment.

The present invention also relates to mammalian endo-exonucleases. Specifically, the present invention relates to the DNA sequence and protein products corresponding to a mammalian endo-exonuclease. The present invention also relates to antibodies directed against mammalian endo-exonucleases and cell cultures containing exogenous DNA fragments encoding mammalian endo-exonucleases.

In one aspect, the present invention, provides an isolated endo-exonuclease. In one embodiment of this aspect of the invention, the endo-exonuclease is a primate endo-exonuclease, an especially preferred form of this invention is a human endo-exonuclease. In another embodiment, it is a mammalian endo-exonuclease having greater activity in the 5'→3' direction than in the 3'→5' direction. In still another embodiment, the endo-exonuclease is a mammalian endo-exonuclease having exonuclease activity on double-stranded polynucleotides and endonuclease activity on single-stranded polynucleotides. In particularly preferred forms, the endo-exonuclease includes attributes of two or more of the foregoing embodiments. Some of the endo-exonucleases of the present invention have at least one epitope in common with the *N. crassa* endo-exonuclease. Others are derived from Monkey CV-1 cells or from Monkey COS-1 cells. Some particularly preferred forms of this aspect a of the invention have at least six consecutive amino acids encoded by the opposite strand of the DNA sequence of SEQ ID NO: 1 or the coding strand of SEQ ID NO: 3, some of these have substantially the same amino acid sequence encoded by the opposite strand of the DNA sequence of SEQ ID NO: 1 or the coding strand of SEQ ID NO: 3.

The present invention also includes isolated antibodies capable of specifically binding to an endo-exonuclease as described above.

Furthermore, the present invention also includes an isolated segment of a polynucleotide having at least eighteen consecutive nucleotides encoding the same amino acid sequence in the universal genetic code as eighteen consecutive nucleotides in SEQ ID NO: 1 or in SEQ ID NO: 3, as well as polynucleotides, such as DNA, encoding an endo-exonuclease described above. In a preferred form of this DNA, the sequence is in a vector, such as λgt11.

The present invention also includes a method for detecting precancerous or cancerous conditions in a mammal. This method includes obtaining a biological sample from the mammal, determining the amount of RhoNUC or related endo-exonuclease present in the species of mammal being tested that is present in the biological sample, and comparing the determined amount of RhoNUC present in the sample with the amount of RhoNUC expected in a normal sample of the same type as the sample. In this method, an increased amount of RhoNUC or related protein present in the sample compared to a normal sample indicates a precancerous or cancerous condition in the mammal. A preferred sample would be a tissue sample suspected of having cancerous or precancerous tissue. The determining step can be performed using any of a number of assays, including IFA, immunoblot, RIA, RIST, ELISA, agglutination and hemagglutination. Thus, a particularly preferred embodiment of this invention includes contacting an antibody that specifically binds to RhoNUC or a related protein with the sample.

Another aspect of the present invention provides a method of determining whether a mammalian germ cell is capable of producing viable offspring. This method includes obtaining a sample containing at least one germ cell from the mammal, determining the amount of mammalian endo-exonuclease present in the sample, and comparing the determined amount of mammalian endo-exonuclease present in the sample with the amount of mammalian endo-exonuclease expected in a normal sample of the same type as the sample, wherein a decreased amount of mammalian endo-exonuclease present in the sample compared to a normal sample indicates a lowered likelihood that the germ cell is capable of producing viable offspring. The sample can include an ovum and can also be semen or other sample including a sperm cell. In a preferred form of this method, the determining step makes use of one of the following assays: IFA, immunoblots, RIA, RIST, ELISA, agglutination and hemagglutination. Thus, the determining step can include contacting an antibody that specifically binds to mammalian endo-exonuclease with the sample.

The present invention also includes a pharmaceutical composition for preventing UV damage to cells. This composition includes an endo-exonuclease in an amount effective to prevent UV damage to the cells, and a pharmaceutically acceptable carrier. In a preferred form, the endo-exonuclease has substantially the same activity as human endo-exonuclease. The composition can be in the form of an ointment suitable for application to mammalian skin and can also include a sunscreen ingredient, such as PABA. The present invention also includes a method of protecting cells from UV damage to mammalian cells by applying a composition of this aspect of the invention to the cells in an amount effective to prevent UV damage to the cells. The applying step can include application of the composition to the skin of the mammal prior to exposure of the skin to UV irradiation. Preferably, the composition is applied prior to exposure of the skin to sunlight.

In still a further embodiment of the present invention, there is provided a method of treating a mammal having an immunological disorder associated with a decreased ability to produce antibodies. In this method, an endo-exonuclease in an amount effective to augment production of antibodies in the mammal is administered to the mammal. The endo-exonuclease preferably has substantially the same activity as mammalian endoexonuclease. This method can be used to treat a number of disorders, including the following: congenital hypogammaglobulinemia, transient hypogammaglobulinemia of infancy, acquired hypogammaglobulinemia, selective deficiencies of IgA, IgM or IgG subclasses, secondary B-cell immunodeficiency associated with drugs or protein-losing states, B-cell immunodeficiency associated with 5'-nucleotidase deficiency or other enzyme deficiency, and X-linked lymphoproliferative disease.

In still a further embodiment of the present invention, there is provided an isolated multi-domain protein with N-terminal homology to the rho oncogene and endogenous nuclease activity. In certain embodiments, this multi-domain protein is derived from a primate, such as human, or is derived from yeast, such as *S. cerevisiae*.

The present invention provides, in yet another aspect thereof, a method for treating a patient with skin cancer. This method includes administering a pharmaceutically effective amount of an endo-exonuclease to the patient in a topical carrier, measuring the size of the skin cancer, and reapplying the mammalian endo-exonuclease to the patient until the skin cancer is diminished. The invention also includes regulating cell growth by addition of an endo-exonuclease or an agonist thereof to growing cells.

Further, the present invention includes a method for determining if an agent affects the production of antibody diversity in a mammal using an in vitro model for production of antibody diversity. This method includes the following steps: obtaining and culturing B-cell precursor cells from the mammal, dividing the resulting cell culture into a first group of cells and a second group of cells, adding an endo-exonuclease to the first group of cells in the presence of an antigen to determine a normal rate of antibody production, adding the endo-exonuclease to the second group of cells in the presence of the agent and the antigen to determine the rate of antibody production in the presence of the agent, and comparing the normal rate of antibody production to the rate of antibody production in the presence of the agent, wherein an increased rate of antibody production in the presence of the agent indicates that the agent augments the production of antibody diversity and a decreased rate of antibody production in the presence of the agent indicates that the agent retards the production of antibody diversity.

Still a further aspect of the present invention provides a method of identifying and cloning a gene for a protein from an organism of interest that interacts with a known endo-exonuclease. This method includes producing two types of plasmids encoding a hybrid protein. The first plasmid encodes a hybrid that includes a transcriptional activator protein, such as GAL4 from yeast, and an endo-exonuclease. The second type of plasmid is part of a plasmid library in which each of the second type of plasmids encodes a hybrid protein including the activation domain of the transcriptional activator protein and genomic DNA from the organism of interest. Host organisms are simultaneously transformed with at least one of the second plasmids and the first plasmid. This host organism contains a reporter gene containing a binding site for the transcriptional activator protein. In order to select clones including the desired protein, host organisms are identified in which the reporter gene is activated. In a preferred embodiment of this invention, the polypeptide encoded by the genomic DNA contained in the isolated plasmids is also isolated. Thus, the present invention includes polypeptides isolated in this method.

In yet a further aspect of the present invention, there is provided a method of enhancing a conventional method of transforming or transfecting a cell of a eukaryotic organism in which an oligonucleotide is integrated into a host cell through endogenous recombination. The enhancement includes administering to the cell an endo-exonuclease or an agonist thereof as part of the transformation or transfection procedure.

Still another aspect of the present invention is a method of augmenting a conventional anti-cancer therapy in which cells undergoing rapid replication are selectively affected. This method includes administering to the cells a pharmacologically effective amount of an endo-exonuclease or an agonist thereof.

Finally, the present invention also includes an isolated culture of cells, such as RNC1$^-$ mutant yeast cells that are incapable of producing at least one endogenous endo-exonuclease. The mutant cells of this aspect of the invention are useful in a preferred embodiment of a method, also provided by the present invention in which an endo-exonuclease from a desired organism is identified. In this method, a culture of cells from an organism deficient in endo-exonuclease activity identifiable by a mutant phenotype is grown. These cells are transformed with a cDNA expression vector library from the desired organism, and transformants are identified that have an altered phenotype in which the mutant phenotype is at least partially reversed.

DESCRIPTION OF THE DRAWINGS

FIG. 1. Restriction endonuclease map of insert from (A) λgt11 clone and from (B) YEp213-10. The location of mini-Tn10 transposon insertion in λgt11 and of LEU2 gene disruption are indicated by the inverted triangle. The open reading frame of the RNC1 gene was indicated by the arrow (a). The restriction endonuclease symbols are: R1, EcoR1; X1, XhoI; Bm1, BamH1; K1, Kpn1; H3, HindIII; SP1, Sph1; B1, BglII; and S1, Sal1.

FIG. 2. Nucleotide sequence of RNC1 (SEQ ID NO:6) and its corresponding translated amino acid sequence (SEQ ID NO:7). The five amino acids underlined correspond to the five amino acids determined by protein sequence with the purified yeast RhoNUC endo-exonuclease protein.

FIG. 3. Comparison of the amino acid sequences encoded by the human rho oncogene (HumRHO; SEQ ID NO:8) with the N-terminal amino acid sequences of RNC1(YNUCR; SEQ ID NO:9). The alignments were generated by computer as described (Devereux, J., et al., Nucl. Acids. Res. 12:387–395 (1984)). The putative GTP binding sites in rho oncogeny are underlined.

FIG. 6. Methylmethanesulfonate (MMS) survival of A: RAD$^+$ cells and RAD$^+$[YEp213-10] cells. The heavy lines correspond to stationary cells and the dashed to logarithmically growing cells: (o) no plasmid (inverted triangle) contains YEp213-10.

Tris-HCl buffer (100 mM) at various pHs (Chow, T. Y.,-K and Resnick, M. A., *J. Biol. Chem.*, Vol.262, pp. 17659–17667 (1987); Dake, E., Hofmann, T. J., McIntire, S., Hudson, A. and Zassenhaus, H. P., *J. Biol. Chem.*, Vol. 263, pp. 7691–7702 (1988); Koa, H., Fraser, M. J. and Kafer, E., *Biochem. Cell. Biol.*, Vol. 68, pp. 387–392 (1990); and Chow, T. Y.-K., Yamamoto, A., Mason, J. and Resnick, M. A., *J. Cell. Biochem.*, Vol. 10B, pp. 211 (1986)) containing 10 mM MgCl$_2$ was used in the determination.

Figure 13:
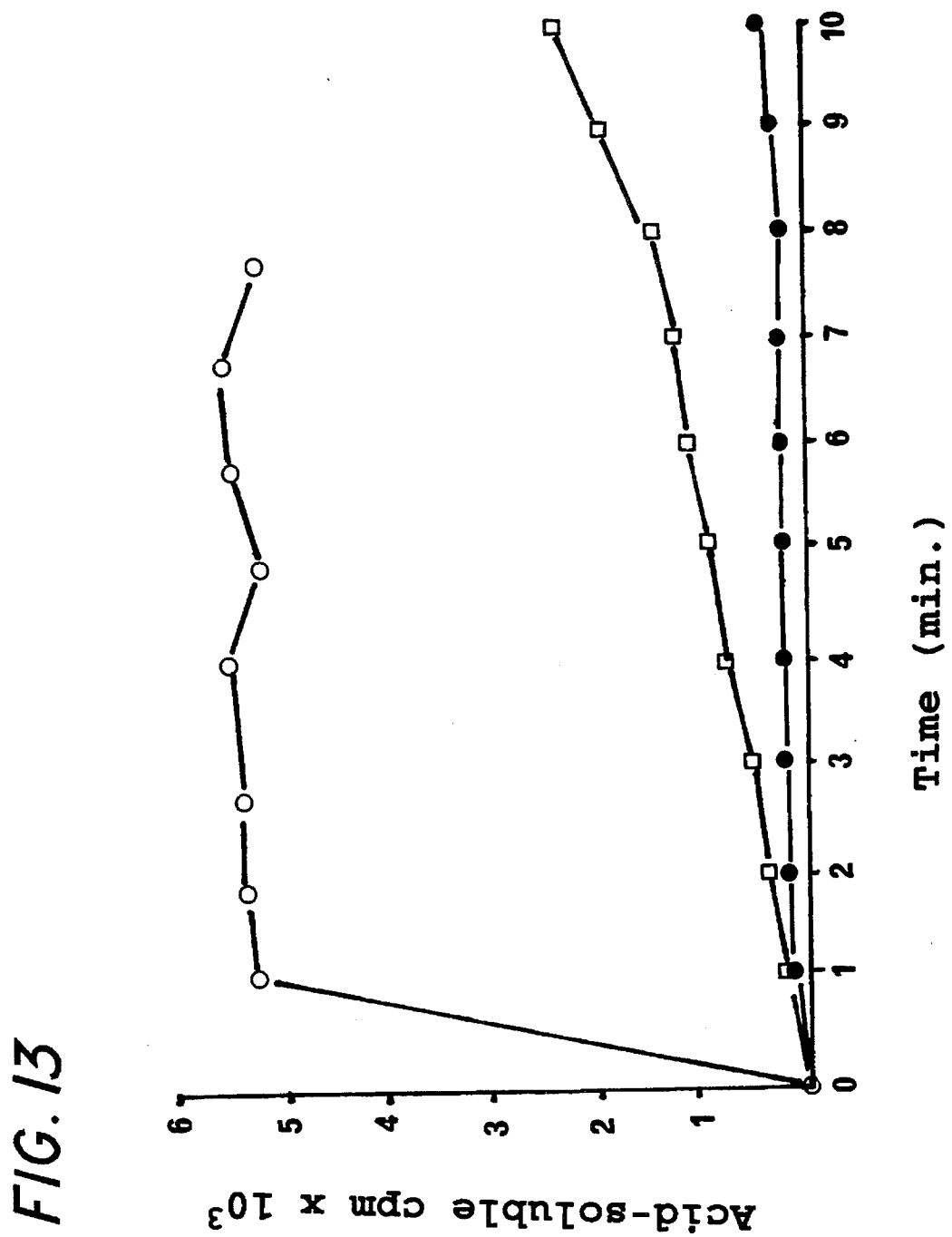

FIG. 13: Activity of mammalian endo-exonuclease on $^{32}$P-end-labeled-ds-DNA and internally $^3$H-labeled ds-DNA. The ds-DNA was labeled at the 5' termini using T4 polynucleotide kinase and at 3' termini with Klenow fragment of Polymerase I. Acid-soluble radioactivity released from 5'-$^{32}$P-end labeled ds-DNA (○), 3'-$^{32}$P-end labeled ds-DNA (●) and from internally $^3$H-labeled ds-DNA (□*).

FIG. 14: Specific binding and cleavage of a four-way DNA (Holliday) junction by the mammalian endo-exonuclease. Panel A. The binding of Holliday junction DNA by endo-exonuclease. Purified endo-exonuclease (5 units) was incubated with $^{32}$P-labeled junction molecules, linear ss-DNA (146 nucleotides) and linear ds-DNA (146 nucleotides) according to the method described by Parsons and West (*Nuc. Acids Res.* 18:4377–4384 (1990)). Complexes were resolved on low ionic strength gels and radiolabeled DNA was detected by autoradiography. The protein-DNA complexes formed between the four-way junction and the endo-exonuclease was indicated by c. The migration of the four-way junction and the ss-DNA fragment were the same and were indicated by x. The migration of the ds-DNA fragment was indicated by d. Lane a, four-way junction with 5 units of endo-exonuclease. Lane b, four-way junction only. Lane c, ss-DNA fragment with 5 units of endo-exonuclease. Lane d, ss-DNA only. Lane e, ds-DNA fragment with 5 units of endo-exonuclease. Lane f, ds-DNA only. Panel B. Cleavage of four-way junction by endo-exonuclease (2 units). Lane a, 0 min digestion. Lanes b–d, 1, 2 and 3 minutes of digestion. Lane e, 45 minutes of digestion. Lane f, 90 minutes of digestion.

Figure 15:
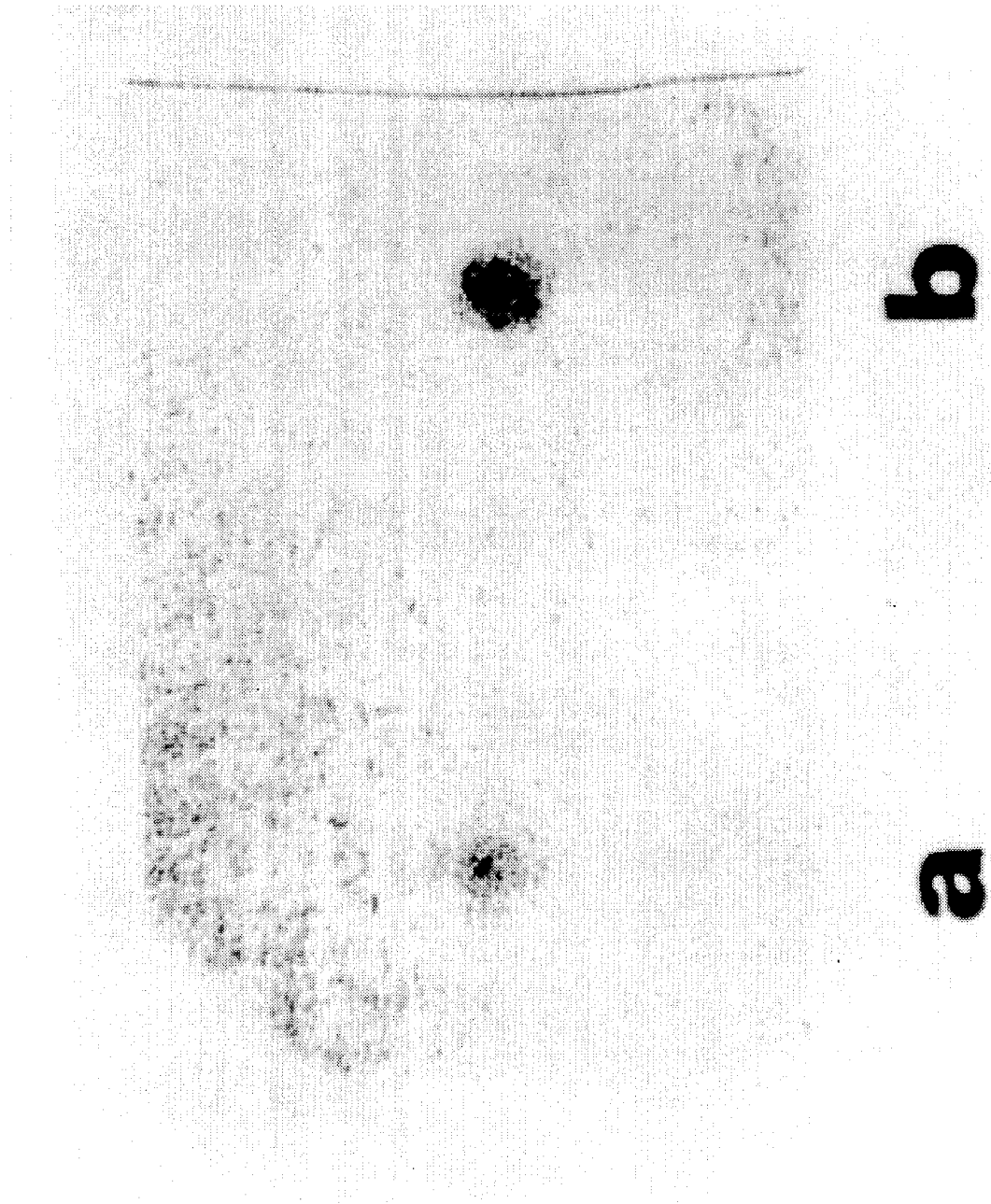

FIG. 15: Immune-crossreactive material in CV- 1 and COS- 1 cells. Equal amount of proteins (20 μg) of extracts of CV-1 and COS-1 cells were spotted onto a nitrocellulose membrane. The nitrocellulose membrane was treated with the antibody as described in Materials and Methods. a, protein extract from CV-1. b, protein extract from COS-1.

Figure 16A:
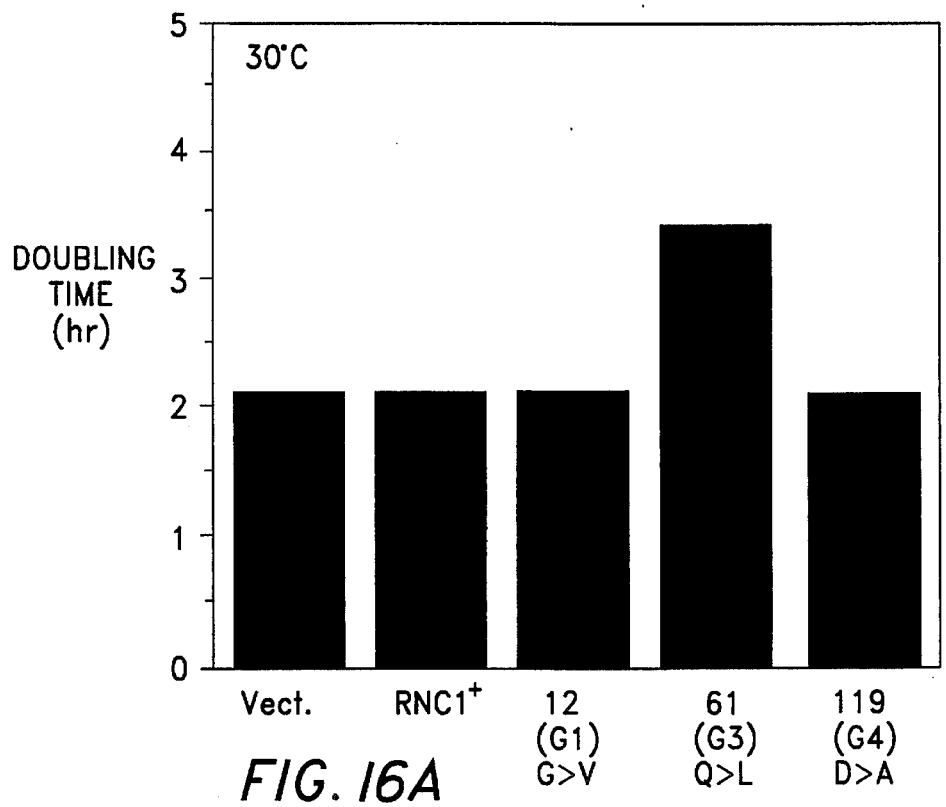
Figure 16B:
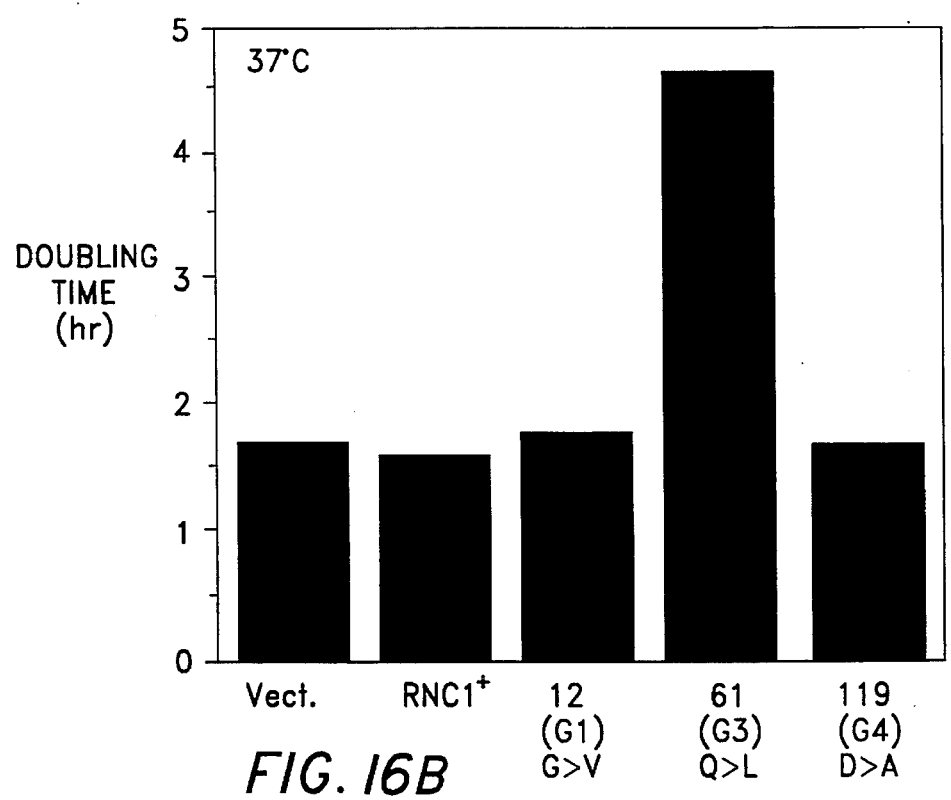

FIG. 16. Bar graph of RhoNUC GTP binding region mutants. The RhoNUC amino acid sequence was mutated in three of its GTP binding boxes and compared with growth rates of wildtype yeast cells.

Figure 17:
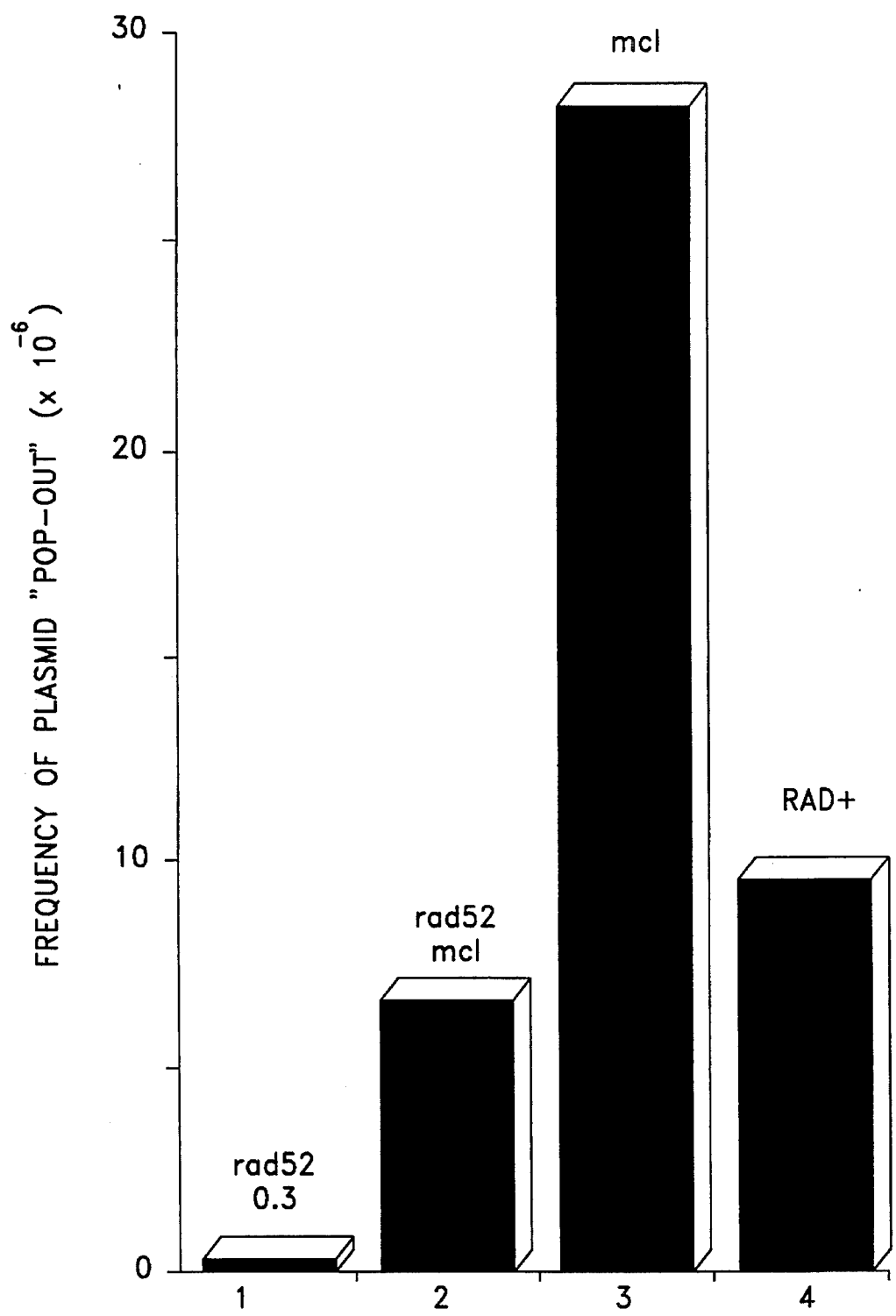

FIG. 17. Recombinational effect of rnc1 mutation on rad52 and wildtype cells. Yeast cells with a wildtype (RAD+), rad52, rad52/rnc1 and rnc/phenotype were compared based on their ability to cause a direct repeat cross-over event.

DETAILED DESCRIPTION OF THE INVENTION

I. ISOLATION AND CHARACTERIZATION OF YEAST ENDO-EXONUCLEASE

A DNA sequence corresponding to the *S. cerevisiae* endo-exonuclease (RhoNUC) was isolated from a lambda gt11 expression library. The DNA sequence was denoted RNC1 for Rho Associated Nuclease 1.

Antibodies directed against a *N. crassa* endo-exonuclease were used to probe a lambda gt11 expression library to identify those clones expressing antigenic sites which cross react with the *N. crassa* endo-exonuclease. The lambda gt11 expression library comprised cDNA clones isolated from *S. cerevisiae* mRNA. Cross-hybridizing plaques were selected for further study and thought to be expressing clones coding for a *S. cerevisiae* endo-exonuclease.

A. General Protocols and Reagents

The following protocols and experimental details are referenced in the examples that follow:

Strains and Media. The yeast strains used in this study are: TC106d with genotype of MATαleu2 ura3 his1 trp1, and TC107a with genotype of MATαleu2 ura3 his1 trp1ra TC80c has a genotype of Matαleu2 ura3 trp1, and TC105d has a genotype of Matαleu2 his1 trp1. These strains were congenic and closely related to the efficient sporulating strain SK1. The diploid strain for gene disruption was TC80c X TC105d. Media for the growth and sporulation of *S. cerevisiae*, as well as standard genetic techniques, have been described elsewhere (Methods in Yeast Genetics (ed. Sherman, et al.) Cold Spring Harbor Laboratory. Press, 1986).

The following procedure describes a method of isolating a DNA segment coding for an endo-exonuclease from a lambda gt11 expression library comprising cDNA from *S. cerevisiae*.

Previously, it was shown that an antibody raised against an endo-exonuclease from *N. crassa* cross-reacted with an endo-exonuclease of *S. cerevisiae* (Chow, T. Y.-K, and M. A. Resnick, *J. Biol. Chem.* 262:17659–17667 (1987); and Chow, T. Y.-K, and M. A. Resnick, *Molec. Gen. Genet.* 211:41–48 (1988)). This *N. crassa* antibody was used as a probe to isolate gene sequences coding from a *S. cerevisiae* endo-exonuclease from a λgt11 yeast genomic expression library.

B. Antibody Identification of RNC1 Clone

*E. coli* bacterial strain Y1090 was infected with a *S. cerevisiae* cDNA library in bacteriophage λgt11 according to the method described by Young and Davis (Young, R. A. and R. W. Davis, *Proc. Natl. Acad. Sci.* (USA) 80:1194–1198 (1983); and Young, R. A. and R. W. Davis, *Science* 222:778–782 (1984)) and subsequently plated. The cloned cDNA inserts in λgt11 were linked to a beta-galactosidase promoter, so that promoter inducement lead to expression of the cloned insert. After a five hour incubation at 37° C., the plates were overlaid with nitrocellulose filters. Each filter was previously soaked in 10 mM IPTG overnight. IPTG is a beta-galactosidase inducer and therefore caused expression of the lambda gt11 inserts.

Nitrocellulose filters, now containing the bound λgt11 expression proteins, were removed and washed once with Tris-HCl Ph 7.5 containing 1 mM EDTA and 150 mM NaCl. The filters were processed by a method similar to that of Towbin, et al. (*Proc. Natl. Acad. Sci.* (USA) 76:4350–4354 (1979)).

The filters were enclosed in boiling pouches containing 10–15 ml of buffer A (10 mM Tris-HCl,pH 8.0, 1 mM EDTA, 150 mM NaCl, 2% skim milk powder) and contacted with *N. crassa* anti-endo-exonuclease antibody for 3 hours (1:200 dilution serum per blot) with continuous agitation at room temperature (approximately 23° C.). The filters were subsequently rinsed for 45 min at room temperature with three changes of buffer A (lacking skim milk powder) to wash away unbound antibody, and thereafter resealed into boiling pouches.

Each boiling pouch, was subsequently incubated in 10–15 ml buffer A containing approximately 1 mCi/blot [$^{125}$I] protein A for 1.5 h at room temperature to allow protein A antibody complex formation.

Unbound protein A was removed from the blots with buffer A (without skim milk powder) at room temperature for 15 minutes and again for 30 minutes in buffer A containing 1 M NaCl (without skim milk powder). Finally, the filters were rinsed for 15 minutes in buffer A, dried, and exposed to Kodak XAR-5 X-ray film in Dupont intensifying screens at room temperature.

Lambda gt11 vectors expressing cross-reactive proteins were identified as $^{125}$I labeled spots on the autoradiograph. Plaques corresponding to each labeled spot were chosen for further study. Among 100,000 phages screened, one clone, containing a 3 Kb yeast cDNA insert was chosen. Restriction mapping of the 3 kb clone identified potential cleavage sites (FIG. 1A). The restriction endonuclease symbols listed in FIG. 1 are explained below:

| Code | Enzyme |
| --- | --- |
| R1 | EcoR1 |
| X1 | XhoI |
| Bm1 | BamH1 |
| K1 | Kpn1 |
| H3 | HindIII |
| SP1 | Sph1 |
| B1 | BhlII |
| S1 | Sa11 |

To ensure that the cross-reacting material identified by the positive plaques was due to expression of the lambda gt11 DNA insert, a transposable element was used to disrupt the 3 kb gene's expression. If cross-reactivity with the N. crassa endo-exonuclease antibody was no longer detected after transposon intervention, it could be assumed that the 3 kb insert encoded a protein with epitopes corresponding to an endo-exonuclease protein. The following experiment describes how to use a mini Tn10 transposable element to disrupt λgt11 gene expression.

C. Transposition Mutagenesis of λgt11-RNC1 with a Mini Tn10 Transposable Element.

Insertion mutagenesis of the coding sequences on λgt11 clones with a mini-Tn10 "transplason" was carried out according to the method described by Snyder, et al. (*Proc. Natl. Acad. Sci.* (USA) 83:730–734, (1986)).

The RNC1 λgt11 clone containing the 3 kb insert was found to cross-react with the N. crassa anti-endo-exonuclease antibody and also be disrupted by the mini-Tn10 transposon. The location of the mini-Tn10 transposon insertion in λgt11 and of the LEU2 gene on the plasmid are indicated by the inverted triangle in FIG. 1(A). The 3 kb gene's open reading frame is indicated by the arrow (a).

To isolate a yeast genomic clone containing more of the regulatory regions and open reading frame, the positive lambda gt11 clone was used to probe a yeast genomic library (YEp213). This led to the isolation of clone YEp213-10 containing a 4 kb genomic insert as described in the following experiment.

D. Isolation Of RNC1 Gene from YEp213 Yeast Genomic Library.

The 3 kb λgt11 done was isolated as described above and used as probe for obtaining a longer genomic insert from the YEp213 yeast genomic library. The λgt11 DNA insert was first isolated by EcoRI digestion and subsequent gel purification. The resultant 3.5 kb EcoRI fragment was labelled with [$^{32}$P]-dATP using a nick translation kit (BRL). *E. coli* (HB101) transformants containing the YEp213 yeast genomic library were probed with this [$^{32}$P]-labelled EcoRI DNA fragment.

Plasmids from colonies hybridizing to the 3 kb fragment were mapped with restriction endonucleases. The restriction map of one plasmid (YEp213-10) substantially matched with that of the 3 kb λgt11 clone and (FIG. 1B) possessed overlap and extension at both the 3' and 5' ends.

EcoRI digestion of YEp213-10, yielded a 4 kb fragment homologous to the 3 kb λgt11 fragment; no other fragments exhibited hybridization. The restriction enzyme map of the YEp213-10 insert is shown in FIG. 1B; regions of overlap between the λgt11 insert and the YEp213-10 insert are also indicated in FIG. 1. To further analyze the genomic YEp213-10 clone, DNA sequencing was performed as described in the following example.

E. DNA Sequencing

Nucleotide sequencing on the YEp213-10 plasmid (RNC1) was performed according to the method of Sanger and Coulson (Sanger, F. and A. R. Coulson, *FEBS Lett.* 87:107–110 (1978)) using the Pharmacia T7 sequencing kit.

The DNA sequence of the yeast 4 kb insert YEp213-10 contained a 1.4 kb open reading frame (FIG. 2). As shown in FIG. 1, the mini-Tn10 insertion point that caused elimination of the cross-reacting expression protein occurred in this putative coding region. This DNA sequence is expected to give rise to a protein of 486 amino acids having a molecular weight of approximately 57 kDa. The difference between the calculated molecular weight and the observed 72 kDa molecular weight is likely due to glycosylation at the 4 consensus sequence sites. These sites are located at positions N-15, N-193, N-259 and N-454 (FIG. 2) of the amino acid sequence.

Phosphorylation seems an unlikely candidate to cause the disparity in protein molecular weights, since treatment of the purified S. cerevisiae endo-exonuclease with alkaline phosphatase did not change its electrophoretic mobility in an SDS-polyacrylamide gel. The correlation between the YEp213-10 amino acid sequence and the previously isolated protein was further substantiated by amino acid sequencing of portions from both proteins. Protein sequencing was performed by an ABI 470 online gas phase automatic sequencer (Hong et al. (1987) *J. Biol Chem.* 262: 10728–10732)

A five amino acid stretch with the sequence aspartic-glutamic-lysine-asparagine-leucine was identified as corresponding to the five amino acids located at positions 38–42 downstream from the N-terminal methionine (FIG. 2). The lack of an identifiable sequence prior to this position was attributed to protein processing.

To ascertain the actual messenger RNA size encoding the *S. cerevisiae* endo-exonuclease, a Northern Blot procedure was performed using the isolated 4 kb YEp213-10 clone to probe total isolated yeast RNA.

F. Northern Hybridization

Total RNA was isolated according to the method described by Elder, et al. (*Proc. Natl. Acad. Sci.* (USA) 80:2432–2436, (1983)). The RNA was denatured in glyoxal and dimethylsulfoxide, then electrophoresed in a 1% agarose gel under conditions described by McMaster and Carmichael (*Proc. Natl. Acad. Sci.* (USA) 74:4835–4838, (1977)). The RNA was then transferred to a membrane and hybridized with a [$^{32}$P]-labelled YEp213-10 fragment according to methods described by Amersham (Amersham's Hybond nylon and nitrocellulose membranes-membrane transfer and detection methods (1986) Amersham Corporation, Arlington Heights, Ill). A single 2.0 kb RNA product was detected with the RNC1 radiolabeled probe.

To estimate the number of nucleotides common between the YEp213-10 done and the endogenous RNA, a S1 exonuclease experiment was performed. S1 nuclease digests single-stranded DNA or RNA molecules. Therefore, combining done YEp213-10 with *S. cerevisiae* RNA and digesting with S1 is a way of estimating the amount of overlap between the YEp213-10 clone and the endogenous RNA. For example, the YEp213-10 sequence may only correspond to a small part of the mRNA, such as only the 5' end.

G. S1 Nuclease Protection

S1 nuclease protection experiments followed the procedures of Berk and Sharp (*Cell* 12:721–732, (1977)). 20 μg of total RNA and 0.5 μg of gel purified YEp213-10 insert DNA were precipitated and resuspended in 30 μl of hybridization buffer (40 mM HEPES (pH 6.4), 1 mM EDTA, 0.4M NaCl, and 80% formamide). The nucleic acids were incubated at 85° C. for 10 min to allow disassociation and annealing of the insert DNA to the cellular RNA and then immediately shifted to a 37° C. incubator for overnight incubation. 300 μl of ice cold S1 digestion buffer (0.28M NaCl, 0.05M sodium acetate (pH 4.5), 4.5 mM ZnSO4, 20 ug/μl ss-DNA, 200 units/μS1 nuclease) containing 100 units of S1 nuclease was added.

The S1 nuclease digestion reaction proceeded at 23° C. for 3 hours, removing any single-stranded, unprotected DNA and RNA fragments. Portions of the YEp213-10 insert annealing to cellular RNAs were protected from S1 digestion. After alkaline hydrolysis of the RNA, the protected DNA was ethanol precipitated, dried, and resuspended in 10 μl of sterile, distilled water. The protected DNA fragment was sized by electrophoresis in a 0.7% agarose gel.

Figure 4A:
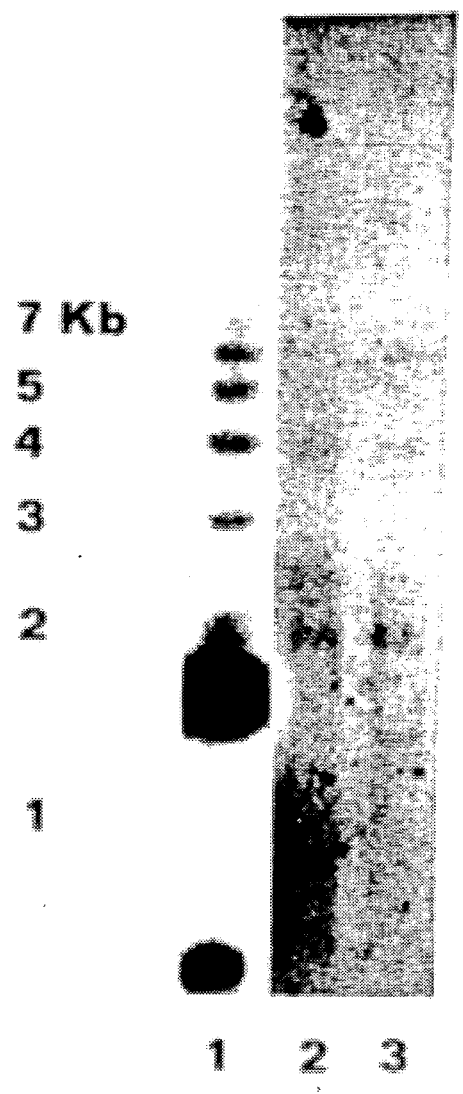
FIG. 4. (A) Northern hybridization of yeast total RNA with the complete insert from YEp213-10 as probe. Lane 1: 1 kb molecular weight standard; lane 2: total RNA from TC106d; lane 3: total RNA from the diploid TC80c X TC105d. (B) Nuclease S1 protection of the YEp213-10 insert with total yeast mRNA. Lane 1: 1 kb standard; lane 2: fragment from YEp213-10 protected from nuclease S1. The fragment of YEp213-10 used for hybridization and S1 protection was indicated on the upper panel.
Figure 4B:
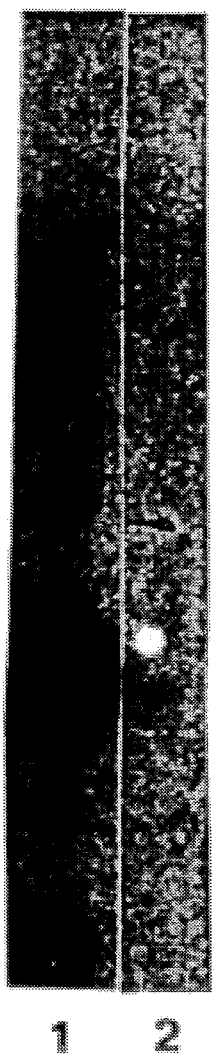
Figure 4C:
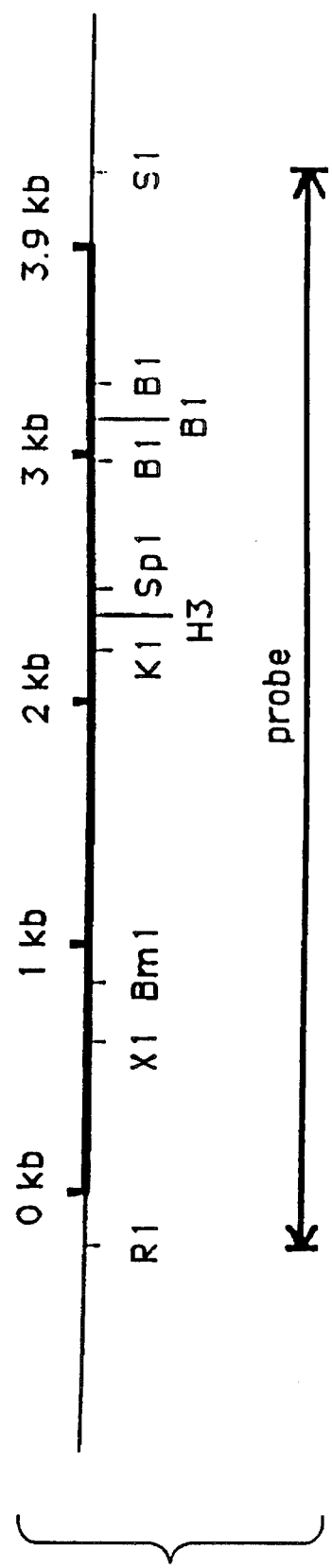

The cellular RNA provided S1 nuclease protection of a specific 1.5 kb fragment of the 4 kb YEp213-10 insert (FIG. 4B). Since the endo-exonuclease mRNA, after post-transcriptional modification, is 2 kb in length, and protected a genomic 1.5 kb fragment, almost all of the coding region was assumed to be isolated.

Although the YEp213-10 insert expressed a protein cross-hybridizing with an anti-*N. crassa* endo-exonuclease antibody, its own endo-exonuclease activity remained untested. The following experiments describe the endo-exonuclease activity of the YEp213-10 insert.

H. Endo-Exonuclease Assay

Endo-exonuclease activity of the protein expressed by YEp213-10 was measured according to methods previously described (Chow and Resnick, Cellular Response to DNA Damage, pgs. 447–455, Alan R. Liss, Inc., New York, (1983)). Others had shown that endo-exonucleases provided resistance to UV radiation and chemical DNA mutation. To prove that the RNC1 gene also conferred UV and chemical resistance to DNA damage, the following experiments were performed.

I. Methylmethanesulfnate (MMS) Sensitivity

To examine the possible function of the YEp213-10 protein in DNA repair, RAD$^+$ and rad52 bacterial strains containing the high copy YEp213-10 plasmid were exposed to MMS, a DNA damaging agent. MMS induces lesions that are subject to recombinational repair (Ho, K. S. Y., *Mutat. Res.* 20:45–51 (1975); and Resnick, M. A. and P. Martin, *Mol. Gen. Genet.* 13:119–129 (1976)).

MMS medium was prepared according to method described by Malone and Esposito (*Proc. Natl. Acad. Sci.* (USA) 77:503–507, (1980)). Logarithmically growing or stationary phase cells containing either vector (control) or YEp213-10 were plated on yeast extract peptone dextrose (YEPD) agar plates containing 0%, 0.0025%, 0.005%, 0.01%, 0.02% or 0.05% MMS. The plates were wrapped with parafilm and incubated at 30° C. for 2–3 days.

Figure 6A:
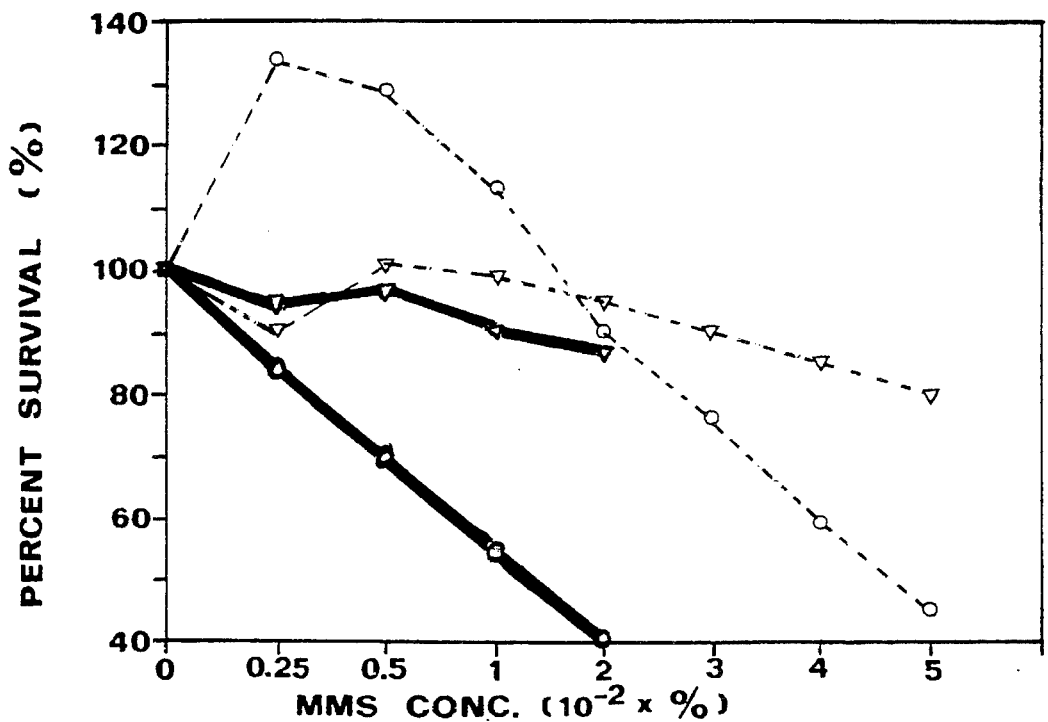
FIG. 6A: RAD$^+$ cells.

Stationary RAD$^+$ cells containing YEp213-10 were found to be much more resistant to MMS damage than those lacking the plasmid. MMS survival of RAD$^+$ cells without plasmid transfection (control) and RAD$^+$ cells containing the plasmid YEp213-10 are shown in FIG. 6A.

Figure 6B:
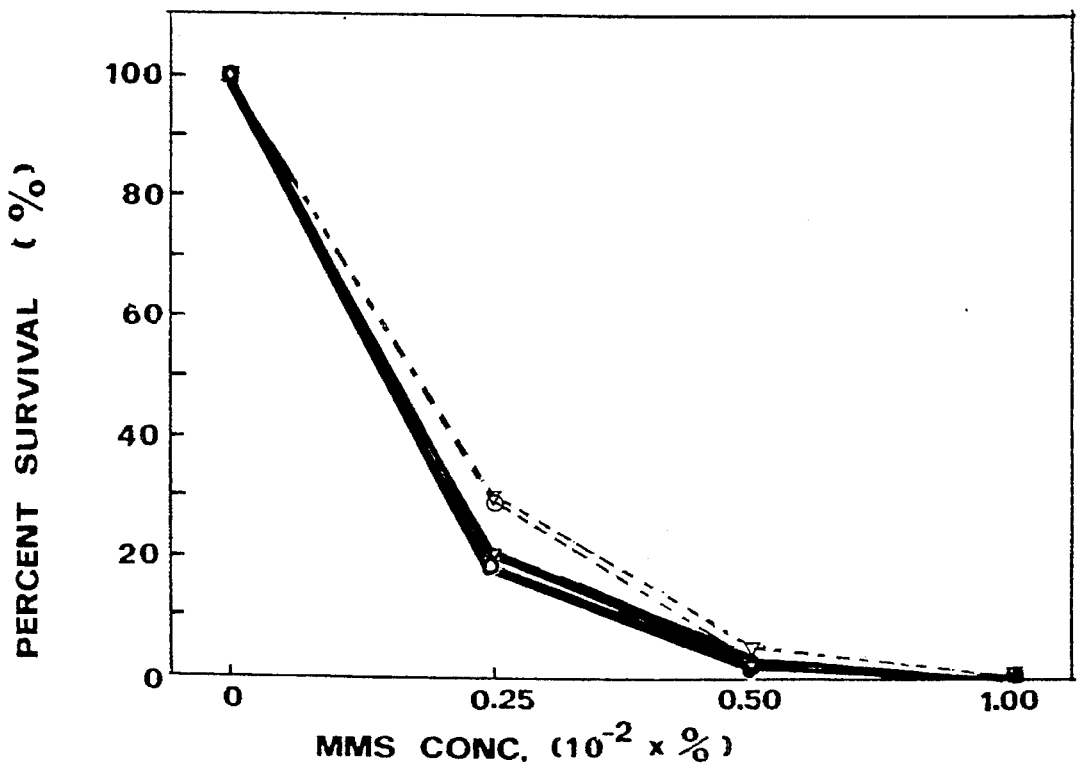
FIG. 6B: rad52 cells.

The heavy lines correspond to stationary cells and the dashed lines correspond to logarithmically growing cells. The "o" symbol represents cells containing no plasmid (control). The "∇" symbol represents cells containing the YEp213-10 plasmid. FIG. 6A shows the results from RAD$^+$ cells, FIG. 6B shows the results from rad52 cells. As shown in FIG. 6B, rad52 cells are much more sensitive to MMS than RAD+ cells.

J. Radiation Sensitivity

In experiments designed to measure ionizing radiation sensitivity, stationary cells containing either the vector (YEp213) alone, or clone YEp213-10 were plated on synthetic medium lacking leucine (to maintain the plasmid). The plates were then irradiated in a Gamma Cell 220 (Atomic Energy of Canada).

Figure 7:
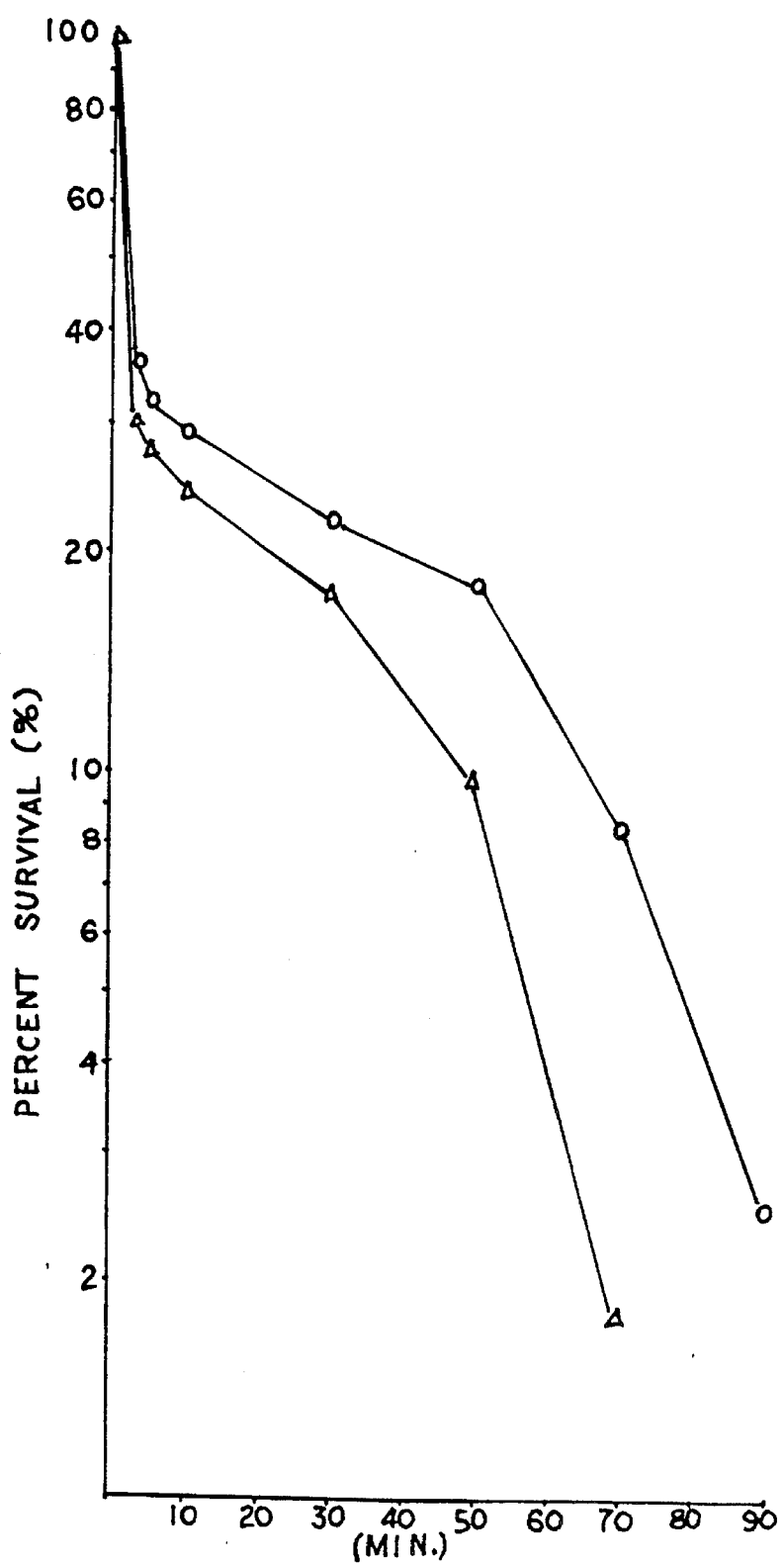
FIG. 7. Cell survival of RAD$^+$[YEp213] (triangles) and RAD$^+$[YEp213-10] (circles) after exposure to ionizing radiation.

Cell survival of RAD$^+$ cells with control plasmid vector YEp213 (∇) or with plasmid YEp213-10 (o) after exposure to ionizing radiation is shown in FIG. 7. Haploid RAD$^+$ cells containing or lacking the plasmid exhibited similar responses to ionizing radiation. There wasn't a significant difference in the percent of cells surviving either with or without the endo-exonuclease (YEp213-10) gene.

The following experiments were performed to find the genetic map location of the YEp213-10 gene.

K. Genetic Mapping of YEp213-10

To facilitate mapping, and to examine the requirement for YEp213-10, a deletion/disruption of YEp213-10 was generated. Initially, the EcoRI/SalI-RNC1 containing fragment from YEp213-10 was cloned into plasmid pUC8 resulting in plasmid pUC8yNucR. To generate the deletion/disruption of YEp213-10, the internal BglII fragments of YEp213-10 were replaced with a BamHI/BglII TRP1 containing fragment. This plasmid (pNUC::TRP1) was used for one step gene disruption into diploid cells according to the method of R. Rothstein (*Methods Enzym.* 101:202–221, (1983)).

To map strains carrying a deletion-insertion of the endo-exonuclease gene (EPY109-1D: MATα ura3-52 leu2Δ1 trp1::hisG his1-1 RNC1::TRP1) were crossed to strains carrying chromosome XI URA1 or MET14 markers. Standard genetic mapping techniques were employed.

L. Chemicals

Tri[hydroxymethyl]aminomethane was obtained from Sigma. Ethylenedinitrilotetraacetic acid (EDTA), hydrogen peroxide (30%), and methanol were from Fisher. $^{125}$I-protein A and Hybond-N membrane were from Amersham. Nitrocellulose filters were from Schleicher and Schuell. Restriction endonucleases and the DNA sequence kit were from Pharmacia Fine Chemical. Yeast extracts and Bacto-peptone were obtained from Difco.

M. Homology of YEp213-10 with rho/ras Genes and *E. Coli* recC

The N-terminal portion of the YEp213-10 gene translation product exhibits considerable homology with mammalian rho genes (FIG. 3). The rho genes are related to ras oncogenes (Chardin, et al., *Nucleic Acids Res.* 16:2717 (1988); Yeramian, et al. *Nucleic Acids Res.* 15:1869 (1987); Madaule and Axel, *Cell* 41:31–40 (1985); Madaule, et al., *Proc. Natl. Acad. Sci.* (USA) 84:779–783 (1987)). The region between amino acid 67 and 253 of the YEp213-10 gene product has 47% identity and 66% similarity with the human rhoB gene. Comparable homology was found for other rho proteins listed in GENBANK©. This region includes the GTP binding site consensus sequence.

The homology in the C-terminal portion of the expressed YEp213-10 protein (amino acid 254 to 486) and *E. coli* recC is consistent with previous observations concerning the cross-reactivity of the antisera used to isolate the YEp213-10 gene. There is a 19% identity and 44% similarity between the expressed YEp213-10 protein and the *E. coli* recC protein.

The translation product of YEp213-10 appears to be a chimeric protein containing an N-terminal rho-like portion and a C-terminal deoxyribonuclease function. The gene (YEp213-10) has thus been named RNC1 for Rho associated NuClease 1 and the originally isolated yeast endo-exonuclease is identified as RhoNUC protein to emphasize the presence of the highly conserved rho-related amino sequence. RNC1 shares no homology with RAD52.

The following experiment was performed to analyze the expression of RNC1 in logarithmically growing cells.

N. Expression of RNC1

The expression of RNC1 was examined in logarithmically growing RAD+ haploid and diploid cells. Total cellular RNA was isolated, size separated by gel electrophoresis, and subjected to Northern hybridization using labelled YEp213-10 as probe. A 2.0 kb RNA species was identified (FIG. 4A, lane 2) from the haploid cell line. Lane 1 of FIG. 4A contains a molecular weight standard while lane 3 shows the results of total RNA from the diploid TC80c X TC105d cells probed with YEp213-10.

Figure 5A:
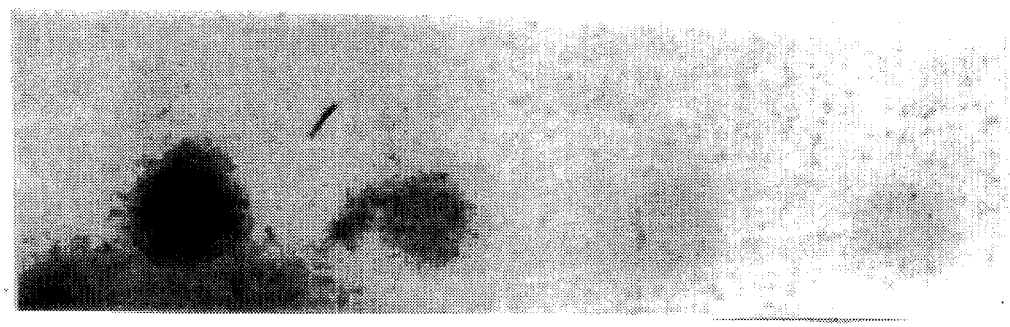
FIG. 5. Antibody cross-reacting material in (A) RAD$^+$ cell extracts and (B) RAD$^+$[YEp213-10] cell extracts. The concentration of protein in each spot are: (1) 112 mg, (2) 56 mg, (3) 28 mg, and (4) 14 mg of protein.
Figure 5B:
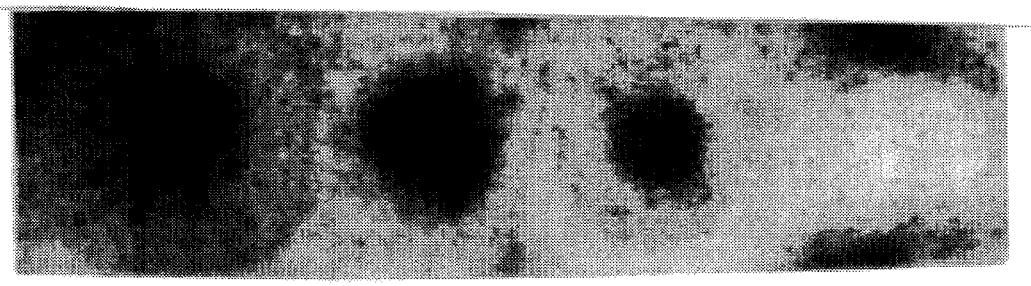

Both RAD+ and rad52 strains were transformed with YEp213-10 and the resulting isolates were examined for antibody cross-reacting material in an immuno-dot blot assay and for antibody precipitable DNase activity. The RAD+ cells yielded more cross-reacting material (FIG. 5) and more precipitable activity than the controls without plasmid (1.5 vs. 0.8 U/mg protein; Table 1). The low levels of cross-reacting material and activity in a rad52 mutant were not enhanced by the presence. of the YEp213-10 plasmid (Table 1). The requirement of the RNC1 gene product for yeast growth was also examined.

BglII fragments of RNC1 were removed and replaced by a BamHI-BglII TRP1 containing fragment. The resulting plasmid was cut with Bam HI and AflII, and the RNC1-TRP1 containing fragment was used for one-step gene disruption into diploid cells resulting in a deletion/insertion mutation of the gene. The diploids were then sporulated and dissected. Since all spores were viable, it was concluded that RNC1 is not essential for growth.

Diploids homozygous for the mutation exhibited delayed meiotic development by as much as two to three days over the normal single day required for sporulation. This indicated a role for the gene in meiotic development and suggests that mutants may be used to study this developmental process. The mutants may prove useful for isolating genes that complement or suppress this phenotypic defect.

An additional category of mutants has been isolated based on in vitro mutagenesis of the G protein GTP binding consensus sequences identified in the RNC1 gene. When this type of mutagenized RNC1 plasmid was placed in a cell mutant, temperature sensitive growth was observed. This result may define a role for the RNC1 gene in normal cell growth and suggests the possibility of isolating mutants and complementing genes that will suppress the genetic defect. It is also possible that altered RNC1 may be useful for characterizing related genes from other organisms, including humans.

Such mutations in the related ras gene of humans are identified with many types of cancers. These results are consistent with the observation that over-expression of the RNC1 gene leads to abnormal cell growth and abnormally diffuse nuclei. The amount of RhoNUC may have to be carefully balanced in the cell for appropriate cell growth.

TABLE 1

Deoxyribonuclease Activity in Extracts of RAD+, RAD+[YEp213-10], rad52 and rad52[YEp213-10]

| PRE-CIPITATED | TOTAL DNase (U/mg prot.) | Ab-PRECIPITABLE DNase (U/mg prot.) | % DNase |
| --- | --- | --- | --- |
| RAD+ | 3.3 | 0.8 | 26 |
| RAD+ [YEp213-10] | 3.4 | 1.5 | 44 |
| rad52 | 3.0 | 0.1 | 3 |
| rad52 [YEp213-10] | 3.1 | 0.3 | 9 |

The following experiments were performed to determine the chromosomal location of RNC1.

O. Chromosomal Localization of RNC1

To identify the physical and genetic location of RNC1, yeast chromosomes were subjected to OFAGE gel electrophoresis and hybridized with the 4 kb insert from YEp213-10. Hybridization was specific to Chromosome XI. The gene RNC1 was located to chromosome XI since the probe containing RNC1 and a chromosome XI specific probe hybridized to the same chromosome. The genetic location of RNC1 was examined by crossing RNC1::TRP1 mutants with strains containing the centromere marker MEt14 and the left arm marker URA1. Meiotic mapping indicates that RNC1 is unlinked to either marker.

In addition to the experimental data presented related to the Yeast endo-exonuclease, the discovery of mammalian endo-exonucleases is disclosed below.

II. ISOLATION AND CHARACTERIZATION OF MAMMALIAN ENDO-EXONUCLEASES

Another aspect of the present invention relates to the discovery of the first "primate" endo-exonuclease. While humans are not always considered as primates, as used herein the term "primate" shall relate to monkeys, apes and humans. We have also discovered the first mammalian endo-exonuclease having primary exonuclease activity in the 5'→3' direction and the first mammalian endo-exonuclease having exonuclease activity on double-stranded polynucleotides and endonuclease activity on single-stranded polynucleotides.

A primate endo-exonuclease was isolated from the cultured mammalian cell line CV-1 and from the transformed cell line COS-1. The endo-exonuclease properties of the enzyme are very similar to that discovered in yeast (supra), thus suggesting its potential role as a DNA recombination/repair nuclease. Moreover, the amount of the endo-exonuclease appears greater in the transformed COS-1 cells than the CV-1 cells.

The experimental protocol used to isolate this mammalian endo-exonuclease involved protein column purification of total cellular fractions and subsequent testing for nuclease activity. The steps described below exemplify one procedure for isolating and identifying endo-exonuclease activity from protein extracts of mammalian cells.

A. Isolation of a Mammalian Endo-exonuclease

Cells (CV-1 and COS-1) were grown to confluence in DME media containing 5% new born fetal calf sera (NB). Adherent cells were harvested by scraping the cell culture plates with a rubber policeman. The resultant cell suspension was centrifuged at 4° C., 700–800× g, and washed twice with cold PBS. The cells were thereafter resuspended in 1 ul 20 mM Tris-HCl pH 7.5 containing 5 mM EDTA and 1 mM Phenylmethylsulfonyl fluoride (PMSF from BRL, Bethesda, Md). Cell suspensions were then sonicated with in a W-380 Ultrasonic Processor (Heat Systems-Ultrasonics, Inc.) at a 1 second cycle pulse time, maximum output, for 60 seconds. The resulting disrupted cell suspensions were centrifuged at 10,000 ×g for 15 minutes in the cold to pellet insoluble material. The crude extracts (supernatants) were saved and the pellets discarded.

B. Purification of Endo-Exonuclease

Extracts from CV-1 and COS-1 cells were spotted onto HYBOND-N© membrane (Amersham) under vacuum with a Dot Blot apparatus (Tyler). The membrane was exposed to ultraviolet light for 5 min, then treated with rabbit antiserum raised against the *N. crassa* endo-exonuclease according to the previous methods (Towbin, et al., *Proc. Natl. Acad. Sci. U.S.A.*, Vol. 76, pp. 4350–4354 (1979)). The membrane was enclosed in a boiling pouch with 10–15 ul of buffer B (10 mM Tris-HCl, pH 8.0, 1 mM EDTA, 150 mM NaCl) containing 2% skim milk powder to block non-specific protein binding sites, and incubated for at least 3 hours with gentle agitation at room temperature (approximately 23° C.).

The membrane was rinsed for a total of 45 min at room temperature in three changes of buffer B, resealed in a boiling pouch with 10–15 μl buffer B (containing skim milk powder) and incubated for at least 1.5 hours at room temperature with horseradish peroxidase conjugated protein A. The membrane was then rinsed at room temperature for 15 min in buffer B, for 30 min in buffer B containing 1M NaCl, and for 15 min again in buffer B. The immune-crossreactive material was visualized via the horseradish peroxidase reaction.

Preliminary immuno-dot blot results with extracts from mammalian CV-1 and COS-1 cells targeted by the *N. crassa* endo-exonuclease identified the presence of cross-reacting protein(s) in mammalian cells. The preliminary results also indicated that a rapid purification method would be necessary since the cross-reactive protein was reduced upon aging. To overcome this problem, an *N. crassa* antibody-protein A-Sepharose affinity column was used to isolate the mammalian nuclease.

Results with the *Saccharomyces cerevisiae* endo-exonuclease gene (RNC1) had revealed that it was a chimeric protein with GTP protein binding sequences at the N-terminal and a nuclease-like domain at the C-terminal. Therefore, to ensure that the positive dot-blot results indicated an endo-exonuclease, a rabbit antibody was raised against the RhoNUC protein lacking the G-protein portion. Antibodies specific for this protein would therefore specifically recognize only the nuclease domain of the enzyme. This eliminated any possibility of isolating non-specific GTP-binding proteins common in mammalian cells.

C. Antibody Affinity Column

Supernatant from the crude CV-1 or COS-1 cell extracts was purified by placement over an antibody-protein A-Sepharose affinity column (Chow, T. Y.,-K and Resnick, M. A., *J. Biol. Chem.*, Vol.262, pp. 17659–17667 (1987)). Antibody directed against *N. crassa* was attached to the column material, and cellular extracts were then run through. Buffer A containing 75 mM NaCl was added to the column until the $OD_{280}$ of the eluted fraction wash was near zero, indicating that all non-bound protein had been rinsed from the column. 3.5M $MgCl_2$ (buffered with 20 mM Tris-HCl, pH 7.5) was then applied to the column to strip off any antibody bound protein. The protein fraction eluted with the salt gradient was dialyzed against buffer A overnight with at least two changes of fresh buffer.

The proteins of the crude (CV-1 cell) extracts were resolved into two peaks from affinity column. Almost all of the protein (99% or more) passed through the column, while the remainder, less than 1% of the total protein, was eluted with the 3.5M $MgCl_2$ buffer.

Figure 8A:
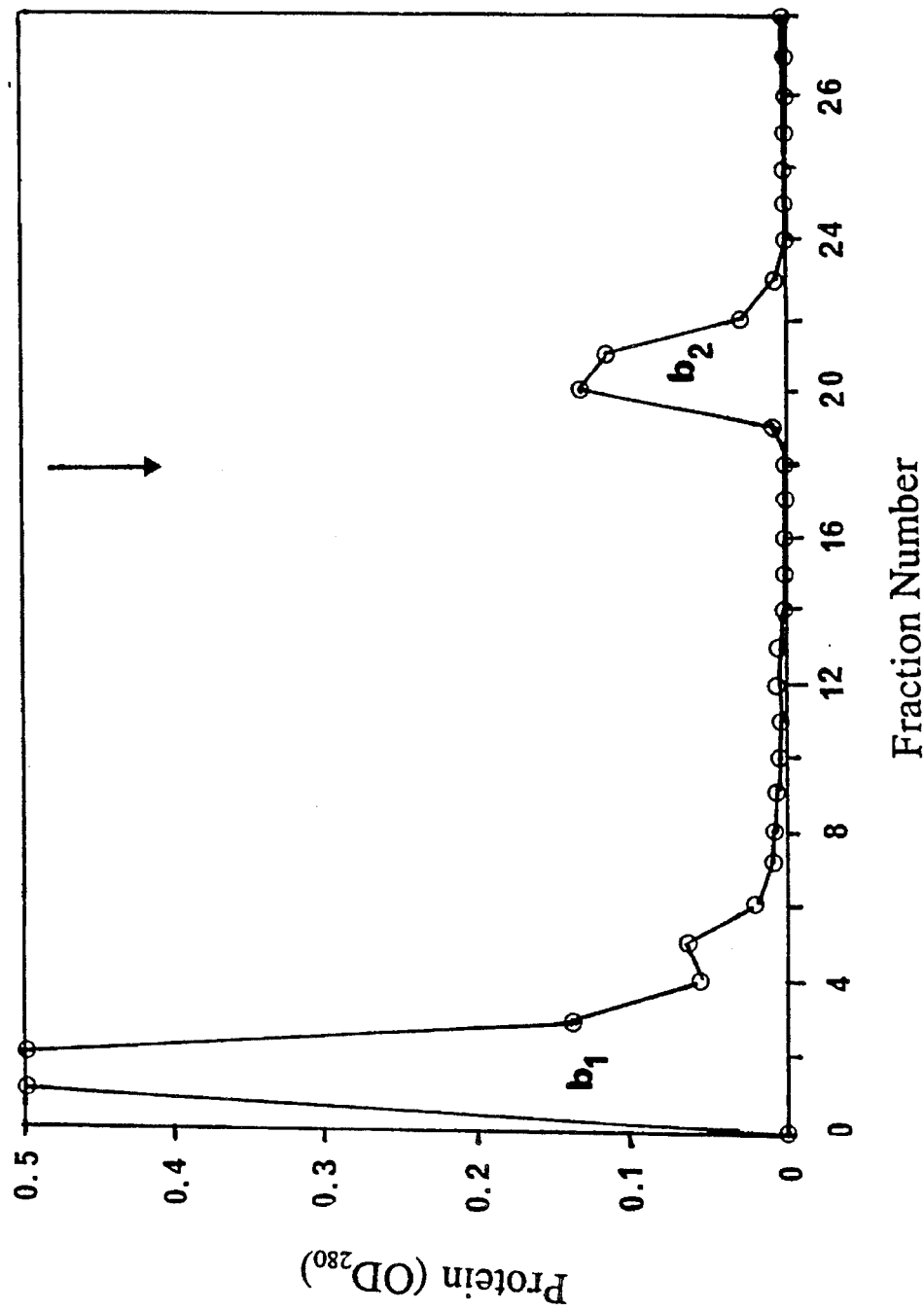
FIG. 8: Antibody-protein A Sepharose affinity chromatography of CV-1 cell extract and characterization of the eluted protein. Panel A. Chromatographic profile of the proteins. The arrow indicates the point at which elution with 3.5M MgCl$_2$ was begun. Panel B. SDS-polyacrylamide gel electrophoresis of b$_1$ (pass-through fraction). Panel C. SDS-polyacrylamide gel electrophoresis of b$_2$ (5 units of the eluted protein fraction). Lane a in both panels B and C contains protein standards. Panel D. 5–20% linear sucrose density sedimentation velocity centrifugation of b$_2$ (5 units of the eluted protein fraction). One µg of b$_2$ was mixed with 0.5 mg of bovine hemoglobin (Hb) and loaded on top of the sucrose density gradient. The gradient was centrifuged for 23 h at 4° C. and then fractionated into 200 µl fractions. Absorbance at 440 nm and ss-DNase activity were measured for each fraction as described in the detailed description section.

FIGS. 8A, 8B, and 8C show the results of the antibody-protein A Sepharose affinity chromatography of CV-1 cell extracts. In the chromatographic profile of the proteins (panel A) the arrow indicates the point at which elution with 3.5 M $MgCl_2$ was begun. Fractions 19–23 contain the bound protein ($b_2$), eluted after $MgCl_2$ treatment.

FIG. 8B is a SDS-polyacrylamide gel of the pass-through (non-binding) fraction revealing multiple protein bands. FIG. 8C is a SDS-polyacrylamide gel of 5 units of the eluted (bound) protein fraction and only shows a single band of about 65 kd. Lane A of panels B and C in FIG. 8 contain protein size standards. Only a single sized protein remained bound to the antibody affinity column.

SDS-polyacrylamide gel electrophoresis of the protein preparations were performed according to the method of Laemuli (Laemmli, U.K., *Nature*, Vol. 227, pp. 680–685 (1976)). Protein bands were visualized by Coomassie Blue staining.

Figure 8D:
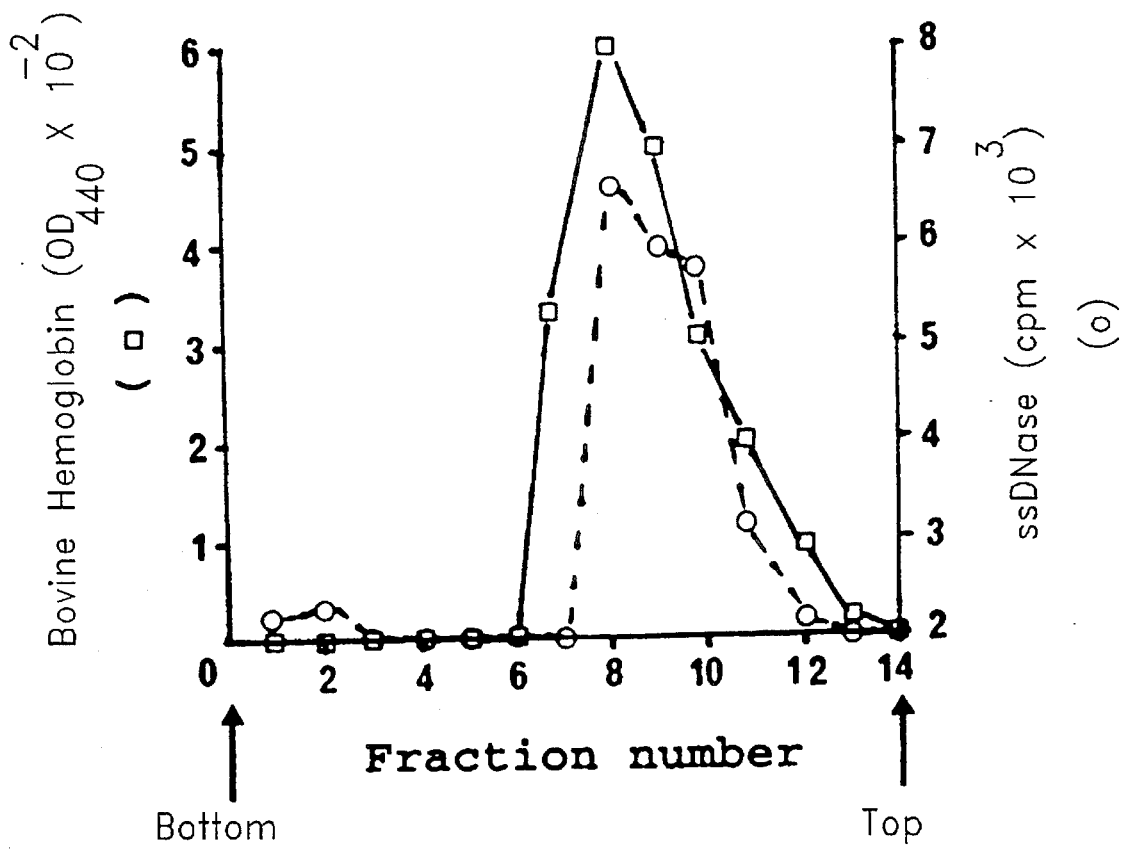

The native molecular weight of the mammalian endo-exonuclease was estimated from its sedimentation coefficient obtained by sucrose density gradient centrifugation using bovine hemoglobin as a marker protein (FIG. 8D, broken line). Sedimentation coefficients from the sucrose density gradient were determined according to known methods (Martin, R. G. and Ames, B. N., *J. Biol. Chem.*, Vol. 236, pp. 1372–1379 (1961)) by centrifugation in linear 5–20% sucrose gradients (20 mM Tris-HCl pH 7.5 containing 5 mM EDTA).

The native protein molecular weight was estimated to be 60000–70000, in agreement with the polypeptide results. Immunoblots with the crude cell extract and the purified protein confirmed the 65 kDa protein as the only protein cross-reacting with the antibody. Each fraction was then assayed for ss-DNase activity as described below (FIG. 8D, solid line). The peak of ss-DNase activity sedimented just behind of the peak of the hemoglobin marker protein. The specific activity of the purified protein was 256 U/mg with a purification factor of 25.

D. Determination of Endo-Exonuclease Activity

Deoxyribonuclease activity was determined by measuring the release of acid-soluble radioactivity from $^{32}$P-labeled denatured or native linearized pBR322 plasmid DNA (specific activity 1–2×10$^6$ cpm/μmole) according to the method described by Chow and Resnick (*J. Biol. Chem.*, Vol.262, pp. 17659–17667 (1987)). The assay mixture contained 100 mM Tris-HCl pH 8.0, 10 mM $MgCl_2$, and 17 μg of $^{32}$P-labelled linearized plasmid DNA. One unit of activity is defined as the amount of deoxyribonuclease which renders 1 μg of DNA acid-soluble in 30 min at 37° C. The plasmid was labeled using a random oligo-priming kit (Pharmacia Fine Chemical).

Figure 9:
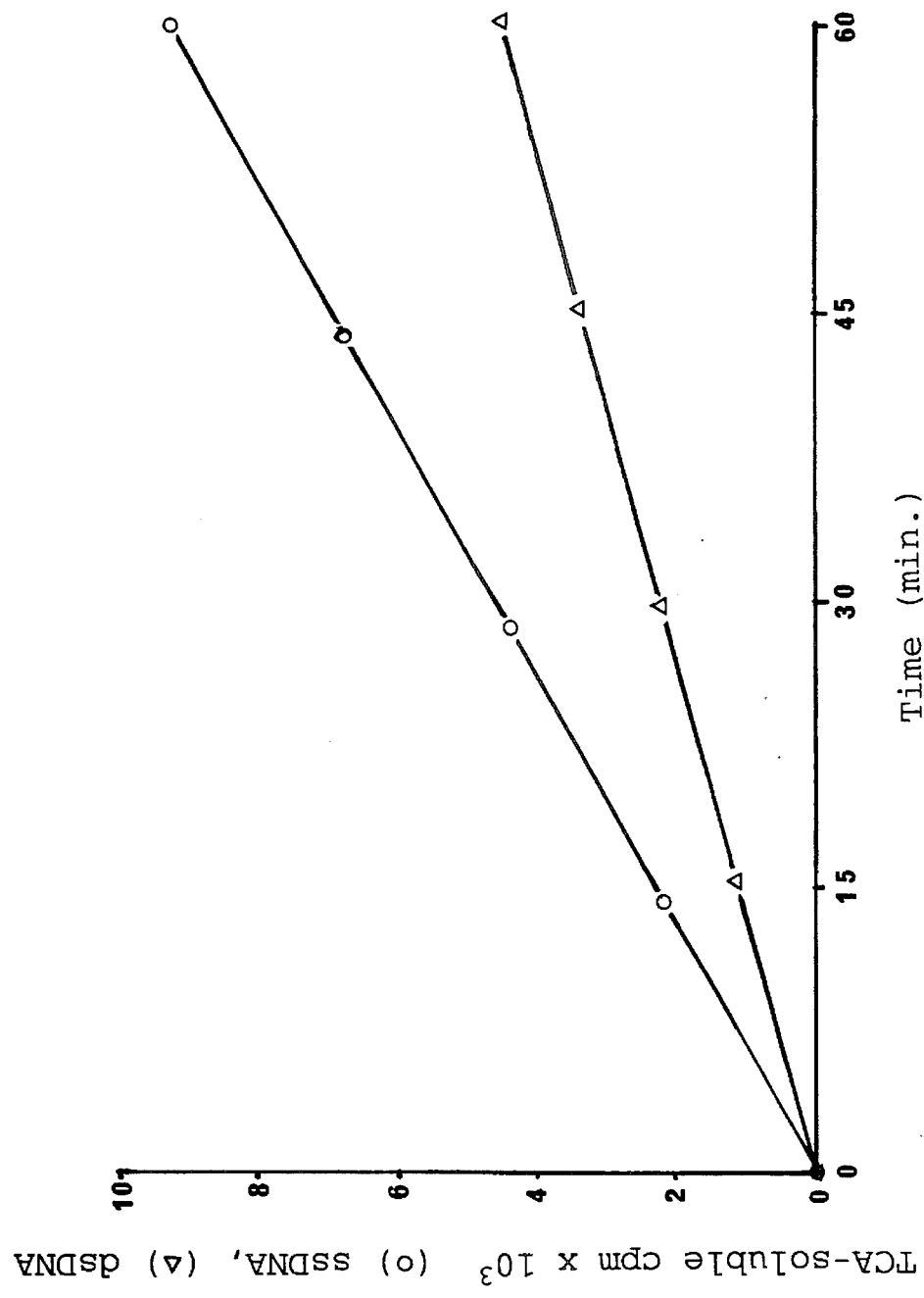
FIG. 9: Activity of the purified mammalian endo-exonuclease toward different substrates. 1.0 unit of purified endo-exonuclease was incubated with either ss-DNA (O) or ds-DNA (Δ) as substrate. Trichloroacetic acid (TCA) soluble radioactivity was determined.

We measured the activity of the purified mammalian endo-exonuclease on different substrates over time. These results are shown in FIG. 9. Purified endo-exonuclease (1.0 unit) was incubated with either ss-DNA (○) or ds-DNA (Δ). Trichloroacetic acid (TCA) soluble radioactivity was determined. Eluted fraction $b_2$ solubilized both ds-DNA and ss-DNA in a linear fashion over time.

Ribonuclease activity was determined by the appearance of small fragments upon electrophoresis on a 1.5% Ultrapure (BRL) agarose gel (20 mM MOPS, 5 mM Sodium acetate, 0.7 mM EDTA and 5% formaldehyde) with poly-rA substrate and $b_2$ using the deoxyribonuclease assay conditions.

Superhelical pBR322 DNA was treated with 5 units of the antibody-column purified mammalian endo-exonuclease at 37° C. Reactions were stopped by the addition of solution containing 5 mM EDTA, 1% SDS, 30% glycerol, and bromophenol blue. The resulting mixtures were then loaded onto a 0.7% agarose gel and electrophoresed for 3 hours at 70 V. The gels were stained with 100 ul of 0.5 µg/ul ethidium bromide solution.

E. Mode of Degradation

The mode of degradation of ss-DNA and ds-DNA (distributive or processive) was determined by pulse-chase experiments. Excess unlabeled DNA was added to degradation reactions of [$^{32}$P]-labeled denatured or native linearized pBR322 plasmid DNA (Chow, T. Y.-K and Fraser, M. J., *J. Biol. Chem.*, Vol. 258, pp. 12010–12018 (1983)). pBR322 ds-DNA was 5' end termini$^{32}$P-labeled according known methods (Weiss, B., Live, T. R. and Richardson, C. C., *J. Biol. Chem.*, Vol. 243, pp. 4530–4542 (1968)). Linearized pBR322 ds-DNA was uniformly internal $^3$H-labeled by methods known in the art. End-labeled $^{32}$P-ds-DNA had a specific activity of 8.6×10$^5$ cpm/pmol.

Double-stranded DNA was 3'-end labelled according to the method described by Drouin (*J. Mol. Biol.*, Vol. 140, pp. 15–34 (1980)) using DNA polymerase I (Klenow fragment). The 3'-end labelled $^{32}$P-ds-DNA has a specific activity of 9.0×10$^5$ cpm/pmol.

F. Mode of Action by the Nuclease on Different Substrates

The purified mammalian nuclease solubilized ss-DNA, ds-DNA (FIG. 9) and poly-rA (data not shown). The nuclease was also able to relax superhelical pBR322 DNA suggesting an endonucleolytic mode of action. The nuclease further acted on the relaxed circular molecules to yield linear double-strand DNA; this was followed by the generation of smaller fragments (FIG. 10, lines 2–6).

Figure 10:
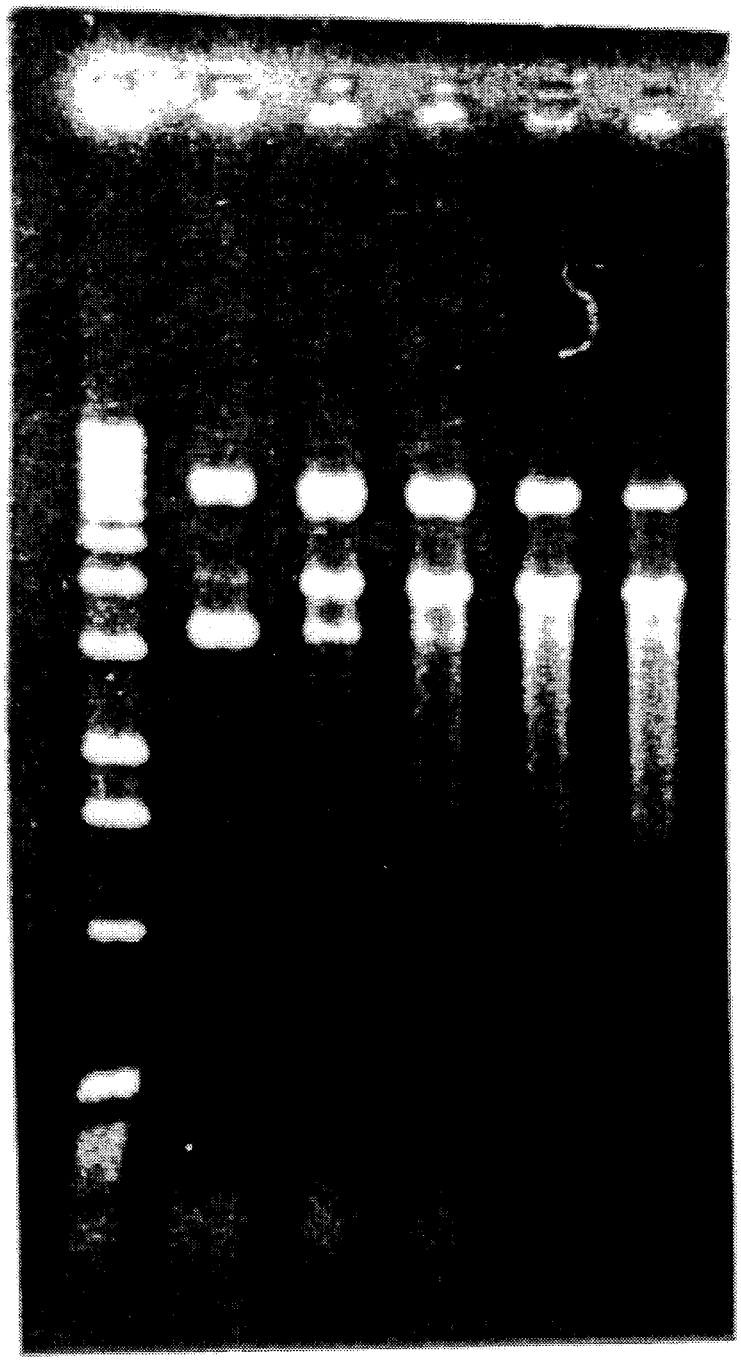
FIG. 10: Activities of the purified endo-exonuclease on pBR322 RF I DNA. 5.0 units of purified mammalian endo-exonuclease was incubated with 0.5 µg of pBR322 (form I). Lane 1, 1 kb ladder DNA standard. Lane 2–6 respectively 0, 10, 20, 30 and 40 min digestion.

FIG. 10 shows the activities of the purified endo-exonuclease on pBR322 RFI DNA. 5.0 units of purified mammalian endo-exonuclease was incubated with 0.5 µg of pBR322. FIG. 10, Lane 1, contains a 1 kb DNA standard ladder. Lane 2–6 reveal 0, 10, 20, 30 and 40 minute digestions respectively of pBR322 with the purified endo-exonuclease (fraction b$_2$).

G. Mammalian Endo-Exonuclease Processivity

Figure 11B:
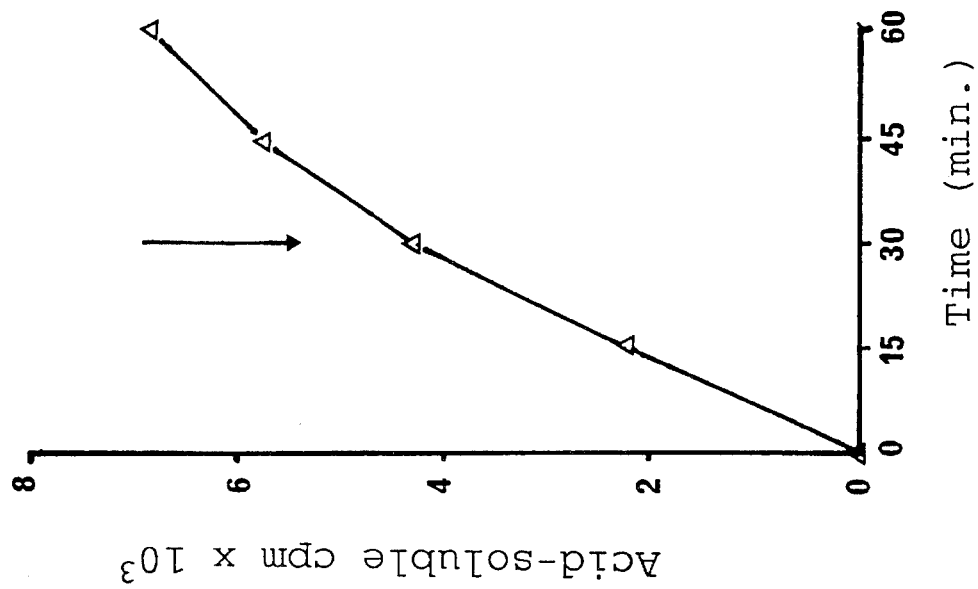
FIG. 11: Processivity of mammalian endo-exonuclease. Panel a, ss-DNA. Panel b, ds-DNA. In each case, two units of purified endo-exonuclease were added to a reaction mixture containing either $^{32}$P-labeled ss-DNA or $^{32}$P-labeled ds-DNA. The rate of release of acid-soluble radioactive material was then measured. After 30 min of reaction, cold ss-DNA or ds-DNA (50 times excess) was added to the appropriate reaction mixture (indicated by the arrow), and the monitoring of the rate of release of acid-soluble radioactive material continued for another 30 min.
Figure 11A:
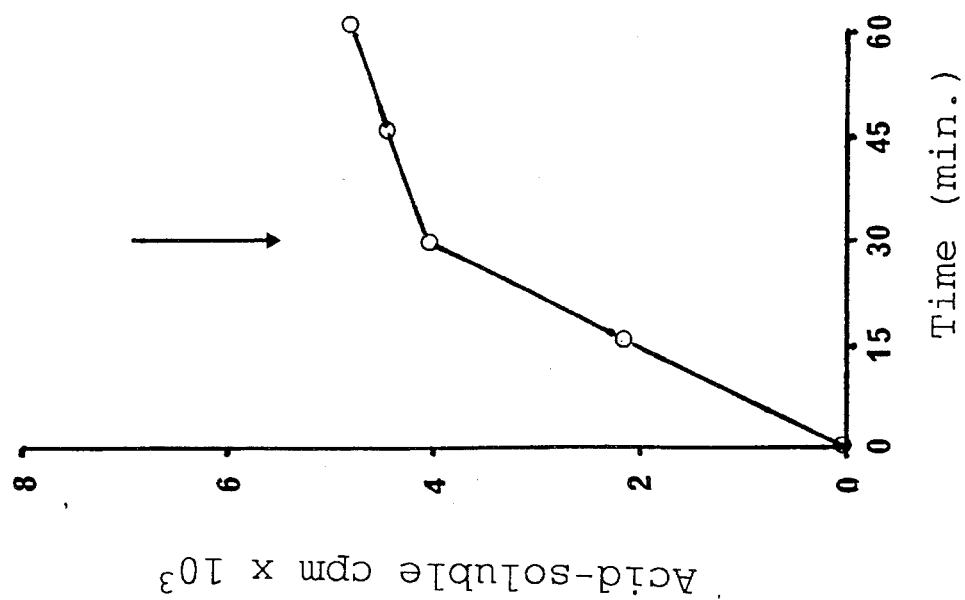

The endo-exonuclease mode of action on ss-DNA substrate appears to be non-processive, but with ds-DNA it is processive (FIG. 11, panel a and b). FIG. 11 shows the results of experiments to assess the processivity of mammalian endo-exonuclease. Panel a contains ss-DNA results while Panel b contains ds-DNA results. In each case, two units of purified endo-exonuclease (b$_2$) were added to a reaction mixture containing either $^{32}$P-labeled ss-DNA or $^{32}$P-labeled ds-DNA. The release rate of acid-soluble radioactive material was then measured. After a 30 min reaction, unlabeled ss-DNA or unlabelled ds-DNA (50 times excess) was added to the appropriate reaction mixture (indicated by the arrow), and the release rate of acid-soluble radioactive material was monitored for another 30 min.

The addition of a 50-fold excess of unlabelled ss-DNA to the ss-DNase reaction mixture immediately reduced the release rate of acid-soluble radioactive products (FIG. 11, panel a). However, the addition of a 50-fold excess of unlabelled ds-DNA to the ds-DNase reaction mixture did not alter the rate of degradation immediately (FIG. 11, panel b).

Figure 12A:
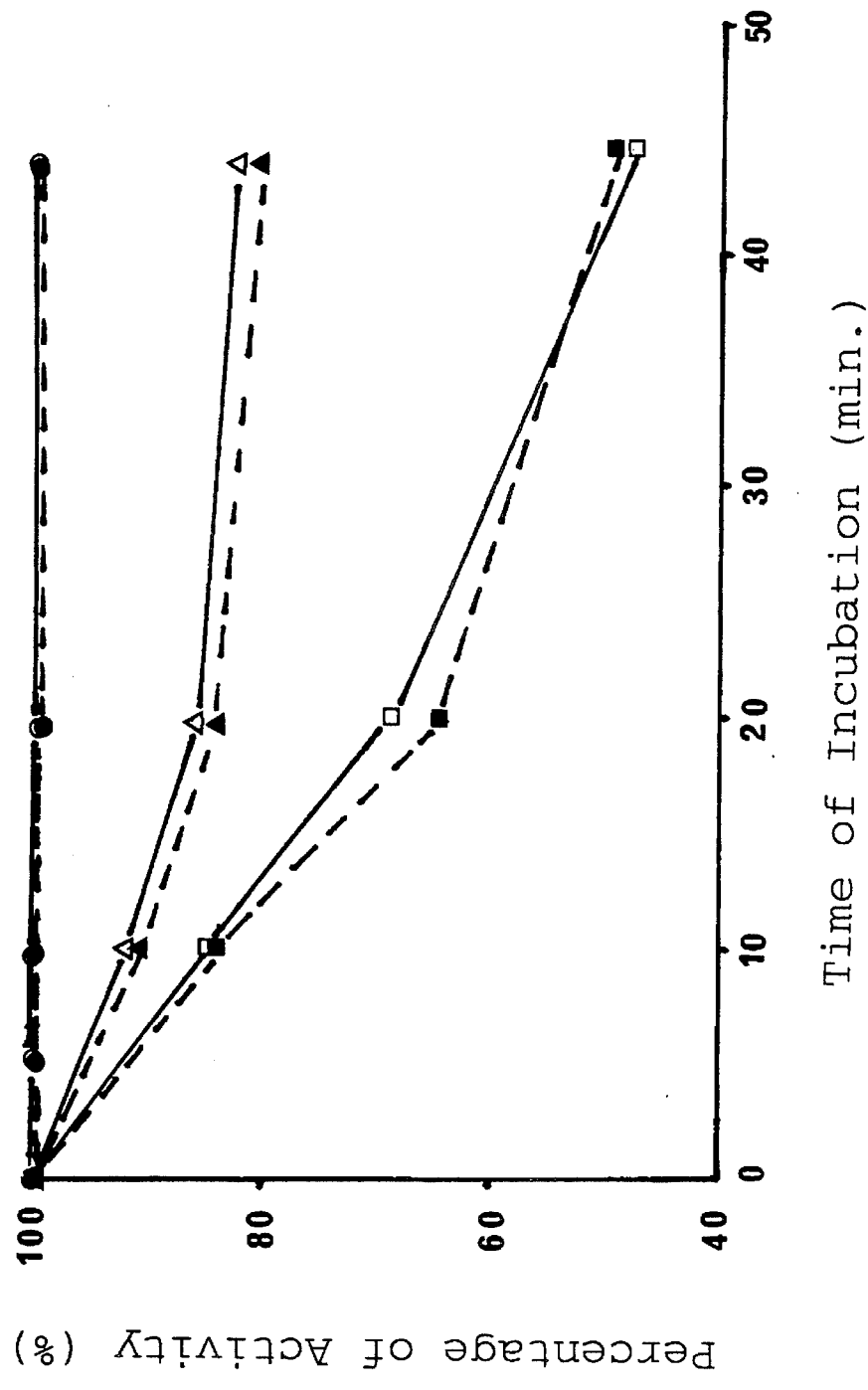
FIG. 12: Panel A. Heat activation of mammalian endo-exonuclease. The endo-exonuclease was incubated at 37°, 50° and 60° C. in buffer A. Aliquots were then withdrawn and assayed at 37° C. for both ss- and ds-DNase activity. Incubation at 37° C., ss-DNase (O), ds-DNase (●); incubation at 50° C., ss-DNase (Δ), ds-DNase (▲); and incubation at 60° C., ss-DNase (□), ds-DNase (■). Panel B. pH dependence of DNase activities of mammalian endo-exonuclease. ss-DNase activity (O) and ds-DNase activity (Δ).
Figure 12B:
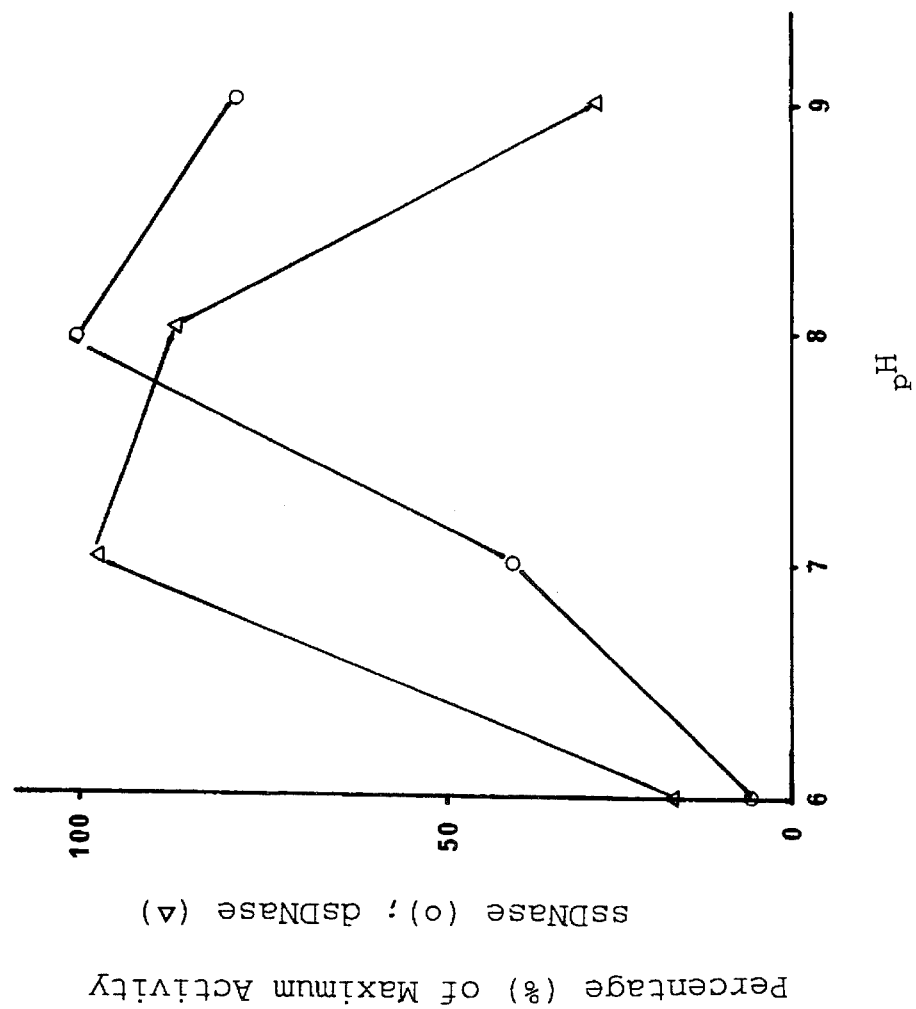

The same protein seemed to act on ss-DNA and ds-DNA since heat inactivation of the purified nuclease at two different temperatures inactivated both ss-DNase and ds-DNase activity at the same rate (FIG. 12, panel A). FIG. 12 shows the results of heat activation experiments on mammalian endo-exonuclease.

The purified mammalian endo-exonuclease was incubated at 37°, 50° and 60° C. in buffer A. Aliquots were withdrawn and assayed at 37° C. for both ss-DNase and ds-DNase activity. Panel A shows incubation at 37° C. of ss-DNase (○) and ds-DNase (●); incubation at 50° C. of ss-DNase (△) and ds-DNase (▲); and incubation at 60° C. of ss-DNase (□) and ds-DNase (■). The pH dependence of mammalian endo-exonuclease DNase activity is shown in Panel B.

Both ss-DNase activity (○) and ds-DNase activity (△) are indicated. Tris-HCl buffer (100 mM) at various pHs containing 10 mM MgCl$_2$ was used in the determination.

The enzyme was stable at 37° C. The optimal pH for ss-DNase was pH 8–9 whereas ds-DNase was stable at pH7–7.5 (FIG. 12, panel B).

From the foregoing experiments, it can be seen that the endo-exonuclease we isolated has exonuclease activity on double-stranded DNA and endonuclease activity on single-stranded DNA.

H. Polarity of Nucleolytic Reactions

The polarity direction of the endo-exonuclease reaction was analyzed by studying the release of acid soluble radioactivity from either the 5', 3', or internal portion of the substrate DNA. FIG. 13 shows the results of experiments on the activity of mammalian endo-exonuclease on $^{32}$P end-labeled double-stranded DNA, and internally $^3$H-labeled double-stranded DNA. The 5' termini was $^{32}$P labeled using T4 polynucleotide kinase while the 3' termini was labeled with the Klenow fragment of Polymerase I. Acid-soluble radioactivity was released from 5'-$^{32}$P-end labeled ds-DNA (○) and internally $^3$H-labeled ds-DNA (□*) as shown in FIG. 13.

However, none or very little radioactive product was released with 3'-[$^{32}$P]-labeled ds-DNA (●) substrate after up to 10 minutes of digestion. As a control for the reaction, a steady release of $^3$H-labeled product was detected with the internally $^3$H-labeled ds-DNA substrate.

The polarity of the mammalian endo-exonuclease activity on ds-DNA appears to be 5' to 3' since radioactivity products were released immediately from 5' end $^{32}$P-labeled ds-DNA with no further release of label after a 1 minute reaction.

I. Effects of Divalent Metal Ions, NaCl, ATP and GTP

The ss-DNase, ds-DNase and RNase activities of the endo-exonuclease required divalent cations. Comparable ss-DNase and ds-DNase activities were obtained with Mg$^{2+}$ in the 10 mM range but ss-DNase activities were higher at lower Mg$^{2+}$ concentrations tested (Table 2). The optimal Mg$^{2+}$ concentration for ss-DNase was 0.5 mM whereas for ds-DNase it was 2.5 mM. The ratio of ss-DNase/ds-DNase activity increased from 1.3 to 2.2 as the concentration of the Mg$^{2+}$ dropped from 10 mM to 0.5 mM. The ratios are calculated with respect to the activity of 10 mM Mg$^{2+}$ (100%). The divalent metal ions Mn$^{2+}$, Zn$^{2+}$ and Ca$^{2+}$ were found to partially substitute for Mg$^{2+}$. The optimal concentrations for Mn$^{2+}$ and for Zn$^2$ $^+$were lower than for Mg$^{2+}$, while Mn$^{2+}$ and Zn$^{2+}$ concentrations of 2.0 mM and 0.25 mM (or higher) respectively had inhibitory effects on the nuclease activities. The Ca$^{2+}$ activities alone were lower than observed with Mg$^{2+}$alone, but combinations of Ca$^{2+}$and Mg$^{2+}$in the reaction mixture synergistically activated the nuclease activities (Table 2).

The addition of increasing NaCl concentrations to the assay mixtures containing 10 mM Mg$^{2+}$markedly reduced the DNase activities of mammalian endo-exonuclease. Both ss-DNase and ds-DNase activities were reduced to the same extent (Table 3).

The nuclease activities of putative recombination nucleases of *E. coli* are known to be affected by ATP. Moreover *S. cerevisiae* endo-exonuclease is believed to contain a region homologous to GTP-binding sites. The effects of ATP and GTP on the purified mammalian endo-exonuclease were therefore chosen to study. In general, both the ss-DNase and ds-DNase activities were slightly inhibited by ATP and GTP (0.1–1.0 mM). With GTP, however, there may have been a slight enhancement of ds-DNase activity at a 0.1 mM concentration (Table 3).

TABLE 2

Divalent Metal Ion Dependence on the ss- and ds-DNase Activities of the Mammalian Endo-Exonuclease

| Metal Ion | Concentration (mM) | Activity % ss-DNase | Activity % ds-DNase | Ratio of Activities for ss/ds-DNase |
|---|---|---|---|---|
| $Mg^{2+}$ | 0 | 0 | 0 | — |
|  | 0.5 | 217 | 128 | 2.2 |
|  | 2.5 | 203 | 168 | 1.6 |
|  | 5.0 | 173 | 120 | — |
|  | 10.0 | 100 | 100 | 1.3 |
| $Mn^{2+}$ | 0.5 | 258 | 195 | 1.7 |
|  | 1.0 | 215 | 212 | 1.4 |
|  | 2.0 | 0 | — | — |
|  | 2.5 | 0 | 0 | — |
|  | 5.0 | 0 | — | — |
| $Ca^{2+}$ | 0.25 | 58 | 88 | 0.9 |
|  | 0.5 | 67 | 80 | 0.8 |
|  | 2.5 | 65 | 85 | — |
|  | 5.0 | 40 | 57 | 0.8 |
| $Zn^{2+}$ | 0.1 | 75 | 70 | — |
|  | 0.25 | 0 | 0 | — |
|  | 0.5 | 0 | 0 | — |
|  | 1.0 | 0 | — | — |
| $Ca^{2+} + Mg^{2+}$ | 2.5, 5.0 | 414 | 340 | — |

Standard assays at 37° C. with ss- or ds-DNase activity in the presence of 10 mM $Mg^{2+}$ is equal to 100%.

TABLE 3

Effects of NaCl, ATP and GTP on the ss- and ds-DNASE Activities of the Mammalian Endo-Exonuclease

|  | Concentration | Activity % ss-DNase | Activity % ds-DNase | Ratio of Activities for ss/ds-DNase |
|---|---|---|---|---|
| NaCl | 0 | 100 | 100 | 1.4 |
| (M) | 0.1 | 25 | 36 | 0.9 |
|  | 0.2 | 13 | 19 | 0.9 |
|  | 0.3 | 6 | 9 | 0.9 |
| ATP | 0 | 100 | 100 | — |
| (mM) | 0.1 | 88 | 70 | — |
|  | 0.5 | 87 | 77 | — |
|  | 1.0 | 77 | 60 | — |
| GTP | 0 | 100 | 100 | — |
| (mM) | 0.1 | 85 | 112 | — |
|  | 1.0 | 68 | 73 | — |

Standard assays at 37° C. with ss- or ds-DNase activity in presence of 10 mM $Mg^{2+}$ is equal to 100%.

J. Interaction with Synthetic Holliday Junction

A synthetic Holliday Junction substrate was prepared according to the method described by Parsons and West (Parsons, C. A. and West, S. C., *Nucl. Acids Res.*, Vol. 18, pp. 4377–4384 (1990)) using the synthetic oligonucleotides. The synthetic Holliday junction substrate was 3'-terminus labeled using polymerase I-Klenow fragment with 40 µCi [$^{32}$P]dCTP. The Junction DNA was gel purified in 10% native polyacrylamide (acrylamide:bisacrylamide, 30:1). The DNA was recovered by band excision, electroelution, and dialysis against 10 mM Tris-HCl pH 8.0, 1 mM EDTA, and 50 mM NaCl.

For enzyme/DNA-binding studies, 5 µg of purified endo-exonuclease was incubated with 3'-$^{32}$P-labeled junction for 15 min (16° C. in 20 µl of 50mM Tris-HCl, pH 8.0 containing 5 mM EDTA and 1 mM dithiothreitol) and electrophoresed (Parson, C. A. and West, S. C., *Nucl. Acids Res.*, Vol. 18, pp. 4377–4384 (1990)).

Cleavage reactions with the synthetic Holliday junction substrate were carried out at 37° C. for various lengths of time in cleavage buffer (100 mM Tris-HCl, pH 7.5, 10 mM $MgCl_2$, 1 mM dithiothreitol). Reactions were stopped with the addition of 1 µl 0.5M EDTA, and the DNA products visualized by electrophoresis through a 10% polyacrylamide gel using Tris-borate buffer. Resolvase-like activity would be expected to generate linear duplex products.

Figure 14A:
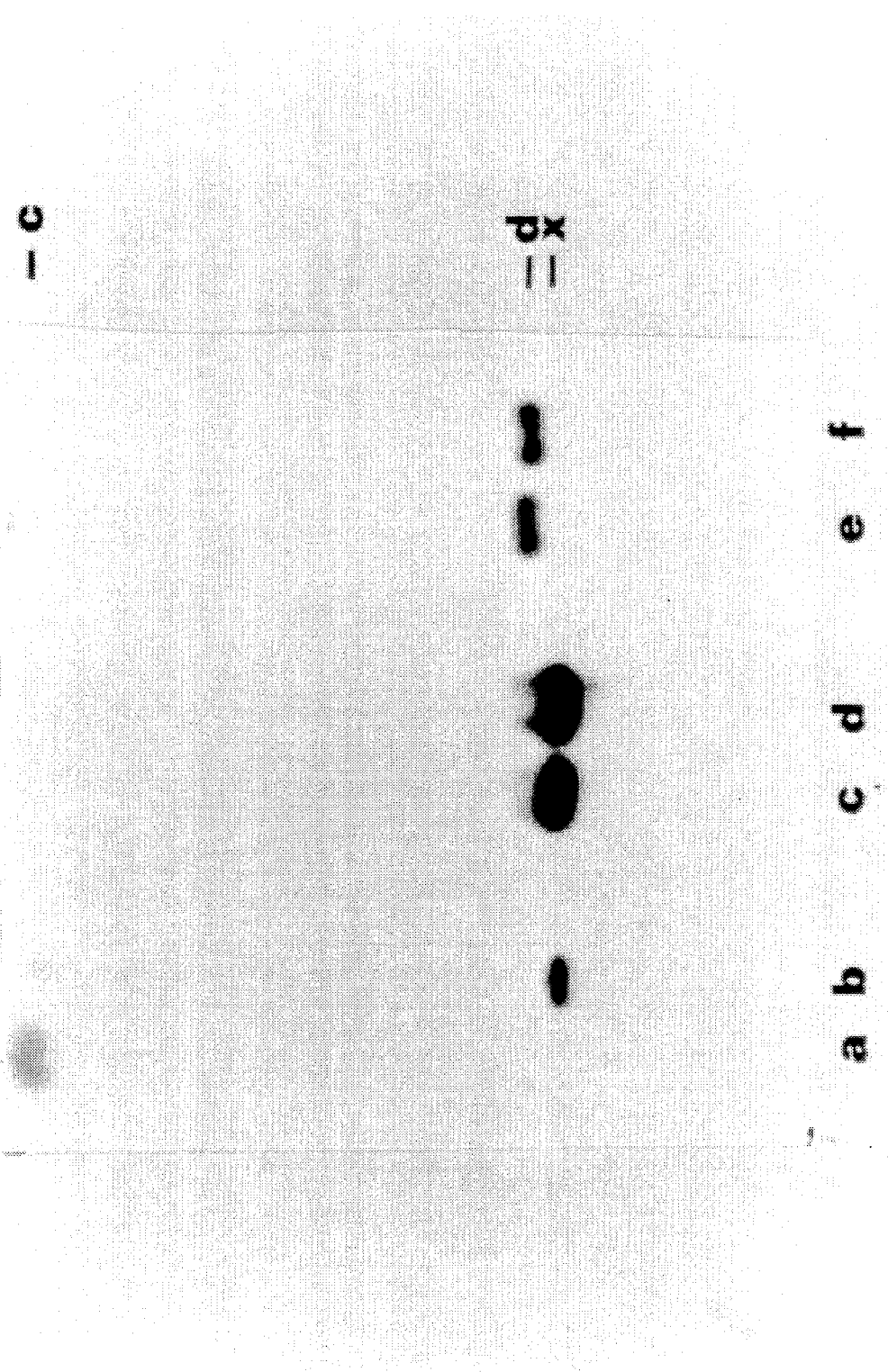

The purified mammalian endo-exonuclease was assayed for its interaction with the synthetic Holliday junction. The presence of the purified endo-exonuclease retarded the migration of the junction molecules on 4% polyacrylamide gel under conditions where the nuclease activities were inhibited. The interaction between the mammalian endo-exonuclease appears to be specific as no retardation was detected with either ss-DNA or with ds-DNA (FIG. 14A).

FIG. 14 shows the results of experiments on the specific binding and cleavage of a four-way DNA (Holliday) junction by the mammalian endo-exonuclease. In Panel A, the binding of Holliday junction DNA by endo-exonuclease is assessed. Purified endo-exonuclease (5 units) was incubated with $^{32}$P-labeled junction molecules, linear ss-DNA (146 nucleotides) or linear ds-DNA (146 nucleotides) according to known methods.

Complexes were resolved on low ionic strength gels and radiolabeled DNA was detected by autoradiography. The protein-DNA complexes formed between the four-way junction and the endo-exonuclease was indicated by the letter "c". The migration of the four-way junction and the ss-DNA fragment were the same and were indicated by the letter "x". The migration of the ds-DNA fragment was indicated by the letter "d". The lanes on Panel A (FIG. 14) of this gel disclose the four-way junction with 5 units of endo-exonuclease (Lane a), the four-way junction only (Lane b), ss-DNA fragments with 5 units of endo-exonuclease (Lane c), and ss-DNA only (Lane d) ds-DNA fragment with 5 units of endo-exonuclease (Lane e), ds-DNA only (Lane f). FIG. 14 (Panel B) discloses the cleavage of four-way junction by endo-exonuclease (2 units). Lane a is a 0 min digestion, and Lanes b–d are 1, 2 and 3 minutes of digestion respectively. Lane e is a 45 minute of digestion and Lane f is a 90 minute digestion.

Figure 14B:
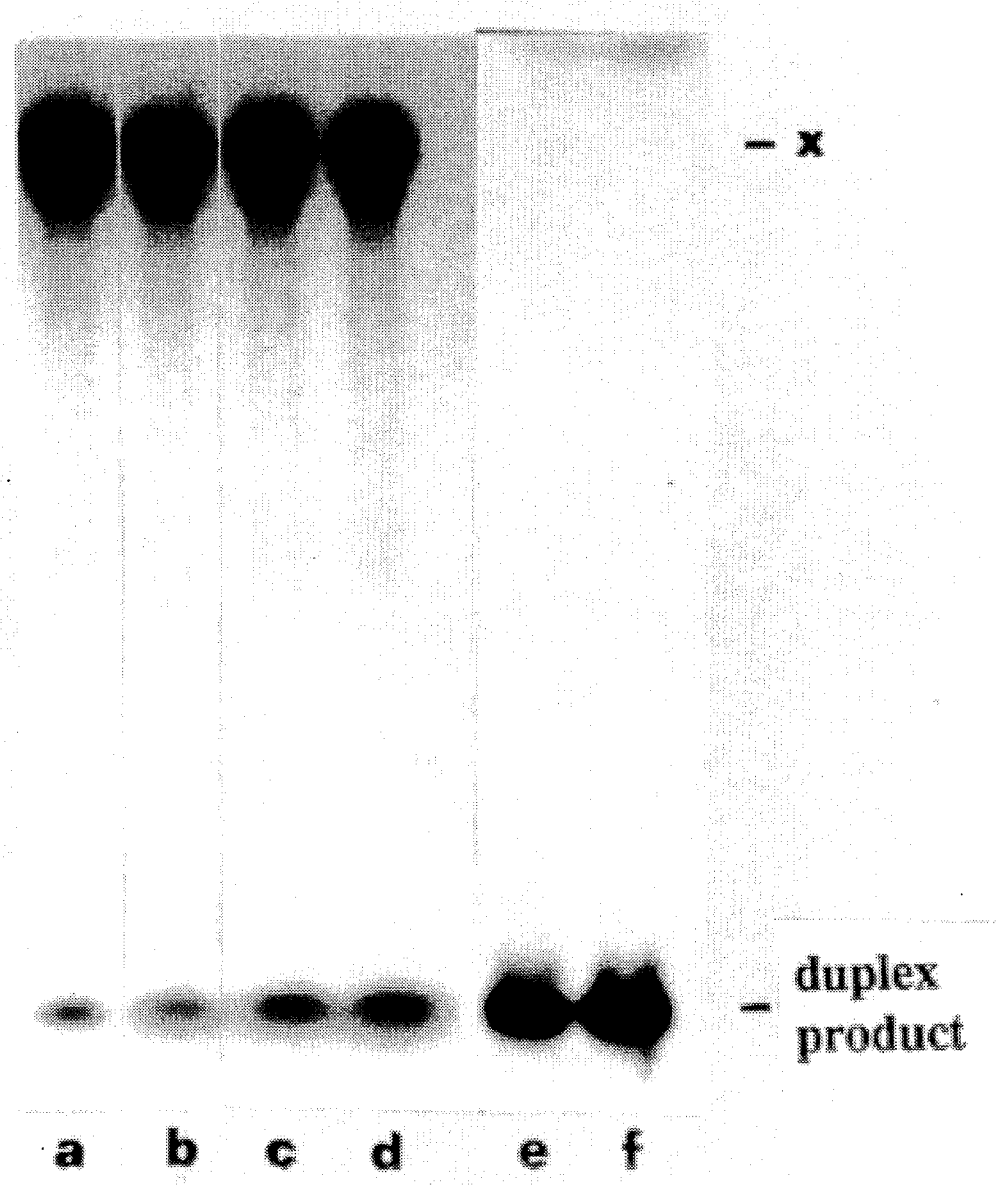

When EDTA was replaced by 10 mM $Mg^{2+}$, the junction was cleaved to form fragments with gel mobilities corresponding to the expected product duplex DNA molecule sizes (FIG. 14B).

K. Comparison of Immune-Crossreactive Materials in CV-1 and COS-1 Cells

The expression of the endo-exonuclease from *N. crassa*, *A. nidulans* and *S. cerevisiae* was maximal during the logarithmic phase of growth, suggesting that it may have a role other than in DNA recombination or repair. To analyze whether the mammalian endo-exonuclease varies with cell stage or development, immune-crossreactive materials from crude extracts of CV-1 cells were compared with those from COS-1 cells. The growth rate of the two cell types was the same; with both reaching confluence from similar numbers of seeded cells over the same time duration. The amount of cross-reactive protein in COS-1 cells was qualitatively four-fold higher than in CV-1 (FIG. 15). This increase was probably not due to protein modification as the specific activity and enzymatic characteristics of the enzyme from CV-1 and COS-1 were similar. It was also found that cross-reactive protein was 5–10 times less in confluent vs. growing CV-1 cells (Chow, unpublished results).

L. Isolation of Human Endo-exonuclease

A gene coding for the Human endo-exonuclease was isolated from a cDNA expression library in lambda gt11. The isolation method followed that described in the above methods for isolating the RNC1 yeast gene from a lambda gt11 expression library. The lambda gt11 clones comprised vector plus inserts derived from human brain mRNA.

Bacteriophage lambda gt11 was infected into *E. Coli* to express the insert protein. Antibodies against *N. Crassa* deoxyribonuclease and the 3' end of the *S. Cerevisiae* endo-exonuclease were used to identify clones with possible endo-exonuclease activity. Two clones cross-reacted with both antibodies, and were therefore chosen for further study and DNA sequencing. Restriction enzyme digestions revealed that both of the isolated clones were identical to each other, and the largest clone (HuNUC) was chosen for DNA sequencing.

SEQ ID NO: 1 is a 238 bp nucleotide sequence corresponding to the complementary strand of a portion of the Human endo-exonuclease gene. A portion of the corresponding amino acid sequence (SEQ ID NO: 2) has a 25% identity with a portion of the *S. cerevisiae* RhoNUC endo-exonuclease (amino acids 213–240).

```
          213                              240
RhoNUC   LHIFK  CSARL  KENID  EVFET  A I HTL  LSD
           |           | | | | |
HuNuc    mstFr  tgrsd  cqpsa  akta T  A I HTL  riv
                                              (SEQ ID NO: 2)
```

SEQ ID NO: 3 is a 223 bp nucleotide sequence corresponding to, another portion of the Human endo-exonuclease gene. A portion of the corresponding amino-acid sequence (SEQ ID NO: 4) has a 26% homology with a portion of the *S. cerevisiae* RhoNUC endo-exonuclease (amino acids 66–91).

```
          66                               91
RhoNUC   KLPDY  HLKIV  VVGDG  AVGKT  CLLIS  Y
                  |      |    | |||| 
HuNUC    ihcta   gpptV  shsgh  gVplT  CLLI c  k
                                              (SEQ ID NO: 4)
```

The area of best fit between the Human endo-exonuclease (SEQ ID NO:4) and the *S. Cerevisiae* RhoNUC endo-exonuclease was in the G-1 box region. There is one portion of the amino acid sequence wherein 6 out of 8 amino acids correspond (SEQ ID NO:5).

```
          81     89
RhoNUC   VGKTC  LLI       (G-I Box Region)
          |  || |||
HuNUC    V p1TC LLI       (SEQ ID NO: 5)
```

This finding provides evidence that the Human endo-exonuclease forms the same chimeric structure as the *S. cerevisiae* endo-exonuclease. The activity of the yeast endo-exonuclease may therefore present a good model of the expected activity of the human enzyme.

Purified primate (CV-1) endo-exonuclease was injected into rabbits to produce antibodies specific for the primate protein. The generation of antibodies used standard protocols for generating antibody in rabbits. A pre-immunization aliquot was removed from the animal as the control. Those of skill in the art know how to isolate and purify an antibody generated by injection of the antigen into a suitable animal, such as a rabbit.

A column comprising bound anti-CV1 endo-exonuclease antibody was used to isolate a nuclease from the human fibroblast cell line AG. Lysed AG cell line homogenates were run over the column. Proteins binding to the affinity column were eluted and found to cross-react with the *S. cerevisiae* anti-endo-exonuclease antibody. Polyacrylamide gel electrophoresis (PAGE) revealed only a single protein was eluted from the affinity column. This cross-reactivity of this protein with both anti-CV1 and *S. cerevisiae* antibodies to the RhoNUC nuclease region provided further evidence that the human protein which bound to the column was an endo-exonuclease.

The nucleolytic activity of the purified human endo-exonuclease paralleled that of the monkey enzyme. Experiments similar to those described above for the CV-1 endo-exonuclease were run on the human purified protein. The majority of nucleolytic activity was in the 5' to 3' direction for ds-DNA, non-processive for ss-DNA, and endonucleolytic for supercoiled DNA. These findings exactly match the activities found for both the yeast and primate endo-exonucleases.

The chimeric nature of the yeast endo-exonuclease, with a nuclease domain and a G protein domain, adds support to the inventive human protein being related to the yeast nuclease in structure and function. Mutants of the human endo-exonuclease may therefore lead to cell growth mutants, in correlation to yeast cells with disfunctional G proteins.

III. FAMILY OF ENDO-EXONUCLEASES

In view of our findings of related endo-exonucleases in such disparate organisms as primates and fungi, we believe that such a related endo-exonuclease can be found in all or nearly all organisms. Moreover, we have evidence that there exists a family of such endo-exonucleases within a single organism. This evidence comes from our studies of material cross-reacting with antibodies to RNC1 in *S. cerevisiae* mutants lacking RNC1. In further studies, we included DNA from the nuclease portion of RNC1 on plasmid DNA and found that this DNA targeted to a chromosome other than the chromosome in which RNC1 is located. Thus, we believe that several related endo-exonucleases within the scope of the present invention can be isolated from certain organisms, including yeast.

In view of the large family of related proteins within the scope of the present invention, mutants lacking one of the known endo-exonucleases can be used to isolate and study related proteins or interacting proteins, including nucleases, from other organisms, including humans. Thus, for example, a RNC1⁻yeast mutant can be used as host for a cDNA expression library from the organism of interest. Yeast from this library exhibiting a phenotype more like wild-type yeast are candidates for carrying a related endo-exonuclease gene from the organism of interest. This gene can be isolated and further studied.

Furthermore, known endo-exonuclease genes can be used to identify factors that interact with the endo-exonuclease. A system for carrying out such a method has been described by Chien et al (*Proc. Natl. Acad. Sci*, 88:9578–9582 (1991)) for studying interactions with the SIR4 C-terminal domain in yeast. Briefly, to use this system for investigating factors interacting with a known endo-exonuclease, plasmids are constructed encoding two hybrid proteins. One of these hybrids consists of the DNA-binding domain of the yeast transcriptional activator protein GAL4 fused to the known endo-exonuclease. The other hybrid consists of the GAL4 activation domain fused to protein sequences encoded by a library of genomic DNA fragments from an organism of interest. Interaction between the known endo-exonuclease and a protein encoded by one of the library plasmids leads to transcriptional activation of a reporter gene containing a binding site for GAL4. Thus, proteins from the library can be identified that interact with the known endo-exonuclease.

IV. ROLE OF ENDO-EXONUCLEASES IN GROWTH

As stated above, it is known that RhoNUC activity in both mitotic and meiotic cells is greatly influenced by other genes. In certain mutants, the mitotic level of the endo-exonuclease is less than 10% of the wild type level, and no increase is observed during meiosis. We investigated the role that the endo-exonucleases of the present invention play in regulation of growth.

A. Effect on Growth of Endo-Exonuclease Mutations

Mutations in the GTP binding regions of the human ras gene are known to affect cell growth. Specifically, mutations in any of the four GTP binding areas (boxes) of ras cause many cell types to enter a tumorgenic growth stage. Mutations were made in the GTP binding boxes of RNC1 to look for altered growth patterns.

FIG. 16 shows the results of an experiment designed to analyze the effect of mutations to the G-box region of RNC1 on cellular growth. Yeast cells were grown in standard media, as described above, and transfected with either RNC1, RNC1-81 (G1), RNC1 -130 (G2), RNC1-187 (G3), or plasmid alone (control). In human ras, mutations G 1, G2, and G2 are located at amino acid positions 12, 61, and 119 respectively (FIG. 16). In RhoNUC the G1, G2, and G3 mutations are located at amino acid positions 81 (G changed to V), 130 (Q changed to L), and 187 (D changed to A) respectively. These mutations are all in regions having amino acid homology to the human ras G-boxes.

As seen in FIG. 16, the RNC1-130 mutation caused the cell to dramatically decrease its growth rate. The normal doubling time is approximately 2 hours, but for the RNC1 mutant, the doubling time was 3.2 hours at 30° C. (A) and 4.5 hours at 37° C. (B). A comparison of graphs (A) and (B) shows that cell growth at 30° C. is similar to cell growth at 37° C. for both controls and mutants. The RNC1-130 mutation which affected growth at 30° C. also affects growth at 37° C.

Thus, the endo-exonucleases of the present invention appear to be important in regulating cell growth.

B. Control of Susceptibility to DNA Damage

A further series of experiments, was based on the observation that DNA damage can arrest cell growth in many organisms, including yeast and mammalian cells, until DNA repair can be completed. See Hartwell et al., *Science*, 246:629–634 (1989). We have shown that in the absence of the ability to repair DNA, that cells die, even when the damage is to non-essential regions of DNA. Thus, the DNA damage has a trans-acting signalling effect.

In our experimental data, we examined the effect of a double-stranded break in plasmid DNA in both wild-type and RNC⁻ yeast cells. These cells were deprived of the homologous DNA required to repair DNA. We found that in a RNC⁻ mutant yeast cell, this trans-acting signal is blocked, and damage to non-essential DNA, such as a double-stranded break in a plasmid, no longer leads to arrest of cellular growth and death. In wild-type yeast cells undergoing the same procedure, a double-stranded break to plasmid DNA caused eventual cell death. Thus, we believe that the endo-exonucleases of the present invention, such as the yeast RNC protein, can be used to control the susceptibility of cells to DNA damage. Thus, we believe that controlling endo-exonuclease activity can be used to regulate cell growth.

The level of endo-exonuclease activity can be controlled by adding endo-exonuclease itself to increase activity or an agonist thereof, such as an antibody directed thereto, to reduce activity. Antibody agonists can be prepared in a manner known to those of ordinary skill in the art. Thus, addition of either endo-exonuclease itself or an agonist thereof to cells can be used to control the level of cell growth

V. ROLE OF ENDO-EXONUCLEASES IN RECOMBINATION

We performed a group of experiments to determine if RNC1 had any effect on recombination. A plasmid was used which contained direct repeats of the ura3 gene surrounding an intervening sequence. One of the ura3 genes was defective, while the other repeat was wildtype, making the cell ura$^+$. Between these repeats, in the intervening sequence, was the adenine 2 gene. Rad52 (Bar 1), rad52/rnc1 (Bar 2), rnc1 (Bar 3), or wild type (Bar 4) cells, containing the plasmid were first grown in 5-floro-orotic acid to select for those cells which converted through recombination to ura$^{31}$. Only ura⁻ cells can grow on this compound. If a reciprocal exchange has occured, the plasmid will have lost its intervening sequence (adenine 2) and will become red in color. Cells with an active adenine 2 gene would remain white. The number of cells which underwent a successful, reciprocal recombination event is plotted on the Y-axis of FIG. 17 and indicates the cells ability to perform direct repeat-type recombination.

Mutations in the rad52 gene greatly decreased the level of recombination, while a double mutant (rad52/rnc1) showed almost wildtype recombinational frequency (FIG. 17). In this instance, RNC1 rescued the rad52 cells ability to recombine. A rnc1 mutant was able to recombine at a level in excess of any other mutant. These data indicate that the RNC1 gene plays an active role in recombination.

The foregoing experiments indicate that RNC1 can relieve the defect of recombination of Rad52 cells. We believe that RNC1 and its related endo-exonucleases in yeast and other species has an important role in recombination. Accordingly, we have further discovered that controlling the activity of endo-exonucleases such as RNC1, can provide regulation of recombination that is useful in a number of areas.

A. Gene Therapy

One area in which the role of endo-exonucleases can provide a therapeutically useful role is in gene therapy or in the development of transgenic organisms for other purposes. In these techniques, a targetting mechanism, such as antisense oligonucleotides or an appropriate antibody, is used to direct the desired DNA or other oligonucleotides to the appropriate site in cells. These techniques generally rely on endogenous recombination mechanisms to provide transformation with the desired oligonucleotides. Problems associated with this technique have included a very low rate of transformation, as well as the production of high levels of undesired genetic rearrangements.

Use of the endo-exonucleases of the present invention addresses both of the foregoing problems. The level of endo-exonuclease activity can be controlled by adding endo-exonuclease itself to increase activity or an agonist thereof, such as an antibody directed thereto, to reduce activity. Antibody agonists can be prepared in a manner known to those of ordinary skill in the art. Thus, if an insufficient level of transformation is occurring, endo-exonuclease or its agonist can be added to the cells being transformed or transfected in order to increase the rate of recombination, resulting in an enhanced cellular transfection. Alternatively, if undesired genetic rearrangements are occurring, then addition to the cells of an endo-exonuclease or its agonist, can decrease the activity of the endogenous endo-exonucleases, resulting in decreased recombination and a decreased level of undesired rearrangements.

Addition of endo-exonucleases or their agonists can be used along with protocols known to those having ordinary skill in the art for production of transgenic organisms. The amount of endo-exonuclease added should be about $10^2$ to $10^8$ molecules of endo-exonuclease per cell, depending generally on the volume of the cell. Thus, for a large cell, such as a Xenopus oöcyte, the amount of endo-exonuclease used will be in the higher amount of this range, i.e. about $10^5$ to $10^8$ molecules per cell. Similar numbers of endo-exonuclease agonist molecules should be added per cell to effect the desired decrease in recombination. Too many agonist molecules can prevent recombination entirely. Thus, not so many agonist molecules should be added that all recombination is prevented.

B. Cancer Therapy

The endo-exonucleases of the present invention can also be used as an adjuvant to anti-cancer therapies, such as radiation therapy and chemo-therapy, in which cells actively undergoing cellular division are selectively killed. We believe that administration of the endo-exonucleases of the present invention or an agonist thereto can control such therapies. Thus, use of endo-exonuclease or agonists thereof can selectively increase or reduce the effect of such therapies.

C. Antibody Diversity

Since genetic recombination appears to be an important part of the generation of antibody diversity, we believe that the endo-exonucleases of the present invention are related to the generation of antibody diversity. Thus, the present invention includes a method for determining if an agent affects the production of antibody diversity in a mammal using an in vitro model for production of antibody diversity. This method includes obtaining and culturing B cell precursor cells from the mammal using methods known to those of ordinary skill in the art. The resulting cell culture can then be divided into a first group of cells and a second group of cells. In this method, an endo-exonuclease is then added to the first group of cells in the presence of an antigen to determine a normal rate of antibody production. Then, the endo-exonuclease is added to the second group of cells in the presence of the agent and the antigen to determine the rate of antibody production in the presence of the agent. By comparing the normal rate of antibody production to the rate of antibody production in the presence of the agent, the effect that the agent has on the production of antibody diversity can be evaluated: an increased rate of antibody production in the presence of the agent indicates that the agent augments the production of antibody diversity and a decreased rate of antibody production in the presence of the agent indicates that the, agent retards the production of antibody diversity.

VI. IDENTIFICATION OF A CANCEROUS OR A PRE-CANCEROUS TISSUE

Since the amount of Mammalian endo-exonuclease was higher in the SV40 transformed COS-1 cell line than the normal CV-1 cell line, it is reasonable to infer that the level of RhoNUC may provide a diagnostic tool for identifying transformed tissue samples.

Tissue samples from a patient suspected of having cancer or pre-cancer are obtained. The mRNA from the tissue is isolated by lysing the cells and removing the nuclei. These methods are known to those in the art. A Northern blot is run comparing normal tissue to the patients tissue. A radiolabeled clone corresponding to SEQ ID NO: 3 is hybridized with the Northern blot overnight. The amount of hybridization between SEQ ID NO: 3 and the mRNA fraction from a patient is measured. The level of human endo-exonuclease from normal cells is compared to the patient's cells. Higher levels of nuclease mRNA in the patient's cells indicate the possibility of cancer or pre-cancer.

Other methods of determining cancerous or pre-cancerous tissue can rely on protein level measurements instead of determining mRNA quantities. By using the anti-human endo-exonuclease antibody provided above, those with skill in the art can use many different experimental protocols to determine the endo-exonuclease levels in the suspect sample as compared to a normal sample. These protocols include many of the known procedures, such as IFA, immunoblots, radio immunoassays, RIST, enzyme linked immunoassays, agglutination, and hemagglutination procedures. Those of skill in the art can determine other suitable protocols. A higher level of endo-exonuclease in the patient's sample, as compared with the control, indicates the likelihood that the sample includes cancerous or pre-cancerous tissue and can also indicate the responsiveness thereof to cancer therapies. The normal control can be taken from a sample of the same type from a mammal known not to have cancer.

VII. DETERMINATION OF MAMMALIAN GERM CELL VIABILITY

The CV-1 and human endo-exonuclease have been shown to be important in cellular recombination, as evidenced by the above experiments on the synthetic Holliday junction. Lowered levels of endo-exonuclease correspond to a reduced ability for the cell to undergo recombination (Taylor, A., *Genetic Recombination* eds. R. Kucherlapati and G. R. Smith, (1988) 231–264). We therefore believe that a reduction in endo-exonuclease activity is indicative of a reduced chance of cellular recombination. The following experiment reveals one way of measuring the endo-exonuclease activity of a germ cell.

Human sperm cells are obtained and the proteins isolated by methods known to those of skilled in the art. For instance, the sperm cells can be lysed and the resultant protein mixture contacted with radiolabeled anti-human endo-exonuclease antibody. The level of conjugates formed by the antibody and endo-exonuclease can be measured by scintillation counting of the antibody's radioactive label.

Sperm cells from a normal patient can be used as a control to determine if the tested sperm contains unusually low levels of endo-exonuclease. We believe that low levels of endo-exonuclease can lead to a lack of recombinational control and a lowered fertility rate.

Other similar experiments can be run on ovum, or semen, in order to determine those cells having endo-exonuclease activity. Other detection methods are envisioned to be covered by this invention. These methods include IFA, Immunoblots, RIA, RIST, ELISA, agglutination, and hemagglutination. Such methods of determining the quantity of an antigen are known by those having ordinary skill in the art.

VIII. PREVENTION OF ULTRAVIOLET RADIATION DAMAGE TO CELLS

Ultraviolet light is known to cause DNA damage to cells. The above experiments using primate endo-exonuclease on UV irradiated *E. Coli* revealed that insertion of the endo-exonuclease gene into bacteria protected against UV damage. It may be possible therefore to use a pharmaceutically active composition in vivo to prevent UV damage. The following protocol details how to provide UV protection using an endo-exonuclease.

A concentration of mammalian endo-exonuclease is mixed with a topical carrier and applied to the skin. The active concentration of endo-exonuclease is between 1 unit/ml and 100 units/ml. Known topical carriers are solutions such as DMSO.

The topical carrier can be used in conjunction with known sunscreen ingredients such as para amino-benzoic acid (PABA) to help prevent skin damage and possible skin cancer. Other topical ointments and oils may be used in conjunction with endo-exonuclease to provide a suitable topical carrier and sunscreen.

IX. TREATMENT OF IMMUNE DISORDERS

We believe that the recombinational activity of the endo-exonuclease is related to the mammalian production of antibodies in the thyroid. In the thyroid, DNA cross-over events (recombination) are responsible for producing the wide variety of antibodies in vivo. We believe that endo-exonuclease activity can also be important for allowing these cross-over events to occur. Evidence for this possibility is seen in the above experiments related to the synthetic Holliday junction. The following protocol outlines how to use an endo-exonuclease to treat immune disorders.

Disorders that can be treated using methods of the present invention include diseases such as congenital hypogammaglobulinemia; transient hypogammaglobulinemia of infancy; acquired hypogammaglobulinemia; selective deficiencies of IgA, IgM or IgG subclasses; secondary B cell immunodeficiency associated with drugs or protein-losing states; B cell immunodeficiency associated with 5'-nucleotidase deficiency or other enzyme deficiency; and X-linked lymphoproliferative disease.

A mammal with a reduced ability to produce antibodies is treated with a pharmacalogically active concentration of mammalian endo-exonuclease. Blood is obtained from the mammal and the red blood cells are centrifuged and pelleted. The remaining suspension of white blood cells (containing antibody) is tested for cross-reactivity against known antigenic determinants. Negatively cross-reacting antigens are noted. A pharmaceutically effective composition of endo-exonuclease is contacted with the mammal. This treatment is by way of intrathyroidal injection, or any other method of contacting the thyroid cells with the active endo-exonuclease. Other methods of delivering the pharmacalogically active endo-exonuclease include administration orally, intravenously, intraperitoneally, or intramuscularly. Preferred dosages will provide approximately $10^2$ to $10^8$ molecules of endo-exonuclease per cell being treated.

After treatment the mammal is tested for an increased cross-reactivity to the previously tested antigenic determinants. A positive cross-reactivity to a previously negative antigen indicates an increased variation in antibody diversity.

X. DETERMINATION OF FERTILITY

Recombination is known to be important in producing fertile germ cells. Thus, another aspect of the present invention provides a method of determining whether a mammalian germ cell is capable of producing viable offspring. This method includes obtaining a sample containing at least one germ cell from the mammal, determining the amount of mammalian endo-exonuclease present in the sample, and comparing the determined amount of mammalian endo-exonuclease present in the sample with the amount of mammalian endo-exonuclease expected in a normal sample of the same type as the sample. The normal sample can be taken from a control individual of the same species that is known to be fertile. In this assay, a decreased amount of mammalian endo-exonuclease present in the sample compared to a normal sample indicates a lowered likelihood that the germ cell is capable of producing viable offspring. The sample can include an ovum and can also be semen or other sample including a sperm cell. In a preferred form of this method, the determining step makes use of one of the following assays: IFA, immunoblots, RIA, RIST, ELISA, agglutination and hemagglutination. Thus, the determining step can include contacting an antibody that specifically binds to mammalian endo-exonuclease with the sample.

XI. OVERVIEW OF CERTAIN ASPECTS OF THE PRESENT INVENTION

An endo-exonuclease from mammalian cells is disclosed. This enzyme was found to cross-react with an antibody raised against *N. crassa* endo-exonuclease and antibody against the nuclease portion of RhoNUC. This antibody is specific since it did not cross-react with Micrococcus nuclease, Aspergillus $S_1$ nuclease or other nucleases with ss-DNase activity (Fraser, M. J., Koa, H. and Chow, T. Y.-K, *J. Bacteriol.*, Vol. 172, pp. 507–510 (1990)). The antibody was specific for the mammalian endo-exonuclease since only one protein bound on the antibody affinity column (FIGS. 8 and 9). The major protein eluted from the affinity column ($b_2$) appeared to have a molecular size of 67 kDa (FIGS. 8C, 8D).

The enzymatic characterization of the purified endo-exonuclease from CV-1 cells showed that its actions were very similar to the *N. crassa* ss-DNA-binding endo-exonuclease, the *A. nidulans* endo-exonuclease, the *U. maydis* nuclease, the *S. cerevisiae* endo-exonuclease (yNucR or RhoNUC), and the *E. coli* exonuclease V. In comparing the three endo-exonucleases from *N. crassa*, *S. cerevisiae*, and *A. nidulans* to the CV-1 cell enzyme, the mammalian endo-exonuclease was more similar to the endo-exonuclease of yeast than *N. crassa*. Like the partially purified N. crassa endo-exonuclease, no evidence of inactive precursors of the mammalian enzyme was found. Immuno-blots of the proteins from fleshly prepared cell extracts, after electrophoresis on a 10% polyacrylamide gel, identified only one major protein of 65 kDa, a molecular size corresponding to the purified endo-exonuclease (FIGS. 8C, 8D). No protein of size greater than 65 kDa cross-reacted with the antibody.

The similarities of the enzymatic properties and immunoreactivities between the mammalian endo-exonuclease reported here and the single strand-specific endonuclease from mouse cell mitochondria suggests the possibility that the two proteins are related. However, the molecular size of the mammalian polypeptide of the present invention (65kd) is much larger than the polypeptide of the mouse mitochondrial endonuclease (37.4 kd). The latter is almost identical in size to the yeast mitochondrial endo-exonuclease, 38 kDa (Dake, E., Hofmann, T. J., McIntire, S., Hudson, A. and Zassenhaus, H. P., *J. Biol. Chem.*, Vol. 263, pp. 7691–7702 (1988)), and to one of the active polypeptides found in extracts of *N. crassa* mitochondria (Fraser, M. J., Chow, T. Y.-K., Cohen, H. and Koa, H., *Biochem. Cell. Biol.*, Vol. 64, pp. 106–116 (1986)).

In addition, the activity of the CV-1 cell endo-exonuclease toward ds-DNA substrates is much higher than the activity exhibited by the mouse mitochondrial enzyme. The ratio of ss/ds-DNase activity of the endo-exonuclease is 1.3, whereas the mitochondrial enzyme is single-strand-specific. Furthermore, analysis of the localization of the mammalian endo-exonuclease using an in vivo immunofluorescence method found that the CV-1 cell endo-exonuclease is located in the nuclei. It is possible that the mouse mitochondrial enzyme is an in vitro proteolytic product of a larger endo-exonuclease, much as occurs in extracts of *N. crassa*, or could be the product of a distinct gene as is the case for *S. cerevisiae*.

Possible function(s) of the mammalian endo-exonuclease in recombination are suggested from its endonucleolytic activity on supercoiled DNA followed by the production of a double-strand break (FIG. 10) and its processive exonucleolytic digestion of linear double-strand DNA (FIG. 10 and FIG. 13). We believe that these activities are important in resolution of the covalent Holliday intermediate in proposed general mechanisms for recombination or specifically in recombinational double-strand break repair. The evidence presented in FIG. 14 indicates that the enzyme does cleave a Holliday junction intermediate at least in vitro.

The 5'→3' directionality of the processive exonucleolytic activity on ds-DNA would result in the generation of 3'-overhangs that can be used in strand-switching during recombination. These intermediates are observed in yeast mating-type switching (White, C. I. and Haber, J. E., *EMBO J.*, Vol. 9, pp. 663–673 (1990)), in vivo homologous DNA recombination with plasmid DNA substrates and in nuclear extracts of *Xenopus laevis* oocytes (Maryon, E. and Carroll, D., *Molec. Cell. Biol.*, Vol. 11, pp. 3268–3277 (1991a)).

The mammalian endo-exonuclease may have functions other than in recombination and/or repair. Studies of the *N. crassa* and the *S. cerevisiae* endo-exonucleases have shown that the protein is expressed maximally during rapid vegetative growth, while little or no protein can be detected in extracts of stationary phase cells (Chow, T. Y.-K and Fraser, M. J., *Can. J. Biochem.*, Vol. 57, pp. 889–901 (1979)). The expression of the mammalian endo-exonuclease is much higher in the SV40 transformed COS-1 cells than in the CV-1 cells (FIG. 15). Recently, the gene coding for the *S. cerevisiae* nuclear endo-exonuclease has been cloned. In vitro mutagenesis of the cloned yeast gene generated some mutants which phenotypically resembled cell cycle mutants. The gene was directly demonstrated to be involved in recombination. Deletion of the RNC1 gene relieved the defect in recombination observed for a rad52 mutant. Thus, it may provide an alternate pathway for spontaneous recombination. The mammalian endo-exonuclease may also have some essential role in mitotic growth and recombination.

VI. COMPONENTS OF THE PRESENT INVENTION RELATING TO FUNGAL ENDO-EXONUCLEASES

In one embodiment, the DNA segment has the sequence shown in FIG. 2 or allelic or species variation thereof. FIG. 2 also shows the amino acid sequence encoded by this DNA segment, and the present invention also includes allelic or species variation of this amino acid sequence.

The present invention relates to a polypeptide free of proteins with which it is naturally associated (or bound to a solid support) and having an amino acid sequence encoding a human rho motif wherein the polypeptide has deoxyribonuclease activity and is RhoNUC. In one preferred embodiment, the polypeptide has the amino acid sequence set forth in FIG. 2, or allelic or species variation thereof.

The present invention also relates to a recombinant DNA molecule comprising a vector (for example, a plasmid or vital vector) and the DNA segment described by FIG. 2. The encoding DNA segment can also be present in the vector operably linked to a promoter.

The present invention is also envisioned to include host cells containing the above-described recombinant DNA molecule. Suitable host cells include procaryotes (such as bacteria, including *E. coli*) and both lower eukaryotes (for example, yeast) and higher eucaryotes (for example, mammalian or Drosophila cells). Introduction of the recombinant molecule into the host cell can be effected using methods known in the art.

The present invention also relates to a cell containing the RNC1 gene, wherein the RNC1 gene contains a mutation in a region of the gene encoding an amino acid sequence that confers deoxyribonuclease activity on the protein product.

The present invention also includes cells containing the RNC1 gene, wherein the RNC1 gene contains a mutation in the region of the gene that encodes an amino acid sequence that contains the rho/ras oncogeny-like motif.

The present invention relates to a DNA segment that complements the above-described mutations.

The present invention relates to an antibody having binding affinity to RhoNUC, or a unique portion thereof. In one preferred embodiment, RhoNUC has the amino acid sequence set forth in FIG. 2, or allelic or species variation thereof. In another preferred embodiment, the unique portion is selected from the group corresponding to amino acid position 1–395 set forth in FIG. 2, amino acid position 1–195 set forth in FIG. 2, amino acid position 195–486 set forth in FIG. 2, or amino acid position 395–486 set forth in FIG. 2.

Antibodies can be raised to RhoNUC, or unique portions thereof, in its naturally occurring form and in its recombinant form. Additionally, antibodies can be raised to RhoNUC in both its active form and inactive form, the difference being that antibodies to the active RhoNUC are more likely to recognize epitopes which are only present in the active RhoNUC.

RhoNUC may be joined to other materials, particularly polypeptides, as fused or covalently joined polypeptides to be used as immunogens. RhoNUC or its fragments may be fused or covalently linked to a variety of immunogens, such as keyhole limpet hemocyanin, bovine serum albumin, tetanus toxoid, etc. See, for example, Microbiology, Hoeber Medical Division (Harper and Row, 1969), Landsteiner, Specificity of Serological Reactions (Dover Publications, New York, 1962) and Williams, et al., Methods in Immunology and Immunochemistry, Vol. 1 (Academic Press, New York, 1967) for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites, et al., editors, Basic and Clinical Immunology (Lange Medical Publications, Los Altos, Calif., 4th edition) and references cited therein, and in particular in Kohler and Milstein in *Nature* 256:495–497 (1975), which discusses one method of generating monoclonal antibodies.

The present invention relates to a method of producing the above-described polypeptide, comprising culturing the above-described host cells under conditions such that the polypeptide is produced, and isolating the polypeptide.

The present invention relates to a method of controlling cell cycle comprising introducing into a host cell the above-described DNA segment and effecting expression of the DNA segment under conditions such that the cell cycle is controlled. This can be accomplished by increasing the copy number or expression of the RhoNUC which results in altered cell growth and formation of nuclei. Alternatively, growth can be modified by chemicals that would interfere with either or both the rho-related function or the deoxyribonuclease function.

The present invention relates to a method of controlling cell development comprising introducing into a host cell the above-described DNA segment and effecting expression of the DNA segment under conditions such that the cell development is controlled. This would provide for the regulation and/or delay of germinal development either by overexpression or underexposure of the RNC1 gene or modifications of portions of that gene. Alternatively, development may be modified by chemicals that can interfere with either or both the rho-related function of the deoxyribonuclease function.

The DNA sequences and polypeptides according to this invention exhibit a number of utilities, including, but not limited to:

1. Utilizing the RNC1 DNA sequence or the RhoNUC polypeptide to isolate mutants from yeast or other organisms and to study these mutants.
2. Utilizing the RNC1 DNA sequence or the RhoNUC polypeptide to characterize agents and drugs that would modify cellular growth and development.
3. Utilizing the RNC1 DNA sequence or the RhoNUC polypeptide to isolate associated proteins.
4. Utilizing the RhoNUC polypeptide, as well as proteins from related mutants, to obtain antibodies to the entire RhoNUC protein or various internal epitopes.

XII. CONCLUSION

All publications cited hereinabove are hereby incorporated herein in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated primate endo-exonuclease.

2. An isolated mammalian endo-exonuclease having greater activity in the 5'→3' direction than in the 3'→5' direction.

3. An isolated mammalian endo-exonuclease having exonuclease activity on double-stranded polynucleotides and endonuclease activity on single-stranded polynucleotides.

4. An isolated endo-exonuclease according to either claim 1 or claim 2, wherein said endo-exonuclease has exonuclease activity on double-stranded polynucleotides and endonuclease activity on single-stranded polynucleotides.

5. An isolated endo-exonuclease according to either claim 1 or claim 3, wherein said endo-exonuclease has greater activity in the 5'→3' direction than in the 3'→5' direction.

6. An isolated endo-exonuclease according to either claim 2 or claim 3, wherein said endo-exonuclease is a primate endo-exonuclease.

7. An isolated human endo-exonuclease according to claim 1.

8. The endo-exonuclease of claim 2, wherein said endo-exonuclease has at least one epitope in common with a *N. Crassa* or a *S. cerevisiae* endo-exonuclease.

9. The endo-exonuclease of claim 2, wherein said endo-exonuclease is derived from Monkey CV-1 cells.

10. The endo-exonuclease of claim 2, wherein said endo-exonuclease is derived from Monkey COS-1 cells 11. An isolated multi-domain protein with N-terminal homology to the rho oncogene and endogenous nuclease activity wherein said protein is derived from a primate.

12. The multi-domain protein of claim 11 wherein said primate is a human.

* * * * *